(12) United States Patent
Kesteleyn et al.

(10) Patent No.: US 10,689,340 B2
(45) Date of Patent: Jun. 23, 2020

(54) SUBSTITUTED INDOLINE DERIVATIVES AS DENGUE VIRAL REPLICATION INHIBITORS

(71) Applicants: Janssen Pharmaceuticals, Inc., Titusville, NJ (US); Katholieke Universiteit Leuven, Leuven (BE)

(72) Inventors: Bart Rudolf Romanie Kesteleyn, Berlare (BE); Pierre Jean-Marie Bernard Raboisson, Rosieres (BE); Jean-François Bonfanti, Ande (FR); Dorothée Alice Marie-Eve Bardiot, Heverlee (BE); Arnaud Didier M Marchand, Bierbeek (BE)

(73) Assignees: Janssen Pharmaceuticals, Inc., Titusville, NJ (US); Katholieke Universiteit Leuven, Leuven (BE)

( * ) Notice: Subject to any disclaimer, the term of this patent is extended or adjusted under 35 U.S.C. 154(b) by 0 days.

(21) Appl. No.: 16/088,090

(22) PCT Filed: Mar. 31, 2017

(86) PCT No.: PCT/EP2017/057661
§ 371 (c)(1),
(2) Date: Sep. 25, 2018

(87) PCT Pub. No.: WO2017/167951
PCT Pub. Date: Oct. 5, 2017

(65) Prior Publication Data
US 2019/0112266 A1  Apr. 18, 2019

(30) Foreign Application Priority Data

Apr. 1, 2016  (EP) ..................................... 16163488

(51) Int. Cl.
C07D 209/08      (2006.01)
C07D 209/26      (2006.01)
A61P 31/14       (2006.01)

(52) U.S. Cl.
CPC ............ *C07D 209/08* (2013.01); *A61P 31/14* (2018.01); *C07D 209/26* (2013.01); *C07B 2200/07* (2013.01)

(58) Field of Classification Search
CPC ............................... C07D 209/08; A61P 31/14
See application file for complete search history.

(56) References Cited

U.S. PATENT DOCUMENTS

| 7,601,735 | B2 | 10/2009 | Tyms et al. |
| 8,524,764 | B2 | 9/2013 | Canales et al. |
| 8,884,030 | B2 | 11/2014 | Canales et al. |
| 8,993,604 | B2 | 3/2015 | Byrd et al. |
| 9,029,376 | B2 | 5/2015 | Byrd et al. |
| 9,522,923 | B2 | 12/2016 | Richards et al. |
| 9,944,598 | B2 * | 4/2018 | Kesteleyn ............ C07D 209/14 |
| 10,029,984 | B2 * | 7/2018 | Kesteleyn ............ C07D 209/14 |
| 10,064,870 | B2 | 9/2018 | Rajagopalan et al. |
| 10,071,961 | B2 | 9/2018 | Vandyck et al. |
| 10,117,850 | B2 | 11/2018 | Griffioen et al. |
| 10,206,902 | B2 * | 2/2019 | Kesteleyn ............ C07D 209/14 |
| 10,323,026 | B2 | 6/2019 | Ikeda et al. |
| 2005/0239821 | A1 | 10/2005 | Neyts et al. |

(Continued)

FOREIGN PATENT DOCUMENTS

WO       D2089780 A2    11/2002
WO       D3050295 A2    6/2003

(Continued)

OTHER PUBLICATIONS

Prasad L. Polavarapu, et al., Intrinsic Rotation and Molecular Structure, Chirality 15: S143-S149 (2003).

(Continued)

*Primary Examiner* — Golam M Shameem
(74) *Attorney, Agent, or Firm* — Amster, Rothstein & Ebenstein LLP

(57) ABSTRACT

The present invention concerns substituted indoline derivatives, methods to prevent or treat dengue viral infections by using said compounds and also relates to said compounds for use as a medicine, more preferably for use as a medicine to treat or prevent dengue viral infections. The present invention furthermore relates to pharmaceutical compositions or combination preparations of the compounds, to the compositions or preparations for use as a medicine, more preferably for the prevention or treatment of dengue viral infections. The invention also relates to processes for preparation of the compounds.

8 Claims, No Drawings
Specification includes a Sequence Listing.

(56) References Cited

U.S. PATENT DOCUMENTS

| | | |
|---|---|---|
| 2006/0194835 A1 | 8/2006 | Dugourd et al. |
| 2006/0211698 A1 | 9/2006 | Botyanszki et al. |
| 2008/0318338 A1 | 12/2008 | Kamal |
| 2016/0297810 A1 | 10/2016 | Bardiot et al. |
| 2017/0002006 A1 | 1/2017 | Corte et al. |
| 2017/0096429 A1 | 4/2017 | Corte et al. |
| 2017/0281633 A1 | 10/2017 | Boylan et al. |
| 2017/0298017 A1 | 10/2017 | Kesteleyn et al. |
| 2018/0256544 A1 | 9/2018 | Kesteleyn et al. |
| 2018/0256545 A1 | 9/2018 | Kesteleyn et al. |
| 2018/0346419 A1 | 12/2018 | Kesteleyn et al. |
| 2019/0104738 A1 | 4/2019 | Marine et al. |

FOREIGN PATENT DOCUMENTS

| | | |
|---|---|---|
| WO | 2009149054 A1 | 12/2009 |
| WO | WO 2010/021878 A1 | 2/2010 |
| WO | 2011037643 A2 | 3/2011 |
| WO | 2011088303 A1 | 7/2011 |
| WO | WO 2013/045516 A1 | 4/2013 |
| WO | 2016050841 A1 | 4/2016 |
| WO | 2016053455 A1 | 4/2016 |
| WO | 2017079216 A1 | 5/2017 |
| WO | 2017167832 A1 | 10/2017 |
| WO | 2017167950 A1 | 10/2017 |
| WO | 2017167952 A1 | 10/2017 |
| WO | 2017167953 A1 | 10/2017 |
| WO | 2017171100 A1 | 10/2017 |
| WO | 2017173206 A1 | 10/2017 |
| WO | 2018178238 A1 | 10/2018 |
| WO | 2018178240 A1 | 10/2018 |
| WO | 2018215315 A1 | 11/2018 |
| WO | 2018215316 A1 | 11/2018 |

OTHER PUBLICATIONS

Prevention, Dengue, Centers for Disease Control and Prevention (Sep. 27, 2012) https://www.cdc.gov/dengue/prevention/index.html, internet.

Lidia Moreira Lima et al., Bioisosterism: A Useful Strategy for Molecular Modification and Drug Design, Current Medicinal Chemistry, Bentham Science Publishers Ltd. (2005) 12, pp. 23-49.

Ian Stansfield et al., Development of carboxylic acid replacements in indole-N-acetamide inhibitors of hepatitis C virus NS5B polymerase, Bioorganic & Medicinal Chemistry Letters 17 (2007) 5143-5149, ScienceDirect (2007), www.sciencedirect.com, internet.

Boltromeyuk V.V., Obshchaya khimiya (General Chemistry), Minsk, Vysheyshaya shkola, 2012, p. 65) (translation).

Banker, et al., (1996) Modern Pharmaceuticals, 3rd Edition, Revised and Expanded, p. 596.

Wolff et al., Burger's Medicinal Chemistry and Drug Discovery, 5th Ed. part 1, p. 975-977 (1995).

N.C.B.I.: "qHTS for inhibitors of binding or entry into cells for Marburg Virus," Pubchem Bioassay Record AID 540276, Jul. 2011, 13 pages, XP55641386, Retrieved from the Internet: https://pubchem.ncbi.nlm.nihgov/bioassay/540276.

EP Search Report dated Nov. 19, 2019 from European Patent Appln. No. EP 19183201.3.

"Solvation," Wikipedia, at internet address: https://en.wikipedia.org/wiki/Solvation, web page last edited on Mar. 13, 2019, 6 pages.

Examination Report dated Jan. 7, 2020 from Indian Patent Appln. No. 201727014547.

\* cited by examiner

```
                    SEQUENCE LISTING

<160> NUMBER OF SEQ ID NOS: 6

<210> SEQ ID NO 1
<211> LENGTH: 19
<212> TYPE: DNA
<213> ORGANISM: Dengue virus
<220> FEATURE:
<221> NAME/KEY: source
<222> LOCATION: 1..19
<223> OTHER INFORMATION: /organism="Dengue virus"
      /mol_type="unassigned DNA"

<400> SEQUENCE: 1
cggttagagg agacccctc                                            19

<210> SEQ ID NO 2
<211> LENGTH: 21
<212> TYPE: DNA
<213> ORGANISM: Dengue virus
<220> FEATURE:
```

```
<221> NAME/KEY: source
<222> LOCATION: 1..21
<223> OTHER INFORMATION: /organism="Dengue virus"
      /mol_type="unassigned DNA"

<400> SEQUENCE: 2
gagacagcag gatctctggt c                                              21

<210> SEQ ID NO 3
<211> LENGTH: 28
<212> TYPE: DNA
<213> ORGANISM: Dengue virus
<220> FEATURE:
<221> NAME/KEY: source
<222> LOCATION: 1..28
<223> OTHER INFORMATION: /organism="Dengue virus"
      /mol_type="unassigned DNA"

<400> SEQUENCE: 3
aaggactaga ggttagagga gaccccccc                                      28

<210> SEQ ID NO 4
<211> LENGTH: 18
<212> TYPE: DNA
<213> ORGANISM: Dengue virus
<220> FEATURE:
<221> NAME/KEY: source
<222> LOCATION: 1..18
<223> OTHER INFORMATION: /organism="Dengue virus"
      /mol_type="unassigned DNA"

<400> SEQUENCE: 4
ggccaggtca tcaccatt                                                  18

<210> SEQ ID NO 5
<211> LENGTH: 21
<212> TYPE: DNA
<213> ORGANISM: Dengue virus
<220> FEATURE:
<221> NAME/KEY: source
<222> LOCATION: 1..21
<223> OTHER INFORMATION: /organism="Dengue virus"
      /mol_type="unassigned DNA"

<400> SEQUENCE: 5
atgtccacgt cacacttcat g                                              21

<210> SEQ ID NO 6
<211> LENGTH: 21
<212> TYPE: DNA
<213> ORGANISM: Dengue virus
<220> FEATURE:
<221> NAME/KEY: source
<222> LOCATION: 1..21
<223> OTHER INFORMATION: /organism="Dengue virus"
      /mol_type="unassigned DNA"

<400> SEQUENCE: 6
ttccgctgcc ctgaggctct c                                              21
```

SUBSTITUTED INDOLINE DERIVATIVES AS DENGUE VIRAL REPLICATION INHIBITORS

This application is a national stage application of PCT/EP2017/057661, filed Mar. 31, 2017, which claims priority benefit of Application No. EP16163488.6 filed Apr. 1, 2016. The complete disclosures of the aforementioned related patent applications are hereby incorporated herein by reference for all purposes.

The present invention relates to substituted indoline derivatives, methods to prevent or treat dengue viral infections by using said compounds and also relates to said compounds for use as a medicine, more preferably for use as a medicine to treat or prevent dengue viral infections. The present invention furthermore relates to pharmaceutical compositions or combination preparations of the compounds, to the compositions or preparations for use as a medicine, more preferably for the prevention or treatment of dengue viral infections. The invention also relates to processes for preparation of the compounds.

BACKGROUND OF THE INVENTION

Flaviviruses, which are transmitted by mosquitoes or ticks, cause life-threatening infections in man, such as encephalitis and hemorrhagic fever. Four distinct, but closely related serotypes of the flavivirus dengue are known, so-called DENV-1, -2, -3, and -4. Dengue is endemic in most tropical and sub-tropical regions around the world, predominantly in urban and semi-urban areas. According to the World Health Organization (WHO), 2.5 billion people of which 1 billion children are at risk of DENV infection (WHO, 2002). An estimated 50 to 100 million cases of dengue fever [DF], half a million cases of severe dengue disease (i.e. dengue hemorrhagic fever [DHF] and dengue shock syndrome [DSS]), and more than 20,000 deaths occur worldwide each year. DHF has become a leading cause of hospitalization and death amongst children in endemic regions. Altogether, dengue represents the most common cause of arboviral disease. Because of recent large outbreaks in countries situated in Latin America, South-East Asia and the Western Pacific (including Brazil, Puerto Rico, Venezuela, Cambodia, Indonesia, Vietnam, Thailand), numbers of dengue cases have risen dramatically over the past years. Not only is the number of dengue cases increasing as the disease is spreading to new areas, but the outbreaks tend to be more severe.

Although progress is being made in the development of vaccines against dengue with the availability of the Dengvaxia® vaccine, many difficulties are encountered. These include the existence of a phenomenon referred to as antibody-dependent enhancement (ADE). Recovery from an infection by one serotype provides lifelong immunity against that serotype but confers only partial and transient protection against a subsequent infection by one of the other three serotypes.

Following infection with another serotype, pre-existing heterologous antibodies form complexes with the newly infecting dengue virus serotype but do not neutralize the pathogen. Instead, virus entry into cells is believed to be facilitated, resulting in uncontrolled virus replication and higher peak viral titers. In both primary and secondary infections, higher viral titers are associated with more severe dengue disease. Since maternal antibodies can easily pass on to infants by breast feeding, this might be one of the reasons that children are more affected by severe dengue disease than adults.

In locations with two or more serotypes circulating simultaneously, also referred to as hyper endemic regions, the risk of serious dengue disease is significantly higher due to an increased risk of experiencing a secondary, more severe infection. Moreover, in a situation of hyper-endemicity, the probability of the emergence of more virulent strains is increased, which in turn augments the probability of dengue hemorrhagic fever (DHF) or dengue shock syndrome.

The mosquitoes that carry dengue, including *Aedes aegypti* and *Aedes albopictus* (tiger mosquito), are moving north on the globe. According to the United States (US) Centers for Disease Control and Prevention (CDC), both mosquitoes are currently omnipresent in southern Texas. The spread north of dengue-carrying mosquitoes is not confined to the US, but has also been observed in Europe.

Dengvaxia®, the dengue vaccine produced by Sanofi Pasteur was first approved in Mexico and has received in the meantime approval in more countries. Nevertheless, the vaccine leaves considerable room for improvement due to limited efficacy, especially against DENV-1 and -2, low efficacy in flavivirus-naïve subjects and the lengthy dosing schedule.

Despite these shortcomings, the vaccine is a game changer in endemic settings as it will offer protection to a large part of the population, but likely not to very young infants, who bear the largest burden of dengue. In addition, the dosing schedule and very limited efficacy in flavivirus-naïve subjects make it unsuitable and likely not worthwhile/cost-effective for travelers from non-endemic areas to dengue-endemic areas. The above mentioned shortcomings of the dengue vaccines are the reason why there is a need for a pre-exposure prophylactic dengue antiviral.

Furthermore, today, specific antiviral drugs for the treatment or prevention of dengue fever virus infection are not available. Clearly, there is still a great unmet medical need for therapeutics for the prevention or treatment of viral infections in animals, more in particular in humans and especially for viral infections caused by Flaviviruses, more in particular Dengue virus. Compounds with good anti-viral potency, no or low levels of side-effects, a broad spectrum activity against multiple Dengue virus serotypes, a low toxicity and/or good pharmacokinetic or -dynamic properties are highly needed.

WO-2010/021878 discloses 2-phenylpyrrolidine and indoline derivatives as cold menthol receptor antagonists for treatment of inflammatory and central diseases. WO-2013/045516 discloses indole and indoline derivatives for use in the treatment of dengue viral infections.

The present invention now provides compounds, substituted indoline derivatives, which show high potent activity against all four (4) serotypes of the Dengue virus.

SUMMARY OF THE INVENTION

The present invention is based on the unexpected finding that at least one of the above-mentioned problems can be solved by the current compounds of the invention.

The present invention provides compounds which have been shown to possess potent antiviral activity against all four (4) serotypes currently known. The present invention furthermore demonstrates that these compounds efficiently inhibit proliferation of Dengue virus (DENV). Therefore, these compounds constitute a useful class of potent compounds that can be used in the treatment and/or prevention of viral infections in animals, mammals and humans, more specifically for the treatment and/or prevention of infections with Dengue viruses.

The present invention furthermore relates to the use of such compounds as medicines and to their use for the manufacture of medicaments for treating and/or preventing viral infections, in particular with viruses belonging to the family of the Dengue viruses in animals or mammals, more in particular in humans. The invention also relates to methods for the preparation of all such compounds and to pharmaceutical compositions comprising them in an effective amount.

The present invention also relates to a method of treatment or prevention of dengue viral infections in humans by the administration of an effective amount of one or more such compounds, or a pharmaceutically acceptable salt thereof optionally in combination with one or more other medicines, like another antiviral agent, to a patient in need thereof.

One aspect of the invention is the provision of compounds having formula (I), a stereoisomeric form, a pharmaceutically acceptable salt, solvate or polymorph thereof:

I

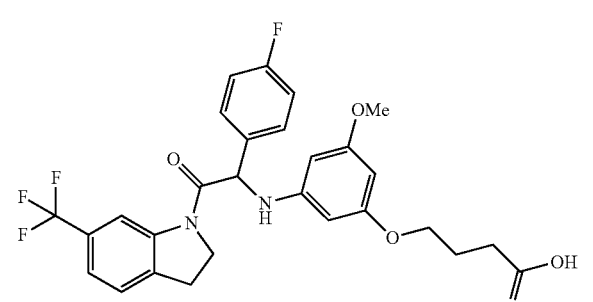

wherein the compounds are selected from the group comprising:

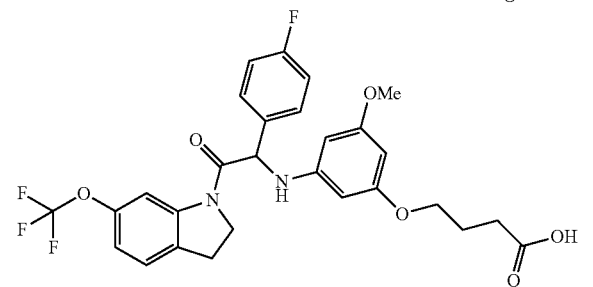

-continued

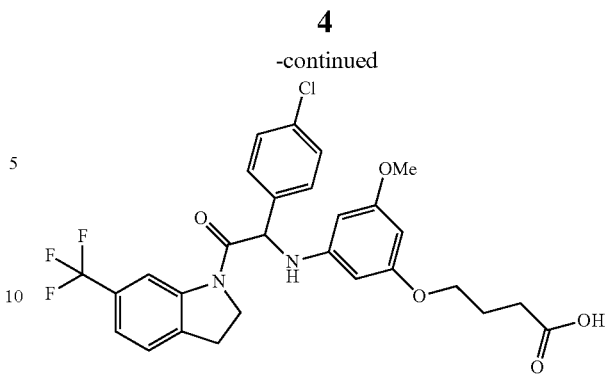

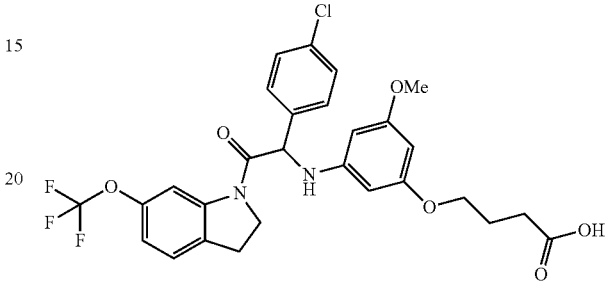

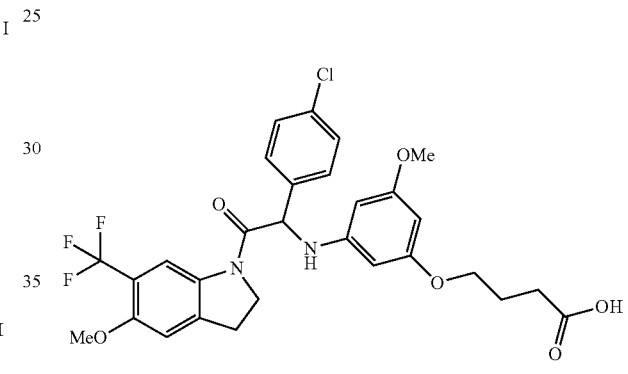

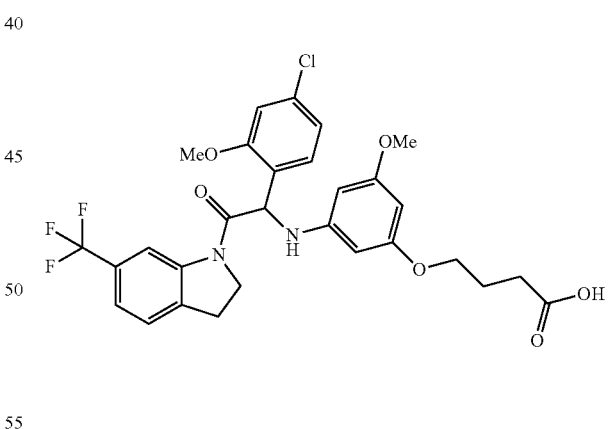

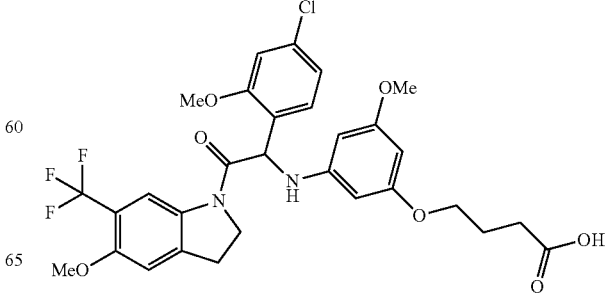

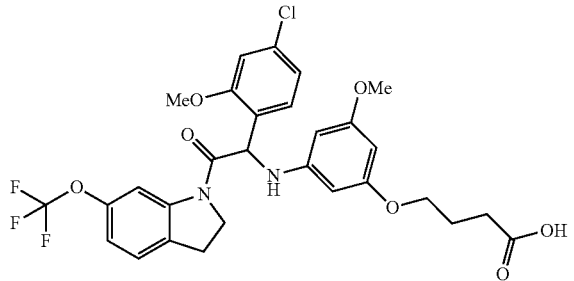

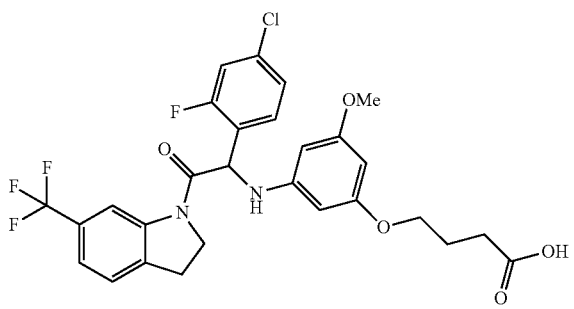

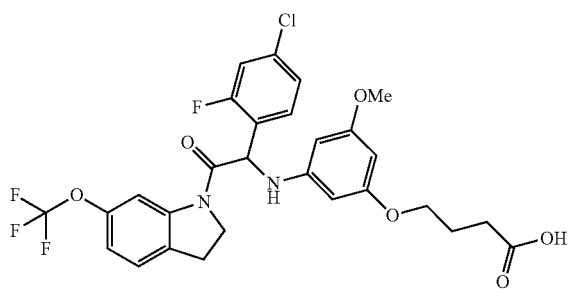

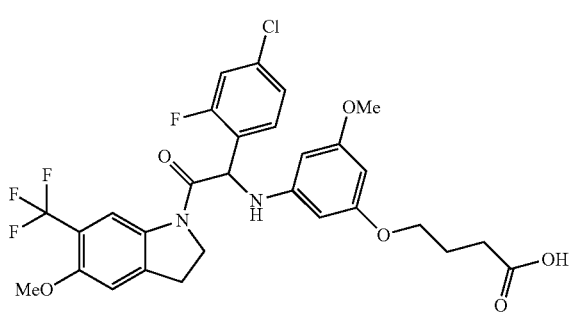

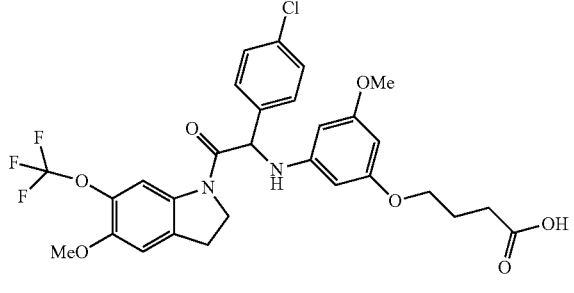

In an alternative embodiment, the present invention relates to a compound having formula (I)

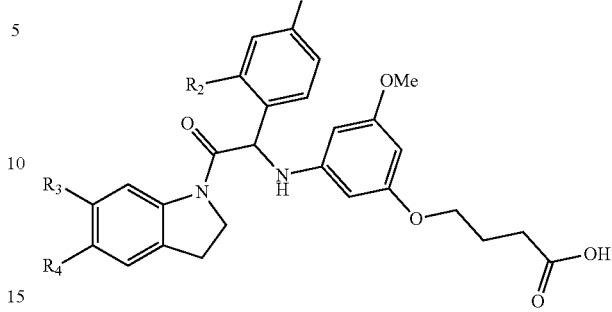

a stereoisomeric form, a pharmaceutically acceptable salt, solvate or polymorph thereof, wherein $R_1$ is fluoro, $R_2$ is hydrogen, $R_3$ is trifluoromethyl, and $R_4$ is hydrogen; or $R_1$ is fluoro, $R_2$ is hydrogen, $R_3$ is trifluoromethoxy, and $R_4$ is hydrogen; or $R_1$ is chloro, $R_2$ is hydrogen, $R_3$ is trifluoromethyl, and $R_4$ is hydrogen; or $R_1$ is chloro, $R_2$ is hydrogen, $R_3$ is trifluoromethoxy, and $R_4$ is hydrogen; or $R_1$ is chloro, $R_2$ is hydrogen, $R_3$ is trifluoromethyl, and $R_4$ is methoxy; or $R_1$ is chloro, $R_2$ is methoxy, $R_3$ is trifluoromethyl, and $R_4$ is hydrogen; or $R_1$ is chloro, $R_2$ is methoxy, $R_3$ is trifluoromethyl, and $R_4$ is methoxy; or $R_1$ is chloro, $R_2$ is methoxy, $R_3$ is trifluoromethoxy, and $R_4$ is hydrogen; or $R_1$ is chloro, $R_2$ is fluoro, $R_3$ is trifluoromethyl, and $R_4$ is hydrogen; or $R_1$ is chloro, $R_2$ is fluoro, $R_3$ is trifluoromethoxy, and $R_4$ is hydrogen; or $R_1$ is chloro, $R_2$ is fluoro, $R_3$ is trifluoromethyl, and $R_4$ is methoxy; or $R_1$ is chloro, $R_2$ is hydrogen, $R_3$ is trifluoromethoxy, and $R_4$ is methoxy.

Part of the current invention is also a pharmaceutical composition comprising a compound mentioned above or a stereoisomeric form, a pharmaceutically acceptable salt, solvate or polymorph thereof together with one or more pharmaceutically acceptable excipients, diluents or carriers.

Pharmaceutically acceptable salts of said compounds include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral or rectal administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of the invention used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

The present disclosure is also intended to include any isotopes of atoms present in the compounds of the invention. For example, isotopes of hydrogen include tritium and deuterium and isotopes of carbon include C-13 and C-14.

The present compounds used in the current invention may also exist in their stereochemically isomeric form, defining all possible compounds made up of the same atoms bonded by the same sequence of bonds but having different three-dimensional structures, which are not interchangeable. Unless otherwise mentioned or indicated, the chemical designation of compounds encompasses the mixture of all possible stereochemically isomeric forms, which said compounds might possess. Said mixture may contain all diastereomers and/or enantiomers of the basic molecular structure of said compound. All stereochemically isomeric forms of the compounds used in the present invention either in pure form or in admixture with each other are intended to be embraced within the scope of the present invention including any racemic mixtures or racemates.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i. e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of compounds and intermediates used in this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The compounds of formula (I) of the present invention all have at least one chiral carbon atom as indicated in the figure below by the carbon atom labelled with *:

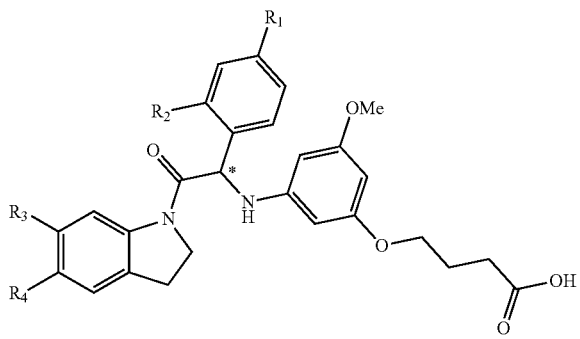

Due to the presence of said chiral carbon atom, a "compound of formula (I)" can be the (R)-enantiomer, the (S)-enantiomer, the racemic form, or any possible combination of the two individual enantiomers in any ratio. When the absolute (R)- or (S)-configuration of an enantiomer is not known, this enantiomer can also be identified by indicating whether the enantiomer is dextrorotatory (+)- or levorotatory (−)-after measuring the specific optical rotation of said particular enantiomer.

In an aspect the present invention relates to a first group of compound of formula (I) wherein the compounds of formula (I) have the (+) specific rotation.

In a further aspect the present invention relates to a second ground of compounds of formula (I) wherein the compounds of formula (I) have the (−) specific rotation.

EXAMPLES

LC/MS Methods

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). For molecules with multiple isotopic patterns (Br, Cl), the reported value is the one obtained for the lowest isotope mass. All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica.

LC/MS Method codes (Flow expressed in mL/min; column temperature (T) in ° C.; Run Time in Minutes)

| Method code | Instrument | Column | Mobile phase | Gradient | Flow Col T | Run time (min) |
|---|---|---|---|---|---|---|
| LC-A | Waters: Acquity® UPLC®-DAD-Quattro Micro™ | Waters: BEH C18 (1.7 μm, 2.1 × 100 mm) | A: 95% CH₃COONH₄ 7 mM/5% CH₃CN, B: CH₃CN | 84.2% A for 0.49 min, to 10.5% A in 2.18 min, held for 1.94 min, back to 84.2% A in 0.73 min, held for 0.73 min. | 0.343 mL/min 40° C. | 6.2 |
| LC-B | Waters: Acquity® H-Class-DAD and SQD2™ | Waters BEH® C18 (1.7 μm, 2.1 × 100 mm) | A: CH₃COONH₄ 7 mM 95%/CH₃CN 5%, B: CH₃CN | 84.2% A/15.8% B to 10.5% A in 2.18 min, held for 1.96 min, back to 84.2% A/15.8% B in 0.73 min, held for 0.49 min. | 0.343 mL/min 40° C. | 6.1 |
| LC-C | Waters: Acquity® UPLC®-DAD-Acquity® TQ detector | Waters: HSS C18 (1.8 μm, 2.1 × 50 mm) | A: 0.1% HCOOH B: CH₃CN | 50% A to 10% A in 3.5 min, held for 1.5 min. | 0.5 mL/min 40° C. | 5 |
| LC-D | Waters: Acquity® UPLC®-DAD-SQD | Waters: BEH C18 (1.7 μm, 2.1 × 50 mm) | A: 10 mM CH₃COONH₄ in 95% H₂O + 5% CH₃CN B: CH₃CN | from 95% A to 5% A in 1.3 min, held for 0.7 min. | 0.8 mL/min 55° C. | 2 |

SFC/MS Methods

The SFC measurement was performed using an Analytical Supercritical fluid chromatography (SFC) system composed by a binary pump for delivering carbon dioxide ($CO_2$) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Analytical SFC/MS Methods (Flow expressed in mL/min; column temperature (T) in ° C.; Run time in minutes, Backpressure (BPR) in bars.

| Method code | column | mobile phase | gradient | Flow Col T | Run time BPR |
| --- | --- | --- | --- | --- | --- |
| SFC-A | Daicel Chiralcel ® OD-3 column (3 µm, 100 × 4.6 mm) | A: $CO_2$ B: iPrOH (+0.3% $iPrNH_2$) | 40% B hold 3 min | 3.5 35 | 3 105 |
| SFC-B | Daicel Chiralcel ® OD-H column (5 µm, 150 × 4.6 mm) | A: $CO_2$ B: MeOH | 40% B hold 7 min | 3 35 | 7 100 |
| SFC-C | Daicel Chiralcel ® OD-H column (5 µm, 150 × 4.6 mm) | A: $CO_2$ B: iPrOH | 40% B hold 7 min | 3 35 | 7 100 |
| SFC-D | Daicel Chiralpak ® AD-H column (5 µm, 150 × 4.6 mm) | A: $CO_2$ B: iPrOH (+0.3% $iPrNH_2$) | 50% B hold 7 min | 3 35 | 7 100 |
| SFC-E | Daicel Chiralcel ® OD-H column (5 µm, 150 × 4.6 mm) | A: $CO_2$ B: EtOH | 30% B hold 7 min | 3 35 | 7 100 |
| SFC-F | Daicel Chiralcel ® OD-H column (5 µm, 150 × 4.6 mm) | A: $CO_2$ B: iPrOH | 30% B hold 7 min | 3 35 | 7 100 |
| SFC-G | Daicel Chiralcel ® OD-H column (3 µm, 150 × 4.6 mm) | A: $CO_2$ B: iPrOH (+0.3% $iPrNH_2$) | 30% B hold 7 min | 3 35 | 7 100 |
| SFC-H | Daicel Chiralpak ® IC column (5 µm, 150 × 4.6 mm) | A: $CO_2$ B: iPrOH (+0.3% $iPrNH_2$) | 30% B hold 7 min | 3 35 | 7 100 |
| SFC-I | Daicel Chiralpak ® AD-3 column (3 µm, 100 × 4.6 mm) | A: $CO_2$ B: iPrOH (+0.3% $iPrNH_2$) | 50% B hold 3 min | 3.5 35 | 3 103 |
| SFC-J | Daicel Chiralpak ® AS3 column (3.0 µm, 150 × 4.6 mm) | A: $CO_2$ B: EtOH (+0.2% $iPrNH_2$ +3% $H_2O$) | 10%-50% B in 6 min, hold 3.5 min | 2.5 40 | 9.5 110 |

Melting Points

Values are either peak values or melt ranges, and are obtained with experimental uncertainties that are commonly associated with this analytical method.

DSC823e (Indicated as DSC)

For a number of compounds, melting points were determined with a DSC823e (Mettler-Toledo). Melting points were measured with a temperature gradient of 10° C./minute. Maximum temperature was 300° C.

Optical Rotations:

Optical rotations were measured on a Perkin-Elmer 341 polarimeter with a sodium lamp and reported as follows: $[\alpha]°$ ($\lambda$, c g/100 ml, solvent, T° C.).

$[\alpha]_\lambda^T = (100a)/(l \times c)$: where l is the path length in dm and c is the concentration in g/100 ml for a sample at a temperature T (° C.) and a wavelength $\lambda$ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 ml).

Example 1: Synthesis of 4-(3-((1-(4-fluorophenyl)-2-oxo-2-(6-(trifluoromethyl)-indolin-1-yl)ethyl)amino)-5-methoxphenoxy)butanoic acid (Compound 1) and Chiral Separation into Enantiomers 1A and 1B

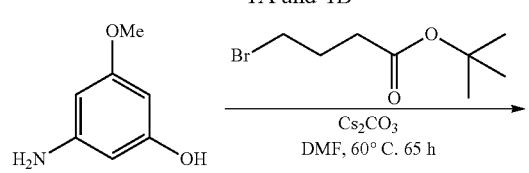

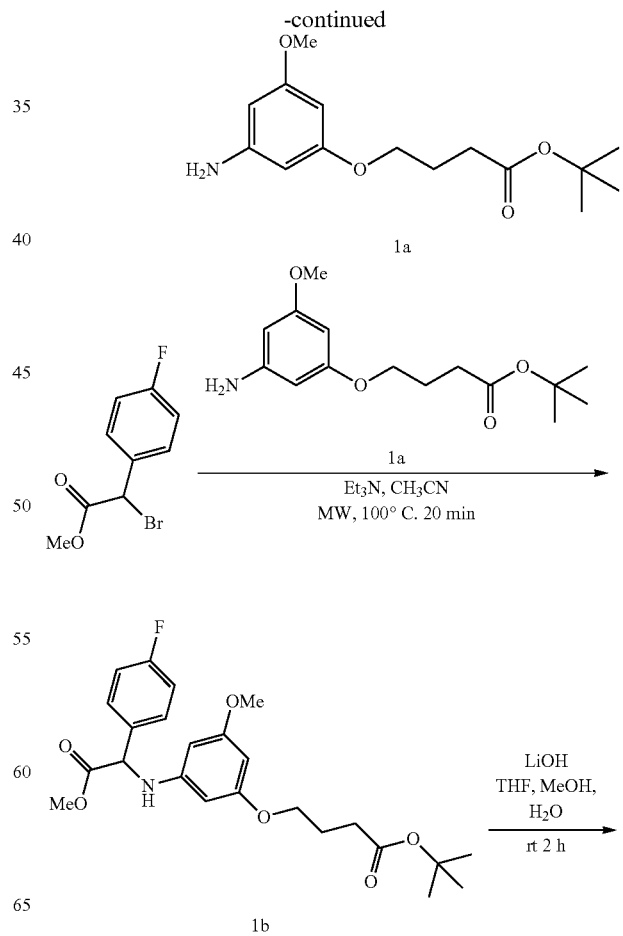

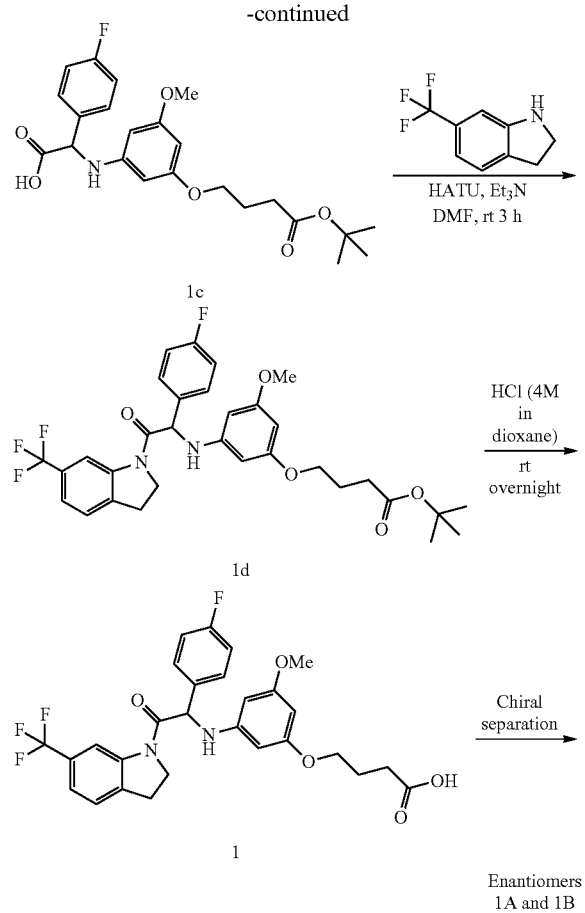

HATU, Et₃N
DMF, rt 3 h

HCl (4M in dioxane)
rt overnight

Chiral separation

Enantiomers 1A and 1B

Synthesis of Intermediate 1a:

To a mechanically stirred solution of tert-butyl 4-bromobutanoate [CAS 110661-91-1] (42.3 g, 0.19 mol) in DMF (600 mL) was added in portions a solid mixture of 3-amino-5-methoxyphenol [CAS 162155-27-3] (26.4 g, 0.19 mol) and Cs₂CO₃ (123.6 g, 0.379 mol). The reaction was stirred at 60° C. for 65 h, and allowed to reach room temperature. The mixture was poured out into H₂O (2.5 L). The product was extracted with Et₂O (2 times). The combined organic layers were washed with brine, dried over MgSO₄ and filtered off. The solvent was evaporated under reduced pressure, and then co-evaporated with toluene. The residue was purified via Normal Phase HPLC (Stationary phase: silica gel 60A 25-40 µm (Merck), Mobile phase: gradient from 20% EtOAc, 80% heptane to 60% EtOAc, 40% heptane) yielding tert-butyl 4-(3-amino-5-methoxyphenoxy)butanoate 1a (27 g).

Synthesis of Intermediate 1b:

A mixture of methyl 2-bromo-2-(4-fluorophenyl)acetate [CAS 71783-54-5] (0.400 g, 1.62 mmol), tert-butyl 4-(3-amino-5-methoxyphenoxy)butanoate 1a (0.547 g, 1.94 mmol) and triethylamine (0.337 mL, 2.43 mmol) in CH₃CN (4 mL) was heated in a microwave oven at 100° C. for 20 min. The reaction mixture was diluted with EtOAc and washed with 1N HCl. The organic phase was washed with H₂O and brine, dried over MgSO₄, filtered and concentrated under reduced pressure. The residue was purified by flash chromatography on silica gel using a gradient of EtOAc (2% to 20%) in heptane to give tert-butyl 4-(3-((1-(4-fluorophenyl)-2-methoxy-2-oxoethyl)amino)-5-methoxyphenoxy)butanoate 1b (0.511 g).

Synthesis of Intermediate 1c:

To a solution of tert-butyl 4-(3-((1-(4-fluorophenyl)-2-methoxy-2-oxoethyl)amino)-5-methoxyphenoxy)butanoate 1b (0.510 g, 1.14 mmol) in a solvent mixture of THF (3 mL), MeOH (3 mL) and H₂O (3 mL) was added lithium hydroxide (0.239 g, 5.70 mmol). The reaction mixture was stirred at room temperature for 2 h. The reaction mixture was partially concentrated under reduced pressure to remove the organic solvents. The residue was acidified with 1N HCl and extracted with CH₂Cl₂. The organic phase was dried over MgSO₄, filtered and concentrated under reduced pressure. The residue was purified by flash chromatography on silica gel using a gradient of MeOH (0% to 10%) in CH₂Cl₂ (containing 2% of acetic acid) to give 2-((3-(4-(tert-butoxy)-4-oxobutoxy)-5-methoxyphenyl)amino)-2-(4-fluoro-phenyl)acetic acid 1c (0.326 g).

Synthesis of Intermediate 1d:

To a solution of 2-((3-(4-(tert-butoxy)-4-oxobutoxy)-5-methoxyphenyl)amino)-2-(4-fluorophenyl)acetic acid 1c (0.326 g, 0.75 mmol) in DMF (6 mL) were added HATU (0.286 g, 0.75 mmol), triethylamine (0.418 mL, 3.01 mmol) and 6-(trifluoromethyl)indoline [CAS 181513-29-1] (0.141 g, 0.75 mmol). The reaction mixture was stirred at room temperature for 3 h. The reaction mixture was diluted with EtOAc and washed with 1N HCl. The organic phase was washed with an aqueous saturated NaHCO₃ solution and brine, dried over MgSO₄, filtered and concentrated under reduced pressure. The residue was purified by flash chromatography on silica gel using a gradient of EtOAc (5% to 50%) in heptane to give tert-butyl 4-(3-((1-(4-fluorophenyl)-2-oxo-2-(6-(trifluoromethyl)indolin-1-yl)ethyl) amino)-5-methoxyphenoxy)butanoate 1d (0.134 g).

Synthesis of Compound 1 and Chiral Separation into Enantiomers 1A and 1B:

To a solution of tert-butyl 4-(3-((1-(4-fluorophenyl)-2-oxo-2-(6-(trifluoromethyl)-indolin-1-yl)ethyl)amino)-5-methoxyphenoxy)butanoate 1d (0.134 g, 0.22 mmol) in CH₂Cl₂ (3 mL) was added a 4M hydrogen chloride solution in dioxane (3 mL, 12 mmol). The reaction mixture was stirred at room temperature overnight. The reaction mixture was concentrated under reduced pressure. The residue was triturated with a mixture of Et₂O/heptane. The solids were filtered off and dried under vacuum to give 4-(3-((1-(4-fluorophenyl)-2-oxo-2-(6-(trifluoromethyl)indolin-1-yl) ethyl)amino)-5-methoxyphenoxy) butanoic acid (Compound 1, 103 mg) as a racemic mixture.

The enantiomers of Compound 1 (1.3 g) were separated via Preparative SFC (Stationary phase: Chiralcel® Diacel OD 20×250 mm, Mobile phase: CO₂, Ethanol). The product fractions were combined and evaporated under reduced pressure. The first eluted enantiomer was further purified by flash chromatography (Stationary phase: Grace Reveleris® silica 40 g, Mobile phase: heptane/EtOAc/EtOH/HOAc gradient 100/0/0/0 to 0/75/24.5/0.5). The desired fractions were combined, evaporated under reduced pressure, and co-evaporated with EtOAc, and then with MeOH/H₂O. The residue was stirred up in H₂O (15 mL)+MeOH (1.5 mL) for 45 minutes, filtered off, washed (4×) with MeOH/H₂O (4/1), and dried under vacuum at 45° C. to provide Enantiomer 1A (475 mg). The second eluted enantiomer was further purified by flash chromatography (Stationary phase: Grace Reveleris® silica 40 g, Mobile phase: heptane/EtOAc/EtOH/ HOAc gradient 100/0/0/0 to 0/75/24.5/0.5). The desired fractions were combined, evaporated under reduced pressure, and co-evaporated with EtOAc, and then with MeOH/H₂O. The residue was stirred up in H₂O (15 mL)+MeOH (1.5 mL) for 75 minutes, filtered off, washed (4×) with MeOH/H₂O (4/1), and dried under vacuum at 45° C. to provide Enantiomer 1B (461 mg).

Compound 1:

¹H NMR (300 MHz, DMSO-d₆) δ ppm 1.80-1.94 (m, 2H) 2.22-2.48 (m, 2H) 3.09-3.27 (m, 2H) 3.62 (s, 3H) 3.85 (t, J=6.2 Hz, 2H) 3.91-4.06 (m, 1H) 4.48-4.61 (m, 1H) 5.57 (d, J=8.7 Hz, 1H) 5.76 (s, 1H) 5.94 (s, 1H) 5.96 (s, 1H) 6.39 (d, J=8.3 Hz, 1H) 7.21 (t, J=8.7 Hz, 2H) 7.35-7.49 (m, 2H) 7.58 (dd, J=8.1, 5.8 Hz, 2H) 8.38 (s, 1H) 12.1 (br. s., 1H)

LC/MS (method LC-C): $R_t$ 1.94 min, MH⁺ 547

Enantiomer 1A:

¹H NMR (400 MHz, DMSO-d₆) δ ppm 1.87 (quin, J=6.8 Hz, 2H) 2.33 (t, J=7.4 Hz, 2H) 3.14-3.29 (m, 2H) 3.62 (s, 3H) 3.85 (t, J=6.5 Hz, 2H) 4.00 (td, J=10.5, 7.3 Hz, 1H) 4.54 (td, J=10.4, 6.3 Hz, 1H) 5.56 (d, J=8.6 Hz, 1H) 5.76 (t, J=2.0 Hz, 1H) 5.95 (dt, J=9.1, 1.8 Hz, 2H) 6.36 (d, J=8.8 Hz, 1H) 7.20 (t, J=8.9 Hz, 2H) 7.34-7.41 (m, 1H) 7.42-7.49 (m, 1H) 7.52-7.62 (m, 2H) 8.38 (br s, 1H) 12.10 (br s, 1H)

LC/MS (method LC-D): $R_t$ 0.99 min, MH⁺ 547

$[\alpha]_D^{20}$: −49.0° (c 0.41, DMF)

Chiral SFC (method SFC-J): $R_t$ 2.92 min, MH⁺ 547 chiral purity 100%.

Enantiomer 1B:

¹H NMR (400 MHz, DMSO-d₆) δ ppm 1.87 (quin, J=6.9 Hz, 2H) 2.33 (t, J=7.3 Hz, 2H) 3.12-3.29 (m, 2H) 3.62 (s, 3H) 3.85 (t, J=6.5 Hz, 2H) 4.00 (td, J=10.4, 7.2 Hz, 1H) 4.54 (td, J=10.4, 6.3 Hz, 1H) 5.56 (d, J=8.8 Hz, 1H) 5.76 (t, J=2.1 Hz, 1H) 5.95 (dt, J=9.1, 2.0 Hz, 2H) 6.36 (d, J=8.8 Hz, 1H) 7.20 (t, J=8.2 Hz, 2H) 7.35-7.41 (m, 1H) 7.42-7.48 (m, 1H) 7.53-7.62 (m, 2H) 8.38 (br s, 1H) 12.11 (br s, 1H)

LC/MS (method LC-D): $R_t$ 1.00 min, MH⁺ 547

$[\alpha]_D^{20}$: +49.5° (c 0.525, DMF)

Chiral SFC (method SFC-J): $R_t$ 2.81 min, MH⁺ 547, chiral purity 100%.

Example 2: Synthesis of 4-(3-((1-(4-fluorophenyl)-2-oxo-2-(6-(trifluoromethoxy)-indolin-1-yl)ethyl)amino)-5-methoxyphenoxy)butanoic Acid (Compound 2) and Chiral Separation into Enantiomers 2A and 2B

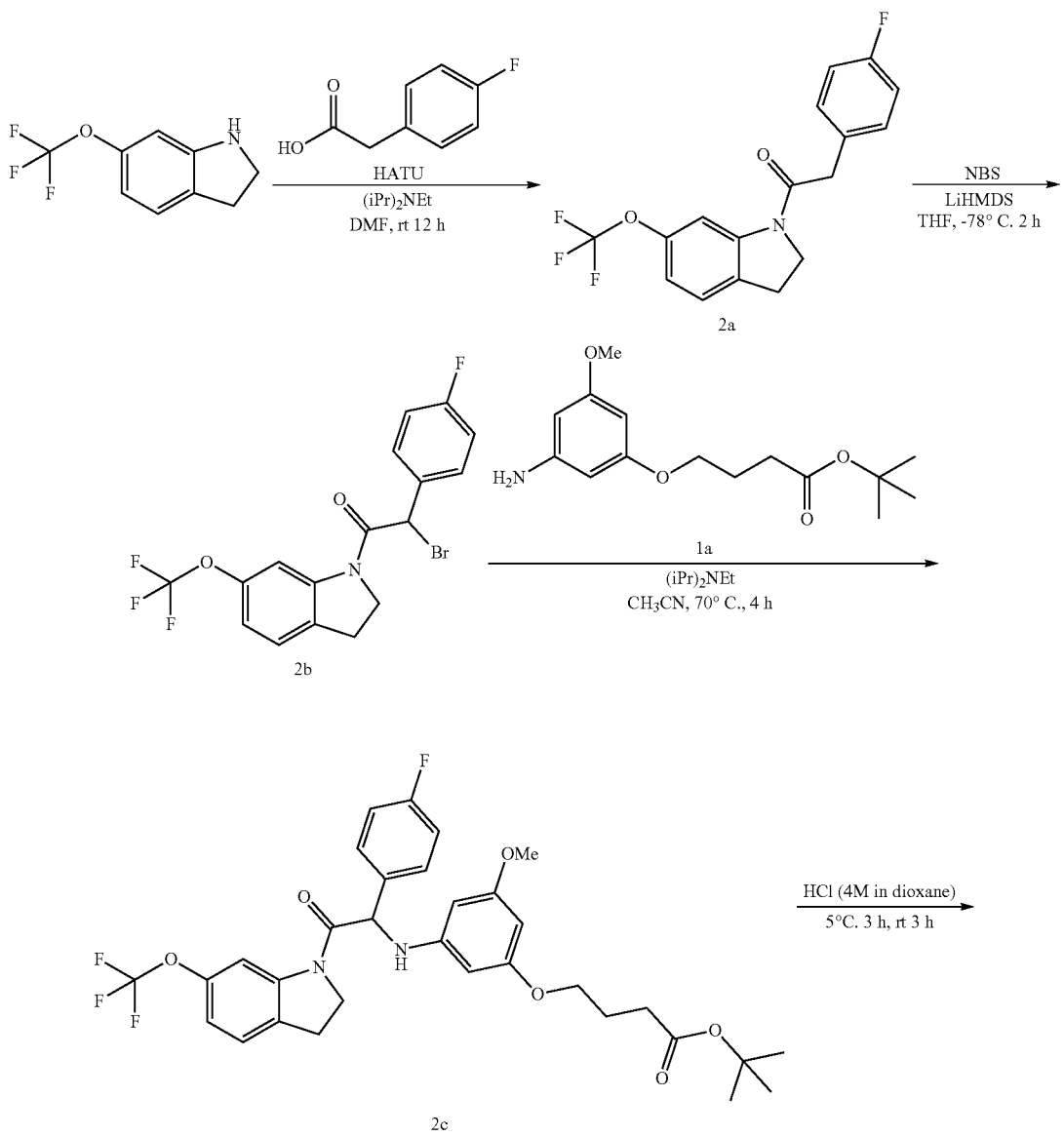

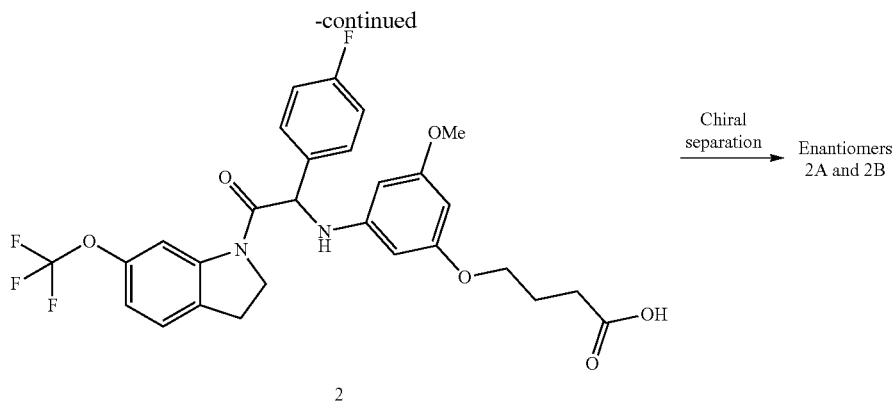

Synthesis of Intermediate 2a:

A mixture of 6-(trifluoromethoxy)indoline [CAS 959235-95-1] (2 g, 9.84 mmol), 2-(4-fluorophenyl)acetic acid [CAS 405-50-5] (1.67 g, 10.8 mmol), HATU (5.6 g, 14.8 mmol) and diisopropylethylamine (4.9 mL, 29.5 mmol) in DMF (40 mL) was stirred at room temperature for 12 h. Water was added and the precipitate was filtered off. The residue was taken up with EtOAc. The organic solution was washed with a 10% aqueous solution of $K_2CO_3$, brine, dried over $MgSO_4$, filtered and the solvent was evaporated under reduced pressure. The residue was purified by chromatography on silica gel (15-40 μm, 80 g, heptane/EtOAc gradient 90/10 to 60/40). The pure fractions were combined and the solvent was concentrated under reduced pressure to give 2-(4-fluorophenyl)-1-(6-(trifluoromethoxy)indolin-1-yl)ethanone 2a (2.5 g).

Synthesis of Intermediate 2b:

At −78° C., under a $N_2$ flow, LiHMDS 1.5 M in THF (9.82 mL, 14.7 mmol) was added dropwise to a mixture of 2-(4-fluorophenyl)-1-(6-(trifluoromethoxy)indolin-1-yl)-ethanone 2a (2.5 g, 7.37 mmol) in THF (40 mL). The mixture was stirred for 15 min at −78° C. and a solution of N-bromosuccinimide (1.44 g, 8.1 mmol) in THF (30 mL) was added dropwise. After stirring for 2 h at −78° C., the reaction was quenched with a saturated aqueous solution of $NH_4Cl$. The mixture was extracted with EtOAc. The organic layer was separated, dried over $MgSO_4$, filtered and the solvent was evaporated under reduced pressure to give, after precipitation from $CH_3CN$/diisopropyl ether, 2-bromo-2-(4-fluorophenyl)-1-(6-(trifluoromethoxy)-indolin-1-yl)ethanone 2b (3 g). The compound was used as such in the next step.

Synthesis of Intermediate 2c:

A mixture of 2-bromo-2-(4-fluorophenyl)-1-(6-(trifluoromethoxy)indolin-1-yl)-ethanone 2b (1.1 g, 2.63 mmol), tert-butyl 4-(3-amino-5-methoxyphenoxy)-butanoate 1a (0.74 g, 2.63 mmol) and diisopropylethylamine (0.54 mL, 3.15 mmol) in $CH_3CN$ (40 mL) was stirred at 70° C. for 4 h. The mixture was concentrated under reduced pressure. The residue was diluted with EtOAc, washed with 1N HCl and water. The organic phase was separated, dried over $MgSO_4$, filtered and the solvent was evaporated under reduced pressure. The compound was purified by flash chromatography on silica gel (15-40 μm, 80 g, heptane/EtOAc 80/20). The pure fractions were combined and evaporated to dryness. The compound was crystallized from diisopropyl ether/petroleum ether, to give tert-butyl 4-(3-((1-(4-fluorophenyl)-2-oxo-2-(6-(trifluoromethoxy)indolin-1-yl)ethyl)amino)-5-methoxy-phenoxy)butanoate 2c (1.25 g).

Synthesis of Compound 2 and Chiral Separation into Enantiomers 2A and 2B:

A solution of tert-butyl 4-(3-((1-(4-fluorophenyl)-2-oxo-2-(6-(trifluoromethoxy)-indolin-1-yl)ethyl)amino)-5-methoxyphenoxy)butanoate 2c (1.5 g, 2.42 mmol) in 4M HCl in dioxane (15 mL) and stirred at 5° C. for 3 h and at room temperature for 3 h. The precipitate was filtered off and dried to afford 4-(3-((1-(4-fluorophenyl)-2-oxo-2-(6-(trifluoromethoxy)indolin-1-yl)ethyl)amino)-5-methoxyphenoxy)butanoic acid as an HCl salt (Compound 2, 1.4 g, 0.76 equiv. HCl, 0.1 equiv. $H_2O$). Compound 2 (HCl salt) was neutralized prior to chiral separation by treatment of a solution of Compound 2 (HCl salt) in EtOAc or $CH_2Cl_2$ with 1N NaOH and evaporation of organic layer under reduced pressure. The enantiomers of Compound 2 (1.3 g) were separated via Preparative Chiral SFC (Stationary phase: Chiralcel® OD-H 5 μm 250×30 mm, Mobile phase: 50% $CO_2$, 50% MeOH) and further purified via reverse phase chromatography (Stationary phase: YMC-actus Triart-C18 10 μm 150×30 mm, Mobile phase: gradient from 60% $HCOONH_4$ 0.6 g/L pH=3.5, 40% $CH_3CN$ to 0% $HCOONH_4$ 0.6 g/L pH=3.5, 100% $CH_3CN$). The product fractions were combined and evaporated under reduced pressure. The first eluted enantiomer (205 mg) was solidified from petroleum ether/diisopropyl ether to give Enantiomer 2A (168 mg). The second eluted enantiomer (259 mg) was solidified from petroleum ether/diisopropyl ether to give Enantiomer 2B (180 mg).

Compound 2:

$^1$H NMR (500 MHz, DMSO-d6) δ ppm 1.87 (quin, J=6.9 Hz, 2H) 2.34 (t, J=7.3 Hz, 2H) 3.05-3.28 (m, 2H) 3.62 (s, 3H) 3.85 (t, J=6.5 Hz, 2H) 4.01 (td, J=10.3, 7.4 Hz, 1H) 4.53 (td, J=10.2, 6.6 Hz, 1H) 5.56 (s, 1H) 5.76 (s, 1H) 5.96 (br d, J=10.4 Hz, 2H) 7.01 (br d, J=7.9 Hz, 1H) 7.21 (t, J=8.8 Hz, 2H) 7.33 (d, J=8.2 Hz, 1H) 7.57 (dd, J=8.5, 5.7 Hz, 2H) 8.04 (s, 1H)

LC/MS (method LC-A): Rt 2.80 min, MH$^+$ 563

Melting point: 136° C.

Enantiomer 2A:

$^1$H NMR (500 MHz, DMSO-d6) δ ppm 1.86 (quin, J=6.9 Hz, 2H) 2.33 (t, J=7.3 Hz, 2H) 3.05-3.26 (m, 2H) 3.61 (s, 3H) 3.84 (t, J=6.3 Hz, 2H) 3.96-4.08 (m, 1H) 4.46-4.60 (m, 1H) 5.55 (d, J=8.8 Hz, 1H) 5.75 (s, 1H) 5.95 (br d, J=11.0 Hz, 2H) 6.41 (br d, J=8.5 Hz, 1H) 7.01 (br d, J=8.2 Hz, 1H) 7.21 (t, J=8.8 Hz, 2H) 7.33 (d, J=8.2 Hz, 1H) 7.57 (dd, J=8.2, 5.7 Hz, 2H) 8.04 (s, 1H) 12.19 (br s, 1H)

LC/MS (method LC-A): R$_t$ 2.87 min, MH$^+$ 563
[α]$_D^{20}$: −46.3° (c 0.27, DMF)
Chiral SFC (method SFC-B): R$_t$ 1.75 min, MH$^+$ 563, chiral purity 100%.
Enantiomer 2B:
$^1$H NMR (500 MHz, DMSO-d6) δ ppm 1.86 (quin, J=6.9 Hz, 2H) 2.32 (t, J=7.3 Hz, 2H) 3.05-3.26 (m, 2H) 3.61 (s, 3H) 3.84 (t, J=6.5 Hz, 2H) 4.01 (td, J=10.3, 7.4 Hz, 1H) 4.53 (td, J=10.2, 6.0 Hz, 1H) 5.55 (d, J=8.8 Hz, 1H) 5.75 (s, 1H) 5.95 (br d, J=12.0 Hz, 2H) 6.41 (d, J=8.8 Hz, 1H) 7.01 (br d, J=7.9 Hz, 1H) 7.20 (t, J=8.7 Hz, 2H) 7.33 (d, J=8.2 Hz, 1H) 7.57 (dd, J=8.5, 5.7 Hz, 2H) 8.04 (s, 1H) 11.49-12.49 (m, 1H)

LC/MS (method LC-A): R$_t$ 2.87 min, MH$^+$ 563
[α]$_D^{20}$: +47.0° (c 0.27, DMF)
Chiral SFC (method SFC-B): R$_t$ 3.83 min, MH$^+$ 563, chiral purity 100%.

Example 3: Synthesis of 4-(3-((1-(4-chlorophenyl)-2-oxo-2-(6-(trifluoromethyl)-indolin-1-yl)ethyl)amino)-5-methoxyphenoxy)butanoic Acid (Compound 3) and Chiral Separation into Enantiomers 3A and 3B

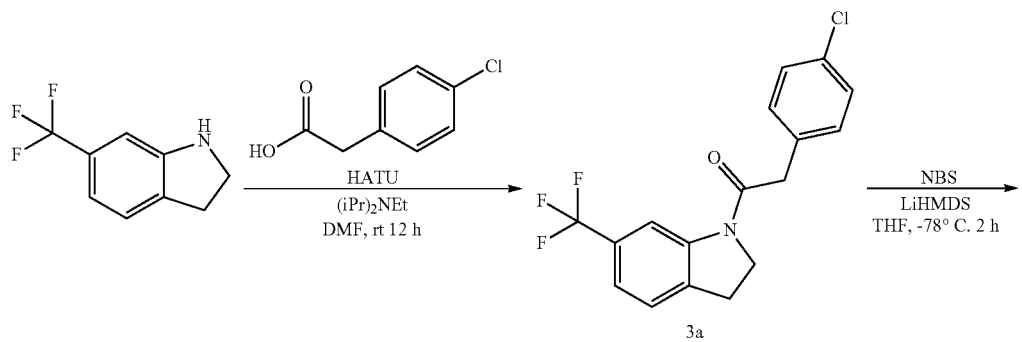

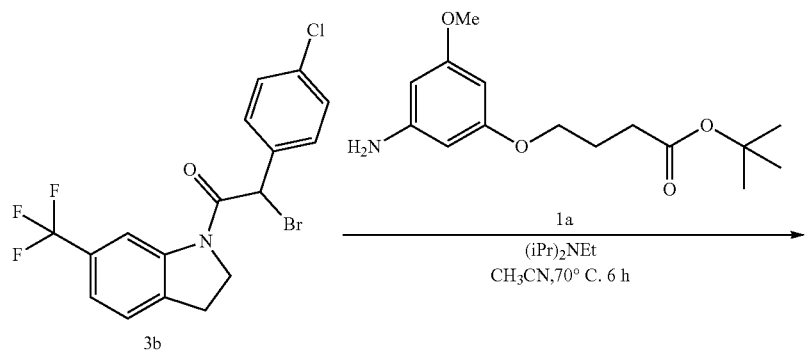

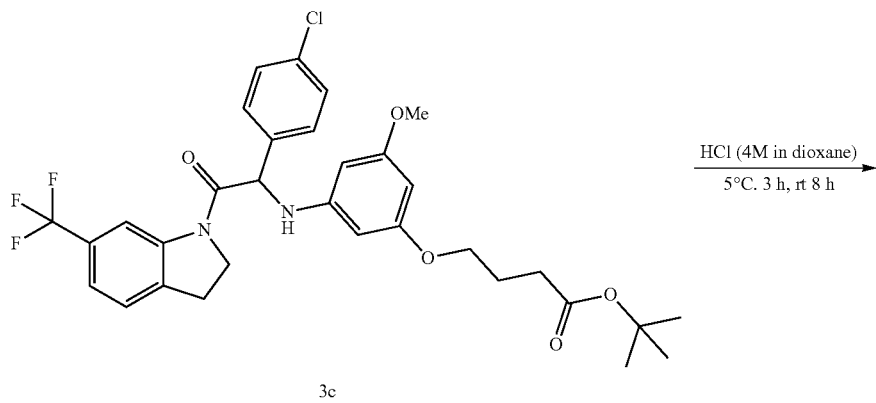

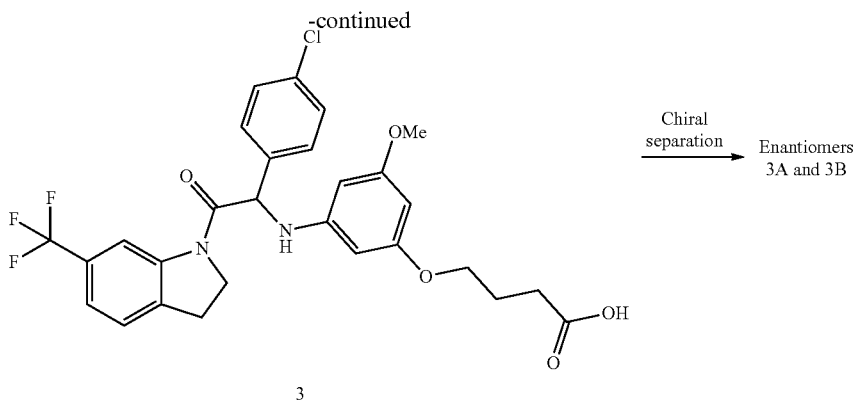

Synthesis of Intermediate 3a:

A mixture of 6-(trifluoromethyl)indoline [CAS 181513-29-1] (3 g, 16.0 mmol), 2-(4-chlorophenyl)acetic acid [CAS 1878-66-6] (3.53 g, 20.8 mmol), HATU (9.1 g, 24.0 mmol) and diisopropylethylamine (7.95 mL, 48.1 mmol) in DMF (75 mL) was stirred at room temperature for 12 h. Water was added and the precipitate was filtered off. The residue was taken up with EtOAc. The organic solution was washed with a 10% aqueous solution of $K_2CO_3$, brine, dried over $MgSO_4$, filtered and the solvent was evaporated under reduced pressure. The residue was purified by chromatography on silica gel (15-40 μm, 80 g, heptane/EtOAc gradient 90/10 to 60/40). The pure fractions were combined and the solvent was concentrated under reduced pressure to give 2-(4-chlorophenyl)-1-(6-(trifluoromethyl)indolin-1-yl)-ethanone 3a (4.5 g).

Synthesis of Intermediate 3b:

At −78° C., under a $N_2$ flow, LiHMDS 1.5 M in THF (17.7 mL, 26.5 mmol) was added dropwise to a mixture of 2-(4-chlorophenyl)-1-(6-(trifluoromethyl)indolin-1-yl)-ethanone 3a (4.5 g, 13.3 mmol) in THF (65 mL). The mixture was stirred for 15 min at −78° C. and a solution of N-bromosuccinimide (2.6 g, 14.6 mmol) in THF (35 mL) was added dropwise. After stirring for 2 h at −78° C., the reaction was quenched with a saturated solution of $NH_4Cl$. The mixture was extracted with EtOAc. The organic layer was separated, dried over $MgSO_4$, filtered and the solvent was evaporated under reduced pressure. The residue was taken up with diisopropyl ether. The precipitate was filtered off and discarded (residual succinimide). The filtrate was concentrated under reduced pressure to give 2-bromo-2-(4-chlorophenyl)-1-(6-(trifluoromethyl)indolin-1-yl)ethanone 3b (5 g). The compound was used as such in the next step.

Synthesis of Intermediate 3c:

A mixture of 2-bromo-2-(4-chlorophenyl)-1-(6-(trifluoromethyl)indolin-1-yl)ethanone 3b (5 g, 11.9 mmol), tert-butyl 4-(3-amino-5-methoxyphenoxy)butanoate 1a (3.3 g, 11.9 mmol) and diisopropylethylamine (2.47 mL, 14.3 mmol) in $CH_3CN$ (120 mL) was stirred at 70° C. for 6 h. The mixture was concentrated under reduced pressure, diluted with EtOAc, and washed with 1N HCl and water. The organic phase was separated, dried over $MgSO_4$, filtered and the solvent was evaporated under reduced pressure. The compound was purified by flash chromatography on silica gel (15-40 μm, 80 g, heptane/EtOAc gradient 90/10 to 60/40). The pure fractions were combined and evaporated to dryness to give tert-butyl 4-(3-((1-(4-chloro-phenyl)-2-oxo-2-(6-(trifluoromethyl)indolin-1-yl)ethyl)amino)-5-methoxyphenoxy)-butanoate 3c (1.6 g).

Synthesis of Compound 3 and Chiral Separation into Enantiomers 3A and 3B:

A solution of tert-butyl 4-(3-((1-(4-chlorophenyl)-2-oxo-2-(6-(trifluoromethyl)indolin-1-yl)ethyl)amino)-5-methoxyphenoxy)butanoate 3c (1.6 g, 2.58 mmol) in 4M HCl in dioxane (22 mL) was stirred at 5° C. for 3 h and at room temperature for 8 h. The solution was concentrated under reduced pressure. The residue was taken up in $CH_3CN$/diisopropyl ether. The precipitate was filtered off and dried to afford 4-(3-((1-(4-chlorophenyl)-2-oxo-2-(6-(trifluoromethyl)indolin-1-yl)ethyl)amino)-5-methoxyphenoxy)butanoic acid as an HCl salt (1.15 g, 0.95 equiv. HCl, 0.07 equiv. $H_2O$). A minor part of the Compound 3 (HCl salt) was neutralized by treatment of a solution of Compound 3 (HCl salt) in EtOAc or $CH_2Cl_2$ with 1N NaOH and evaporation of organic layer under reduced pressure to give Compound 3. The remaining amount of Compound 3 (HCl salt) was used for the chiral separation: the enantiomers were separated via Preparative Chiral SFC (Stationary phase: Chiralcel® OD-H 5 μm 250×30 mm, Mobile phase: 50% $CO_2$, 50% iPrOH). The first eluted enantiomer (470 mg) was solidified from petroleum ether/diisopropyl ether to give Enantiomer 3A (404 mg). The second eluted enantiomer (480 mg) was solidified from petroleum ether/diisopropyl ether to give Enantiomer 3B (433 mg).

Compound 3:

$^1$H NMR (500 MHz, DMSO-d6) δ ppm 1.87 (quin, J=6.8 Hz, 2H) 2.33 (t, J=7.3 Hz, 2H) 3.18-3.27 (m, 2H) 3.62 (s, 3H) 3.85 (t, J=6.3 Hz, 2H) 3.97-4.09 (m, 1H) 4.46-4.59 (m, 1H) 5.57 (d, J=8.6 Hz, 1H) 5.76 (s, 1H) 5.95 (br d, J=9.1 Hz, 2H) 6.40 (br d, J=8.6 Hz, 1H) 7.34-7.49 (m, 4H) 7.55 (d, J=8.6 Hz, 2H) 8.38 (s, 1H) 11.90-12.25 (m, 1H)

LC/MS (method LC-A): Rt 2.88 min, MH+ 563

Melting point: 192° C.

Enantiomer 3A:

$^1$H NMR (500 MHz, DMSO-d6) δ ppm 1.87 (br t, J=6.6 Hz, 2H) 2.34 (br t, J=7.1 Hz, 2H) 3.15-3.31 (m, 2H) 3.62 (s, 3H) 3.85 (br t, J=6.1 Hz, 2H) 3.97-4.09 (m, 1H) 4.48-4.60 (m, 1H) 5.59 (br d, J=8.5 Hz, 1H) 5.77 (br s, 1H) 5.95 (br d, J=11.3 Hz, 2H) 6.44 (br d, J=8.5 Hz, 1H) 7.36-7.50 (m, 4H) 7.56 (br d, J=8.2 Hz, 2H) 8.38 (s, 1H) 12.17 (br s, 1H)

LC/MS (method LC-A): $R_t$ 2.93 min, MH+ 563

$[α]_D^{20}$: −42.4° (c 0.25, DMF)

Chiral SFC (method SFC-C): $R_t$ 2.12 min, MH+ 563, chiral purity 100%.

Enantiomer 3B:

$^1$H NMR (500 MHz, DMSO-d6) δ ppm 1.87 (quin, J=6.7 Hz, 2H) 2.34 (br t, J=7.1 Hz, 2H) 3.15-3.31 (m, 2H) 3.62 (s, 3H) 3.85 (br t, J=6.3 Hz, 2H) 3.97-4.10 (m, 1H) 4.49-4.61 (m, 1H) 5.59 (br d, J=8.8 Hz, 1H) 5.77 (s, 1H) 5.95 (br d, J=11.3 Hz, 2H) 6.44 (br d, J=8.5 Hz, 1H) 7.36-7.49 (m, 4H) 7.56 (br d, J=8.2 Hz, 2H) 8.38 (s, 1H) 12.17 (br s, 1H LC/MS (method LC-A): $R_t$ 2.93 min, MH$^+$ 563
$[\alpha]_D^{20}$: +50.7° (c 0.27, DMF)
Chiral SFC (method SFC-C): $R_t$ 4.87 min, MH$^+$ 563, chiral purity 100%.
Example 4: Synthesis of 4-(3-((1-(4-chlorophenyl)-2-oxo-2-(6-(trifluoromethoxy)-indolin-1-yl)ethyl)amino)-5-methoxyphenoxy)butanoic Acid (Compound 4) and Chiral Separation into Enantiomers 4A and 4B
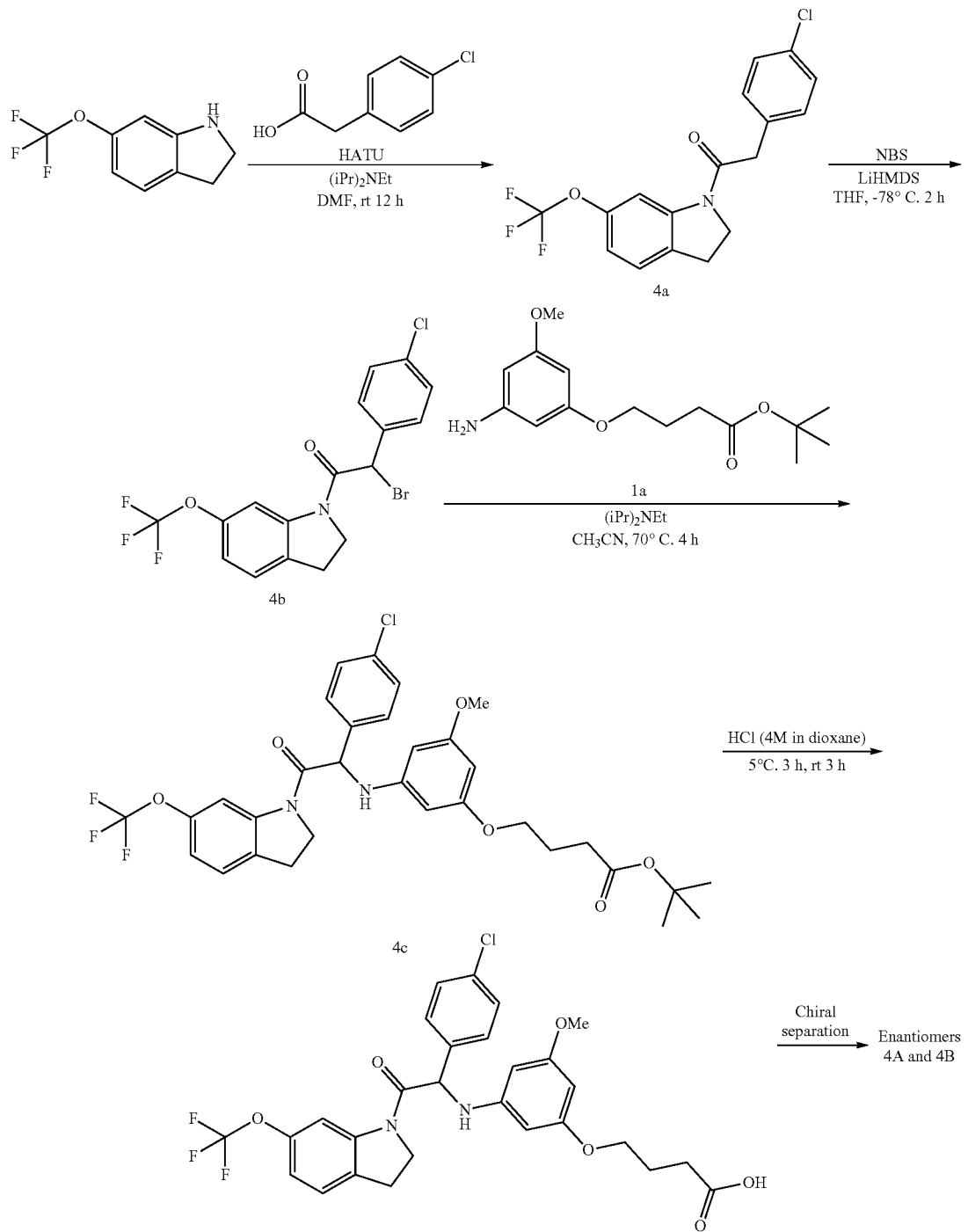

Synthesis of Intermediate 4a:

A mixture of 6-(trifluoromethoxy)indoline [CAS 959235-95-1] (2 g, 9.84 mmol), 2-(4-chlorophenyl)acetic acid [CAS 1878-66-6] (1.85 g, 10.8 mmol), HATU (5.6 g, 14.8 mmol) and diisopropylethylamine (4.9 mL, 29.5 mmol) in DMF (40 mL) was stirred at room temperature for 12 h. Water was added and the precipitate was filtered off. The residue was taken up with EtOAc. The organic solution was washed with a 10% aqueous solution of $K_2CO_3$, brine, dried over $MgSO_4$, filtered and the solvent was evaporated under reduced pressure. The residue was purified by chromatography on silica gel (15-40 µm, 80 g, heptane/EtOAc gradient 90/10 to 60/40). The pure fractions were combined and the solvent was concentrated under reduced pressure to give 2-(4-chlorophenyl)-1-(6-(trifluoromethoxy)indolin-1-yl)-ethanone 4a (3 g).

Synthesis of Intermediate 4b:

At −78° C., under $N_2$ flow, LiHMDS 1.5 M in THF (11.2 mL, 16.9 mmol) was added dropwise to a mixture of 2-(4-chlorophenyl)-1-(6-(trifluoromethoxy)indolin-1-yl)-ethanone 4a (3 g, 8.43 mmol) in THF (50 mL). The mixture was stirred for 15 min at −78° C. and a solution of N-bromosuccinimide (1.65 g, 9.3 mmol) in THF (30 mL) was added dropwise. After stirring for 2 h at −78° C., the reaction was quenched with a saturated solution of $NH_4Cl$. The mixture was extracted with EtOAc. The organic layer was separated, dried over $MgSO_4$, filtered and the solvent was evaporated under reduced pressure to give 2-bromo-2-(4-chlorophenyl)-1-(6-(trifluoromethoxy)indolin-1-yl)ethanone 4b (3.6 g). The compound was used as such in the next step.

Synthesis of Intermediate 4c:

A mixture of 2-bromo-2-(4-chlorophenyl)-1-(6-(trifluoromethoxy)indolin-1-yl)-ethanone 4b (3.6 g, 8.3 mmol), tert-butyl 4-(3-amino-5-methoxyphenoxy)-butanoate 1a (2.3 g, 8.3 mmol) and diisopropylethylamine (1.7 mL, 9.94 mmol) in $CH_3CN$ (80 mL) was stirred at 70° C. for 4 h. The mixture was concentrated under reduced pressure, diluted with EtOAc, and washed with 1N HCl and water. The organic phase was separated, dried over $MgSO_4$, filtered and the solvent was evaporated under reduced pressure. The compound was purified by flash chromatography on silica gel (15-40 µm, 120 g, heptane/EtOAc 80/20). The pure fractions were combined and evaporated to dryness to give, after crystallization from diisopropyl ether, tert-butyl 4-(3-((1-(4-chlorophenyl)-2-oxo-2-(6-(trifluoro-methoxy)indolin-1-yl)ethyl)amino)-5-methoxyphenoxy)butanoate 4c (2.6 g).

Synthesis of Compound 4 and Chiral Separation into Enantiomers 4A and 4B:

A solution of tert-butyl 4-(3-((1-(4-chlorophenyl)-2-oxo-2-(6-(trifluoromethoxy)-indolin-1-yl)ethyl)amino)-5-methoxyphenoxy)butanoate 4c (2.4 g, 3.8 mmol) in 4M HCl in dioxane (24 mL) was stirred at 5° C. for 3 h and at room temperature for 3 h. The precipitate was filtered off and dried to afford 4-(3-((1-(4-chlorophenyl)-2-oxo-2-(6-(trifluoromethoxy)indolin-1-yl)ethyl)amino)-5-methoxyphenoxy) butanoic acid as an HCl salt (Compound 4, 2 g, 0.8 equiv. HCl, 0.07 equiv. $H_2O$). Compound 4 (2 g, HCl salt) was neutralized prior to chiral separation by treatment of a solution of Compound 4 (HCl salt) in ethylacetate with 1N NaOH and evaporation of the organic layer under reduced pressure. The enantiomers were separated via Preparative Chiral SFC (Stationary phase: Chiralcel® OD-H 5 µm 250×30 mm, Mobile phase: 50% $CO_2$, 50% iPrOH (+0.3% $iPrNH_2$)) and further purified via Preparative achiral SFC (Stationary phase: Cyano® 6 µm 150×21.2 mm, Mobile phase: 80% $CO_2$, 20% MeOH (+0.3% $iPrNH_2$)). The product fractions were combined and evaporated under reduced pressure. The two enantiomers were taken up with EtOAc and washed with 1N HCl. The organic layers were separated, dried over $MgSO_4$, filtered and the solvent was evaporated under reduced pressure. The first eluted enantiomer was solidified from ether/diisopropyl ether to give Enantiomer 4A (616 mg). The second eluted enantiomer was solidified from ether/diisopropyl ether to give Enantiomer 4B (715 mg).

It is also possible to separate the enantiomers starting from the HCl salt of the racemate using the same conditions for chiral separation.

Compound 4:

$^1$H NMR (500 MHz, DMSO-d6) δ ppm 1.87 (quin, J=6.9 Hz, 2H) 2.34 (t, J=7.3 Hz, 2H) 3.07-3.28 (m, 2H) 3.62 (s, 3H) 3.85 (t, J=6.5 Hz, 2H) 4.04 (td, J=10.5, 7.1 Hz, 1H) 4.52 (td, J=10.3, 6.5 Hz, 1H) 5.57 (s, 1H) 5.76 (t, J=2.2 Hz, 1H) 5.90-6.00 (m, 2H) 7.01 (dd, J=8.2, 1.6 Hz, 1H) 7.33 (d, J=8.2 Hz, 1H) 7.41-7.48 (m, 2H) 7.55 (d, J=8.5 Hz, 2H) 8.03 (s, 1H)

LC/MS (method LC-B): Rt 2.70 min, $MH^+$ 579

Melting point: 150° C.

Enantiomer 4A:

$^1$H NMR (500 MHz, DMSO-d6) δ ppm 1.87 (quin, J=6.7 Hz, 2H) 2.34 (br t, J=7.3 Hz, 2H) 3.08-3.27 (m, 2H) 3.62 (s, 3H) 3.85 (br t, J=6.3 Hz, 2H) 3.99-4.11 (m, 1H) 4.47-4.57 (m, 1H) 5.57 (br s, 1H) 5.76 (s, 1H) 5.95 (br d, J=10.1 Hz, 2H) 6.45 (br s, 1H) 7.01 (br d, J=7.6 Hz, 1H) 7.34 (br d, J=7.9 Hz, 1H) 7.44 (br d, J=8.5 Hz, 2H) 7.55 (br d, J=8.2 Hz, 2H) 8.04 (br s, 1H) 12.12 (br s, 1H)

LC/MS (method LC-A): $R_t$ 2.95 min, $MH^+$ 579

$[α]_D^{20}$: −48.5° (c 0.27, DMF)

Chiral SFC (method SFC-A): $R_t$ 1.13 min, $MH^+$ 579, chiral purity 100%.

Enantiomer 4B:

$^1$H NMR (500 MHz, DMSO-d6) δ ppm 1.87 (br t, J=6.8 Hz, 2H) 2.34 (br t, J=7.3 Hz, 2H) 3.09-3.27 (m, 2H) 3.62 (s, 3H) 3.85 (br t, J=6.1 Hz, 2H) 3.99-4.10 (m, 1H) 4.46-4.59 (m, 1H) 5.57 (s, 1H) 5.76 (br s, 1H) 5.95 (br d, J=10.1 Hz, 2H) 6.45 (br s, 1H) 7.01 (br d, J=7.9 Hz, 1H) 7.34 (br d, J=7.9 Hz, 1H) 7.44 (br d, J=8.2 Hz, 2H) 7.55 (br d, J=8.2 Hz, 2H) 8.04 (br s, 1H) 12.12 (br s, 1H)

LC/MS (method LC-A): $R_t$ 2.94 min, $MH^+$ 579

$[α]_D^{20}$: +42.9° (c 0.28, DMF)

Chiral SFC (method SFC-A): $R_t$ 2.13 min, $MH^+$ 579, chiral purity 100%.

Example 5: Synthesis of 4-(3-((1-(4-chlorophenyl)-2-(5-methoxy-6-(trifluoromethyl)indolin-1-yl)-2-oxoethyl)amino)-5-methoxyphenoxy)butanoic Acid (Compound 5) and Chiral Separation into Enantiomers 5A and 5B
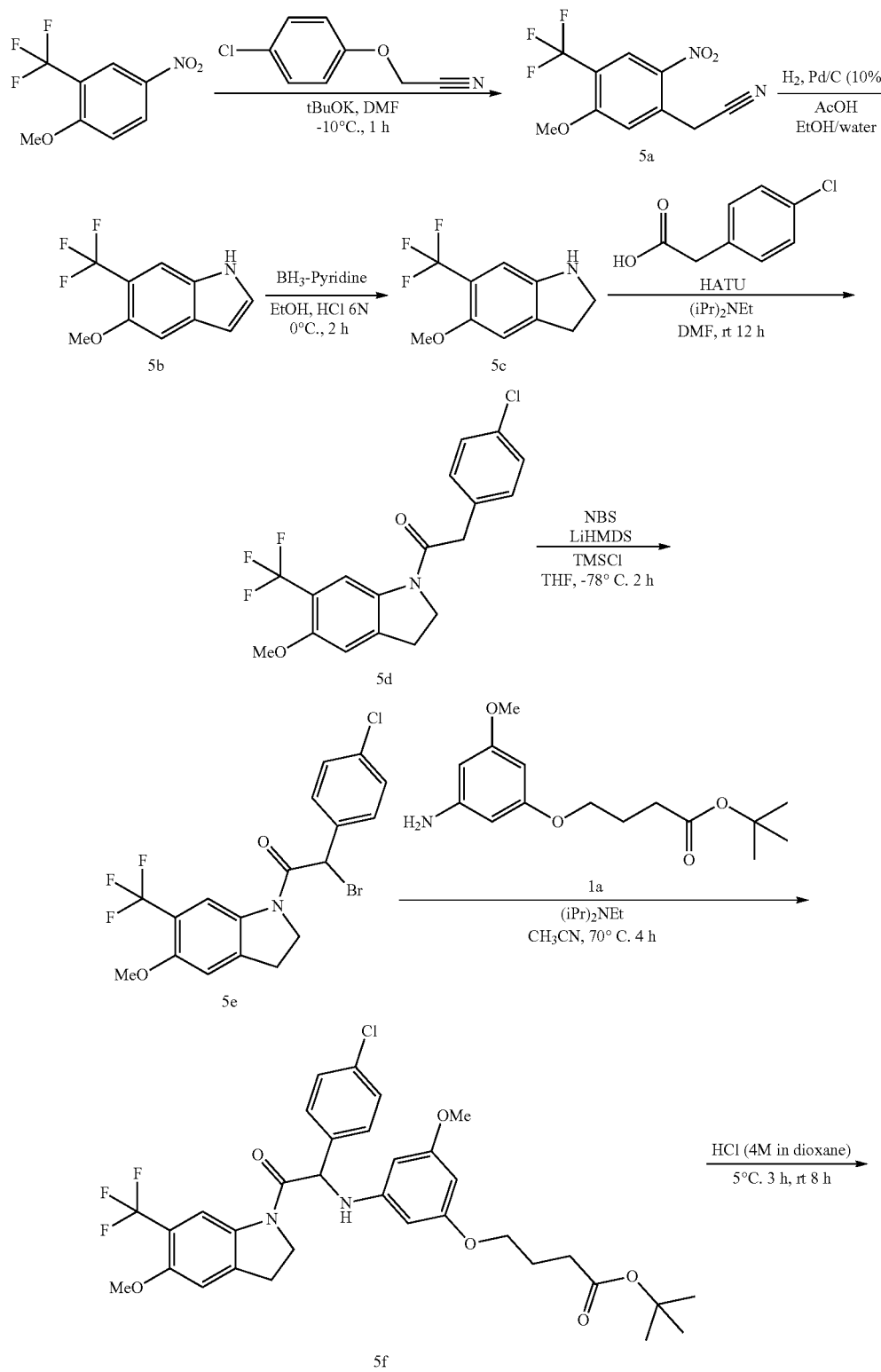

-continued

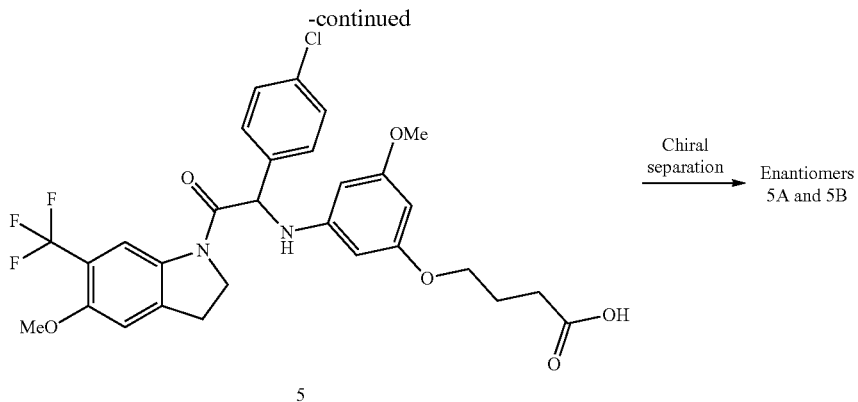

5

Synthesis of Intermediate 5a:

A mixture of 1-methoxy-4-nitro-2-(trifluoromethyl)benzene [CAS 654-76-2] (24.5 g, 110.8 mmol) and 4-chlorophenoxyacetonitrile [CAS 3598-13-8] (20.4 g, 121.9 mmol) in DMF (100 mL) was added dropwise over 30 min to a stirred solution of tBuOK (27.35 g, 243.7 mmol) in DMF (100 mL) at −10° C. After addition, the purple solution was maintained at −10° C. for 1 h. 500 mL of ice-water and 500 mL of 6N HCl were added and the precipitate was filtered off, washed with water and dried under reduced pressure to afford 40.4 g of 2-(5-methoxy-2-nitro-4-(trifluoromethyl)phenyl)acetonitrile 5a (used as such in the next step).

Synthesis of Intermediate 5b:

A solution of 2-(5-methoxy-2-nitro-4-(trifluoromethyl)phenyl)acetonitrile 5a (26 g, 99.9 mmol) in ethanol/water (9/1) (500 mL) and AcOH (5.2 mL) was hydrogenated for 1 h at a pressure of 3.5 Bar with 10% Pd/C (15.3 g) as the catalyst. The reaction mixture was filtered through a pad of Celite® and the filter cake was washed with a solvent mixture of $CH_2Cl_2$ and $CH_3OH$. The filtrate was concentrated under reduced pressure. The residue was filtered through a glass filter charged with silica 60-200 μm using heptane/EtOAc 80/20 as the eluent. The fractions containing the expected compound were combined and the solvent was concentrated under reduced pressure to give 5-methoxy-6-(trifluoromethyl)-1H-indole 5b (15.6 g).

Synthesis of Intermediate 5c:

At 0° C., $BH_3$—Pyridine (23.5 mL, 232.4 mmol) was added dropwise to a solution of 5-methoxy-6-(trifluoromethyl)-1H-indole 5b (10 g, 46.5 mmol) in EtOH (60 mL). 6N HCl (140 mL) was slowly added while maintaining the temperature below 10° C. The mixture was stirred at 0° C. for 2 h. Water (200 mL) was added and the mixture was basified to pH 8-9 with a concentrated aqueous solution of NaOH (the reaction temperature was kept below 20° C.). The precipitate was filtered off, washed with water (twice) and co-evaporated under reduced pressure with toluene to give 5-methoxy-6-(trifluoromethyl)indoline 5c (9 g).

Synthesis of Intermediate 5d:

A mixture of 5-methoxy-6-(trifluoromethyl)indoline 5c (2 g, 9.21 mmol), 2-(4-chloro-phenyl)acetic acid [CAS 1878-66-6] (1.73 g, 10.1 mmol), HATU (5.25 g, 13.8 mmol) and diisopropylethylamine (4.6 mL, 27.6 mmol) in DMF (40 mL) was stirred at room temperature for 12 h. Water was added and the precipitate was filtered off. The residue was taken up with EtOAc. The organic solution was washed with a 10% aqueous solution of $K_2CO_3$, brine, dried over $MgSO_4$, filtered and the solvent was evaporated under reduced pressure. The residue was purified by chromatography on silica gel (15-40 μm, 80 g, heptane/EtOAc gradient 90/10 to 60/40). The pure fractions were combined and the solvent was concentrated under reduced pressure to give 2-(4-chlorophenyl)-1-(5-methoxy-6-(trifluoromethyl)indolin-1-yl)-ethanone 5d (3 g).

Synthesis of Intermediate 5e:

At −78° C., under $N_2$ flow, LiHMDS 1 M in THF (17.3 mL, 17.3 mmol) was added dropwise to a mixture of 2-(4-chlorophenyl)-1-(5-methoxy-6-(trifluoromethyl)-indolin-1-yl)ethanone 5d (3.2 g, 8.65 mmol) in THF (45 mL). TMSCI (1.32 mL, 10.4 mmol) was added dropwise. The mixture was stirred for 15 min at −78° C. and a solution of N-bromosuccinimide (1.85 g, 10.4 mmol) in THF (30 mL) was added dropwise. After stirring for 2 h at −78° C., the reaction was quenched with a saturated solution of $NH_4Cl$. The mixture was extracted with EtOAc. The organic layer was separated, dried over $MgSO_4$, filtered and the solvent was evaporated under reduced pressure to give 2-bromo-2-(4-chlorophenyl)-1-(5-methoxy-6-(trifluoromethyl)indolin-1-yl)ethanone 5e (3.1 g). The compound was used as such in the next step.

Synthesis of Intermediate 5f:

A mixture of 2-bromo-2-(4-chlorophenyl)-1-(5-methoxy-6-(trifluoromethyl)indolin-1-yl)ethanone 5e (3.5 g, 7.8 mmol), tert-butyl 4-(3-amino-5-methoxyphenoxy)-butanoate 1a (2.2 g, 7.8 mmol) and diisopropylethylamine (1.6 mL, 9.4 mmol) in $CH_3CN$ (80 mL) was stirred at 70° C. for 4 h. The mixture was concentrated under reduced pressure, diluted with EtOAc and washed with 1N HCl and water. The organic phase was separated, dried over $MgSO_4$, filtered and the solvent was evaporated under reduced pressure. The residue was purified by flash chromatography on silica gel (15-40 μm, 80 g, heptane/EtOAc 80/20). The pure fractions were combined and evaporated to dryness to give, after crystallization from diisopropyl ether, tert-butyl 4-(3-((1-(4-chlorophenyl)-2-(5-methoxy-6-(trifluoromethyl)indolin-1-yl)-2-oxoethyl)amino)-5-methoxyphenoxy)butanoate 5f (2.1 g).

Synthesis of Compound 5 and Chiral Separation into Enantiomers 5A and 5B:

A solution of tert-butyl 4-(3-((1-(4-chlorophenyl)-2-(5-methoxy-6-(trifluoromethyl)-indolin-1-yl)-2-oxoethyl) amino)-5-methoxyphenoxy)butanoate 5f (3.1 g, 4.77 mmol) in 4M HCl in dioxane (42.2 mL) was stirred at 5° C. for 3 h and at room temperature for 8 h. The precipitate was filtered off and dried to afford 4-(3-((1-(4-chloro-phenyl)-2-(5-methoxy-6-(trifluoromethyl)indolin-1-yl)-2-oxoethyl) amino)-5-methoxy-phenoxy)butanoic acid as an HCl salt (Compound 5, 2 g). The Enantiomers were separated via Preparative Chiral SFC (Stationary phase: Chiralpak® IA 5 μm 250×20 mm, Mobile phase: 50% $CO_2$, 50% iPrOH (+0.3% $iPrNH_2$+10% $CH_2Ol_2$)). The product fractions were combined and evaporated under reduced pressure. The two enantiomers were taken up with EtOAc and washed with 1N HCl. The organic layers were separated, dried over $MgSO_4$, filtered and the solvent was evaporated under reduced pressure. The first eluted enantiomer (847 mg) was solidified from petroleum ether/diisopropyl ether to give Enantiomer 5A (772 mg). The second eluted enantiomer (840 mg) was solidified from ether/diisopropyl ether to give Enantiomer 5B (724 mg).

Compound 5:
$^1$H NMR (500 MHz, DMSO-d6) δ ppm 1.87 (quin, J=6.9 Hz, 2H) 2.34 (t, J=7.3 Hz, 2H) 3.14-3.35 (m, 2H) 3.61 (s, 3H) 3.80-3.89 (m, 5H) 3.94-4.04 (m, 1H) 4.51 (td, J=10.2, 6.3 Hz, 1H) 5.55 (s, 1H) 5.76 (s, 1H) 5.95 (br d, J=11.7 Hz, 2H) 7.23 (s, 1H) 7.43 (d, J=8.2 Hz, 2H) 7.55 (d, J=8.2 Hz, 2H) 8.34 (s, 1H)

LC/MS (method LC-A): Rt 2.86 min, MH$^+$ 593
Melting point: 130° C.

Enantiomer 5A:
$^1$H NMR (500 MHz, DMSO-d6) δ ppm 1.87 (quin, J=6.9 Hz, 2H) 2.34 (t, J=7.3 Hz, 2H) 3.12-3.31 (m, 2H) 3.62 (s, 3H) 3.81-3.89 (m, 5H) 3.94-4.05 (m, 1H) 4.45-4.56 (m, 1H) 5.55 (br s, 1H) 5.76 (s, 1H) 5.95 (br d, J=11.0 Hz, 2H) 6.40 (br s, 1H) 7.23 (s, 1H) 7.44 (d, J=8.2 Hz, 2H) 7.56 (d, J=8.5 Hz, 2H) 8.34 (s, 1H) 12.14 (br s, 1H)

LC/MS (method LC-A): R$_t$ 2.85 min, MH$^+$ 593
$[α]_D^{20}$: −43.2° (c 0.25, DMF)
Chiral SFC (method SFC-D): R$_t$ 2.16 min, MH$^+$ 593, chiral purity 100%.

Enantiomer 5B:
$^1$H NMR (500 MHz, DMSO-d6) δ ppm 1.87 (quin, J=6.8 Hz, 2H) 2.34 (t, J=7.3 Hz, 2H) 3.13-3.33 (m, 2H) 3.62 (s, 3H) 3.79-3.88 (m, 5H) 3.94-4.03 (m, 1H) 4.51 (td, J=10.3, 6.1 Hz, 1H) 5.54 (br s, 1H) 5.75 (s, 1H) 5.95 (br d, J=11.3 Hz, 2H) 6.40 (br s, 1H) 7.23 (s, 1H) 7.43 (d, J=8.2 Hz, 2H) 7.55 (d, J=8.5 Hz, 2H) 8.34 (s, 1H) 12.14 (br s, 1H)

LC/MS (method LC-A): R$_t$ 2.85 min, MH$^+$ 593
$[α]_D^{20}$: +41.4° (c 0.28, DMF)
Chiral SFC (method SFC-D): R$_t$ 3.75 min, MH$^+$ 593, chiral purity 99.37%.

Example 6: Synthesis of 4-(3-((1-(4-chloro-2-methoxyphenyl)-2-oxo-2-(6-(trifluoro-methyl)indolin-1-yl)ethyl)amino)-5-methoxyphenoxy)butanoic Acid (Compound 6) and Chiral Separation into Enantiomers 6A and 6B

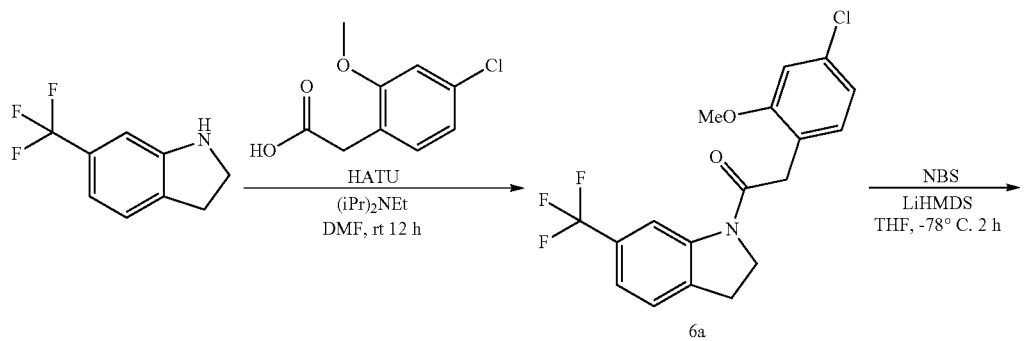

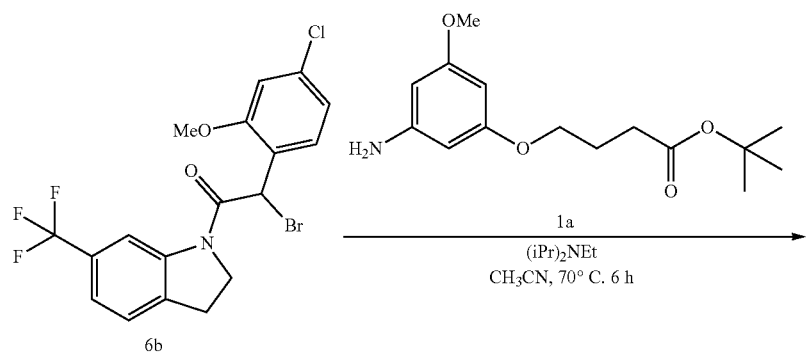

-continued

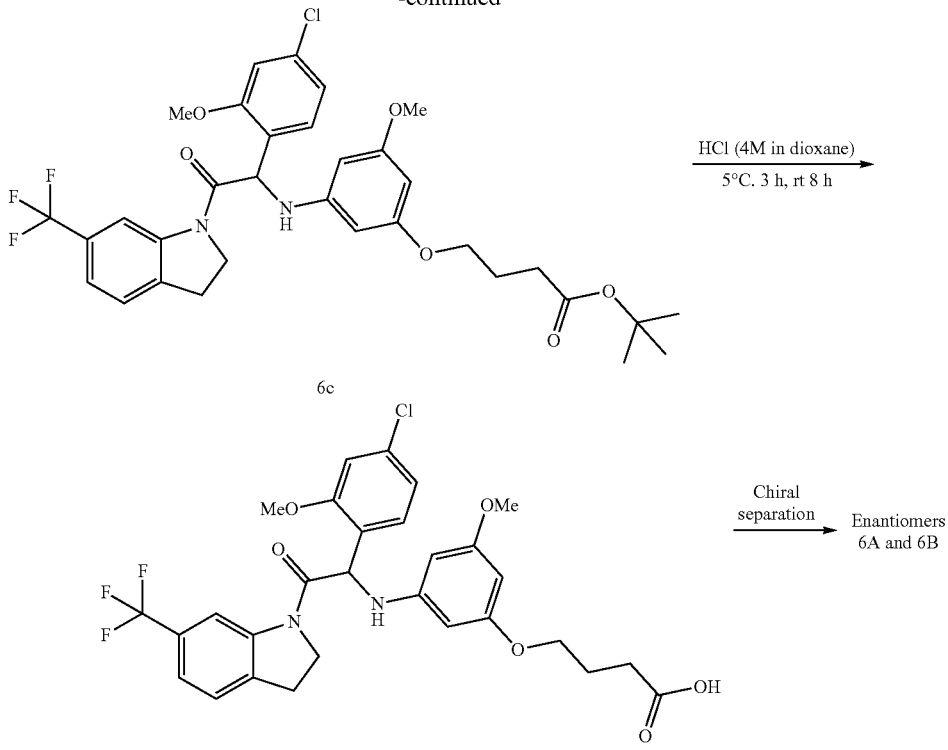

Synthesis of Intermediate 6a:

A mixture of 6-(trifluoromethyl)indoline [CAS 181513-29-1] (2 g, 10.7 mmol), 2-(4-chloro-2-methoxyphenyl)acetic acid [CAS 170737-95-8] (2.36 g, 11.8 mmol), HATU (6.1 g, 16 mmol) and diisopropylethylamine (5.3 mL, 32 mmol) in DMF (50 mL) was stirred at room temperature for 12 h. Water was added and the precipitate was filtered off. The residue was taken up with EtOAc. The organic solution was washed with a 10% aqueous solution of $K_2CO_3$, brine, dried over $MgSO_4$, filtered and the solvent was evaporated under reduced pressure. The residue was purified by chromatography on silica gel (15-40 μm, 80 g, heptane/EtOAc gradient 90/10 to 60/40). The pure fractions were combined and the solvent was concentrated under reduced pressure to give 2-(4-chloro-2-methoxyphenyl)-1-(6-(trifluoromethyl)indolin-1-yl)ethanone 6a (3.9 g).

Synthesis of Intermediate 6b:

At −78° C., under a $N_2$ flow, LiHMDS 1M in THF (13.5 mL, 13.5 mmol) was added dropwise to a mixture of 2-(4-chloro-2-methoxyphenyl)-1-(6-(trifluoromethyl)-indolin-1-yl)ethanone 6a (2.5 g, 6.76 mmol) in THF (40 mL). The mixture was stirred for 15 min at −78° C. and a solution of N-bromosuccinimide (1.32 g, 7.44 mmol) in THF (20 mL) was added dropwise. After stirring for 2 h at −78° C., the reaction was quenched with a saturated solution of $NH_4Cl$. The mixture was extracted with EtOAc. The organic layer was separated, dried over $MgSO_4$, filtered and the solvent was evaporated under reduced pressure to give 2-bromo-2-(4-chloro-2-methoxyphenyl)-1-(6-(trifluoromethyl)indolin-1-yl)ethanone 6b (3 g). The compound was used as such in the next step.

Synthesis of Intermediate 6c:

A mixture of 2-bromo-2-(4-chloro-2-methoxyphenyl)-1-(6-(trifluoromethyl)indolin-1-yl)ethanone 6b (3 g, 6.69 mmol), tert-butyl 4-(3-amino-5-methoxyphenoxy)-butanoate 1a (1.88 g, 6.69 mmol) and diisopropylethylamine (1.4 mL, 8 mmol) in $CH_3CN$ (100 mL) was stirred at 70° C. for 6 h. The mixture was concentrated under reduced pressure, diluted with EtOAc and washed with 1N HCl, and water. The organic phase was separated, dried over $MgSO_4$, filtered and the solvent was evaporated under reduced pressure. The compound was purified by flash chromatography on silica gel (15-40 μm, 80 g, heptane/EtOAc 80/20). The pure fractions were combined and evaporated to dryness to give tert-butyl 4-(3-((1-(4-chloro-2-methoxyphenyl)-2-oxo-2-(6-(trifluoromethyl)indolin-1-yl)ethyl)amino)-5-methoxyphenoxy)butanoate 6c (1.6 g).

Synthesis of Compound 6 and Chiral Separation into Enantiomers 6A and 6B:

A solution of tert-butyl 4-(3-((1-(4-chloro-2-methoxyphenyl)-2-oxo-2-(6-(trifluoro-methyl)indolin-1-yl)ethyl) amino)-5-methoxyphenoxy)butanoate 6c (1.53 g, 2.36 mmol) in 4M HCl in dioxane (20 mL) was stirred at 5° C. for 3 h and at room temperature for 8 h. The solution was concentrated under reduced pressure. The residue was taken up in $CH_3CN$/diisopropyl ether. The precipitate was filtered off and dried to afford 4-(3-((1-(4-chloro-2-methoxyphenyl)-2-oxo-2-(6-(trifluoro-methyl)indolin-1-yl)ethyl) amino)-5-methoxyphenoxy)butanoic acid (Compound 6) as an HCl salt (1.35 g, 0.67 equiv. HCl, 0.28 equiv. $H_2O$). The enantiomers were separated via Preparative Chiral SFC (Stationary phase: Chiralcel® OD-H 5 μm 250×3 0 mm, Mobile phase: 65% $CO_2$, 35% EtOH). The product fractions were combined and evaporated under reduced pressure. The first eluted enantiomer was further purified via reverse phase chromatography (Stationary phase: YMC-actus Triart-C18 10 μm 150×30 mm, Mobile phase: gradient from 55% formic acid 0.1%, 45% $CH_3CN$ to 0% formic acid 0.1%, 100% CH$_3$CN. The pure fractions were combined and evaporated under reduced pressure. The residue (417 mg) was solidified from petroleum ether/diisopropyl ether to give Enantiomer 6A (370 mg). The second eluted enantiomer was further purified via reverse phase chromatography (Stationary phase: YMC-actus Triart-C18 10 µm 150×30 mm, Mobile phase: gradient from 55% formic acid 0.1%, 45% CH$_3$CN to 0% formic acid 0.1%, 100% CH$_3$CN. The pure fractions were combined and evaporated under reduced pressure. The residue (400 mg) then solidified from petroleum ether/diisopropyl ether to give Enantiomer 6B (363 mg).

Compound 6:
$^1$H NMR (400 MHz, DMSO-d6) δ ppm 1.87 (br t, J=6.6 Hz, 2H) 2.33 (br t, J=7.3 Hz, 2H) 3.18-3.32 (m, 2H) 3.61 (s, 3H) 3.80-3.87 (m, 2H) 3.90 (s, 3H) 3.96-4.07 (m, 1H) 4.31-4.45 (m, 1H) 5.61 (s, 1H) 5.76 (s, 1H) 5.87 (br d, J=7.6 Hz, 2H) 7.02 (br d, J=8.1 Hz, 1H) 7.14 (s, 1H) 7.32 (d, J=8.1 Hz, 1H) 7.35-7.41 (m, 1H) 7.43-7.50 (m, 1H) 8.37 (s, 1H)

LC/MS (method LC-A): Rt 2.90 min, MH$^+$ 593
Melting point: 130° C.

Enantiomer 6A:
$^1$H NMR (500 MHz, DMSO-d6) δ ppm 1.87 (quin, J=6.9 Hz, 2H) 2.33 (t, J=7.3 Hz, 2H) 3.24 (br dd, J=18.6, 11.7 Hz, 2H) 3.61 (s, 3H) 3.80-3.87 (m, 2H) 3.90 (s, 3H) 3.97-4.06 (m, 1H) 4.33-4.43 (m, 1H) 5.61 (d, J=8.8 Hz, 1H) 5.76 (s, 1H) 5.87 (br d, J=10.4 Hz, 2H) 6.43 (d, J=8.5 Hz, 1H) 7.03 (dd, J=8.2, 1.9 Hz, 1H) 7.15 (d, J=1.6 Hz, 1H) 7.32 (d, J=8.2 Hz, 1H) 7.39 (d, J=7.9 Hz, 1H) 7.46 (d, J=7.9 Hz, 1H) 8.37 (s, 1H) 12.16 (br s, 1H)

LC/MS (method LC-A): R$_t$ 2.99 min, MH$^+$ 593
[α]$_D^{20}$: −28.6° (c 0.29, DMF)
Chiral SFC (method SFC-E): R$_t$ 2.17 min, MH$^+$ 593, chiral purity 100%.
Melting point: 178° C.

Enantiomer 6B:
$^1$H NMR (500 MHz, DMSO-d6) δ ppm 1.87 (quin, J=6.9 Hz, 2H) 2.33 (t, J=7.3 Hz, 2H) 3.24 (br dd, J=18.8, 11.5 Hz, 2H) 3.61 (s, 3H) 3.83 (q, J=6.2 Hz, 2H) 3.90 (s, 3H) 3.96-4.08 (m, 1H) 4.32-4.43 (m, 1H) 5.61 (d, J=8.5 Hz, 1H) 5.76 (s, 1H) 5.87 (br d, J=10.1 Hz, 2H) 6.43 (br d, J=8.5 Hz, 1H) 7.03 (dd, J=8.2, 1.6 Hz, 1H) 7.15 (d, J=1.6 Hz, 1H) 7.32 (d, J=8.2 Hz, 1H) 7.39 (d, J=7.6 Hz, 1H) 7.46 (d, J=7.9 Hz, 1H) 8.37 (s, 1H) 12.16 (br s, 1H)

LC/MS (method LC-A): R$_t$ 3.00 min, MH$^+$ 593
[α]$_D^{20}$: +32.1° (c 0.28, DMF)
Chiral SFC (method SFC-E): R$_t$ 4.04 min, MH$^+$ 593, chiral purity 100%.

Example 7: Synthesis of 4-(3-((1-(4-chloro-2-methoxyphenyl)-2-(5-methoxy-6-(trifluoromethyl)indolin-1-yl)-2-oxoethyl)amino)-5-methoxyphenoxy)butanoic Acid (Compound 7) and Chiral Separation into Enantiomers 7A and 7B

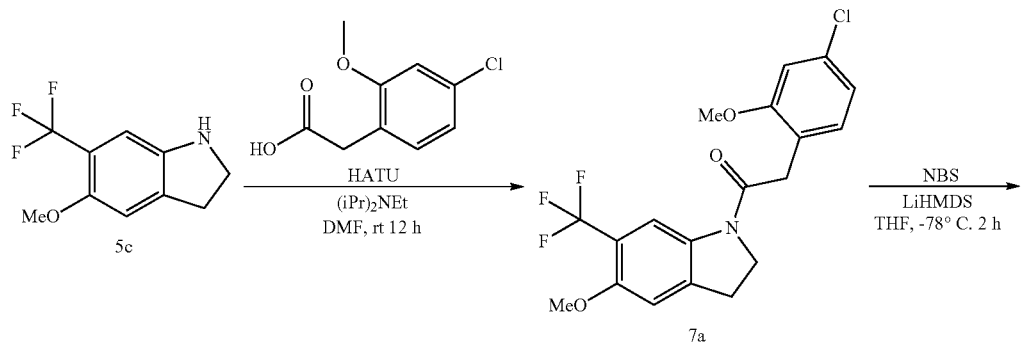

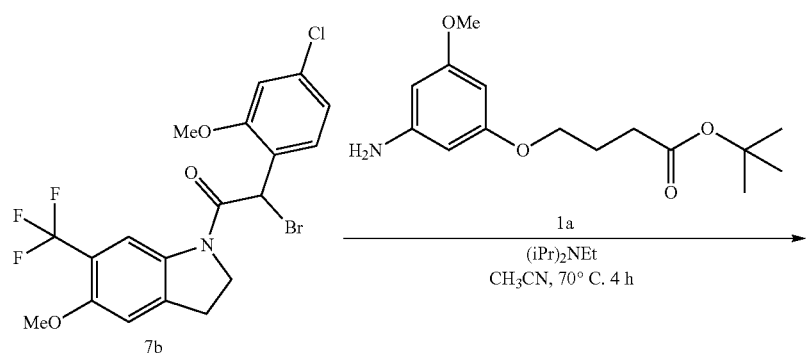

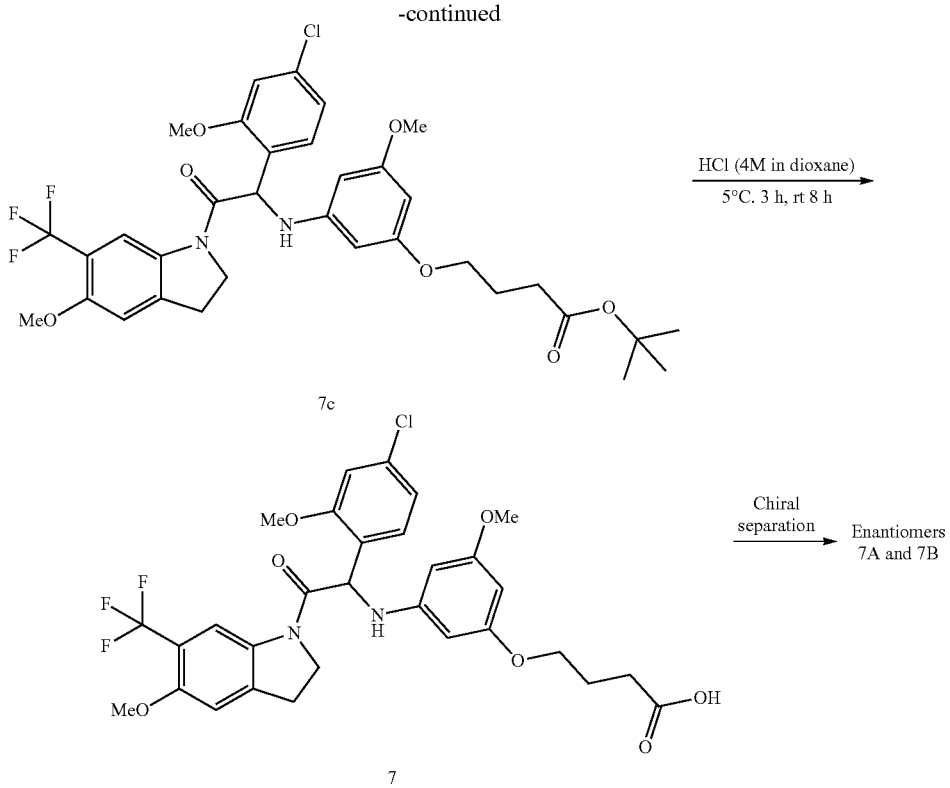

Synthesis of Intermediate 7a:

A mixture of 5-methoxy-6-(trifluoromethyl)indoline 5c (1.5 g, 6.9 mmol), 2-(4-chloro-2-methoxyphenyl)acetic acid [CAS 170737-95-8] (1.4 g, 6.9 mmol), HATU (3.94 g, 10.4 mmol) and diisopropylethylamine (3.4 mL, 20.7 mmol) in DMF (40 mL) was stirred at room temperature for 12 h. Ice/water was added and the precipitate was filtered off. The residue was taken up with $CH_2Cl_2$. The organic solution was washed with a 10% aqueous solution of $K_2CO_3$, brine, dried over $MgSO_4$, filtered and the solvent was evaporated under reduced pressure. The residue was crystallized from diisopropyl ether to give 2-(4-chloro-2-methoxyphenyl)-1-(5-methoxy-6-(trifluoromethyl)indolin-1-yl)ethanone 7a (2.48 g).

Synthesis of Intermediate 7b:

At −78° C., under a $N_2$ flow, LiHMDS 1M in THF (16.5 mL, 16.5 mmol) was added dropwise to a mixture of 2-(4-chloro-2-methoxyphenyl)-1-(5-methoxy-6-(trifluoromethyl)indolin-1-yl)ethanone 7a (3.3 g, 8.25 mmol) in THF (45 mL). TMSCl (1.26 mL, 9.91 mmol) was added dropwise. The mixture was stirred for 15 min at −78° C. and a solution of N-bromosuccinimide (1.76 g, 9.91 mmol) in THF (30 mL) was added dropwise. After stirring for 2 h at −78° C., the reaction was quenched with a saturated solution of $NH_4Cl$. The mixture was extracted with EtOAc. The organic layer was separated, dried over $MgSO_4$, filtered and the solvent was evaporated under reduced pressure to give 2-bromo-2-(4-chloro-2-methoxy-phenyl)-1-(5-methoxy-6-(trifluoromethyl)indolin-1-yl)ethanone 7b (3.5 g). The compound was used as such in the next step.

Synthesis of Intermediate 7c:

A mixture of 2-bromo-2-(4-chloro-2-methoxyphenyl)-1-(5-methoxy-6-(trifluoro-methyl)indolin-1-yl)ethanone 7b (3.5 g, 7.31 mmol), tert-butyl 4-(3-amino-5-methoxyphenoxy)butanoate 1a (2 g, 7.31 mmol) and diisopropylethylamine (1.5 mL, 8.8 mmol) in $CH_3CN$ (80 mL) was stirred at 70° C. for 4 h. The mixture was concentrated under reduced pressure, diluted with EtOAc and washed with 1N HCl, and water. The organic phase was separated, dried over $MgSO_4$, filtered and the solvent was evaporated under reduced pressure. The compound was purified by flash chromatography on silica gel (15-40 μm, 80 g, heptane/EtOAc 80/20). The pure fractions were combined and evaporated to dryness to give tert-butyl 4-(3-((1-(4-chloro-2-methoxyphenyl)-2-(5-methoxy-6-(trifluoromethyl)indolin-1-yl)-2-oxoethyl)amino)-5-methoxyphenoxy)butanoate 7c (2.2 g).

Synthesis of Compound 7 and Chiral Separation into Enantiomers 7A and 7B:

A solution of tert-butyl 4-(3-((1-(4-chloro-2-methoxyphenyl)-2-(5-methoxy-6-(trifluoromethyl)indolin-1-yl)-2-oxoethyl)amino)-5-methoxyphenoxy)butanoate 7c (2.1 g, 3.1 mmol) in 4M HCl in dioxane (27.4 mL) was stirred at 5° C. for 3 h and at room temperature for 8 h. The solution was concentrated under reduced pressure. The residue was taken up in $CH_3CN$/diisopropyl ether. The precipitate was filtered off and dried to afford 4-(3-((1-(4-chloro-2-methoxyphenyl)-2-(5-methoxy-6-(trifluoromethyl)indolin-1-yl)-2-oxoethyl)amino)-5-methoxyphenoxy)butanoic acid (Compound 7) as an HCl salt (1.5 g, 0.74 equiv. HCl, 0.29 equiv. $H_2O$). The enantiomers were separated via Preparative Chiral SFC (Stationary phase: Chiralcel® OD-H 5 μm 250×30 mm, Mobile phase: 55% $CO_2$, 45% iPrOH). The product fractions were combined and evaporated under reduced pressure. The first eluted enantiomer (671 mg) was solidified from petroleum ether/diisopropyl ether to give Enantiomer 7A (606 mg). The second eluted enantiomer (647 mg) was solidified from petroleum ether/diisopropyl ether to give Enantiomer 6B (580 mg).

Compound 7:

¹H NMR (500 MHz, DMSO-d6) δ ppm 1.87 (quin, J=6.7 Hz, 2H) 2.34 (t, J=7.3 Hz, 2H) 3.17-3.30 (m, 2H) 3.61 (s, 3H) 3.79-3.87 (m, 5H) 3.90 (s, 3H) 3.93-4.02 (m, 1H) 4.29-4.40 (m, 1H) 5.59 (s, 1H) 5.75 (s, 1H) 5.87 (br d, J=10.7 Hz, 2H) 7.02 (dd, J=8.2, 1.6 Hz, 1H) 7.14 (d, J=1.3 Hz, 1H) 7.24 (s, 1H) 7.32 (d, J=8.5 Hz, 1H) 8.32 (s, 1H)

LC/MS (method LC-A): Rt 2.89 min, MH⁺ 623

Melting point: 160° C.

Enantiomer 7A:

¹H NMR (500 MHz, DMSO-d6) δ ppm 1.87 (br t, J=6.8 Hz, 2H) 2.34 (br t, J=7.1 Hz, 2H) 3.18-3.28 (m, 2H) 3.61 (s, 3H) 3.79-3.87 (m, 5H) 3.91 (s, 3H) 3.94-4.05 (m, 1H) 4.31-4.42 (m, 1H) 5.59 (br d, J=8.2 Hz, 1H) 5.76 (br s, 1H) 5.87 (br d, J=10.4 Hz, 2H) 6.40 (br d, J=8.5 Hz, 1H) 7.02 (br d, J=7.9 Hz, 1H) 7.14 (s, 1H) 7.24 (s, 1H) 7.33 (br d, J=8.2 Hz, 1H) 8.33 (s, 1H) 12.18 (br s, 1H)

LC/MS (method LC-A): $R_t$ 2.87 min, MH⁺ 623

$[\alpha]_D^{20}$: (c 0.28, DMF)

Chiral SFC (method SFC-C): $R_t$ 1.76 min, MH⁺ 623, chiral purity 100%.

Enantiomer 7B:

¹H NMR (500 MHz, DMSO-d6) δ ppm 1.87 (quin, J=6.5 Hz, 2H) 2.34 (br t, J=7.1 Hz, 2H) 3.18-3.28 (m, 2H) 3.61 (s, 3H) 3.80-3.87 (m, 5H) 3.91 (s, 3H) 3.94-4.02 (m, 1H) 4.28-4.41 (m, 1H) 5.59 (br d, J=8.2 Hz, 1H) 5.75 (br s, 1H) 5.87 (br d, J=10.4 Hz, 2H) 6.40 (br d, J=8.5 Hz, 1H) 7.02 (br d, J=7.9 Hz, 1H) 7.14 (s, 1H) 7.24 (s, 1H) 7.33 (br d, J=8.2 Hz, 1H) 8.33 (s, 1H) 12.17 (br s, 1H)

LC/MS (method LC-A): $R_t$ 2.87 min, MH⁺ 623

$[\alpha]_D^{20}$: +28.5° (c 0.26, DMF)

Chiral SFC (method SFC-C): $R_t$ 3.52 min, MH⁺ 623, chiral purity 100%.

Example 8: Synthesis of 4-(3-((1-(4-chloro-2-methoxyphenyl)-2-oxo-2-(6-(trifluoro-methoxy)indolin-1-yl)ethyl)amino)-5-methoxyphenoxy)butanoic Acid (Compound 8) and Chiral Separation into Enantiomers 8A and 8B

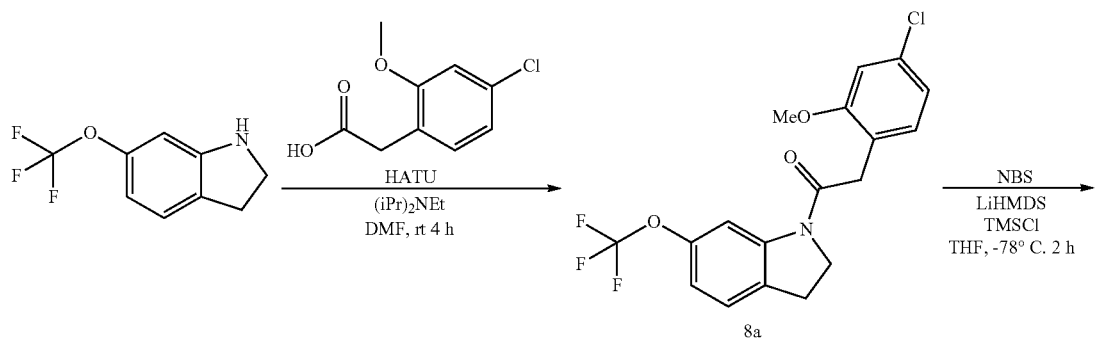

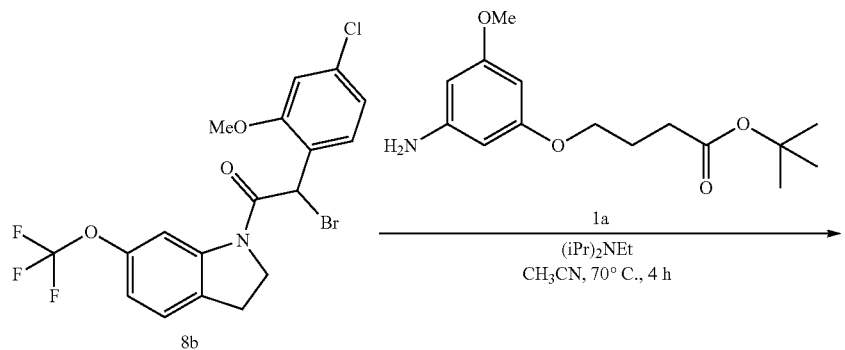

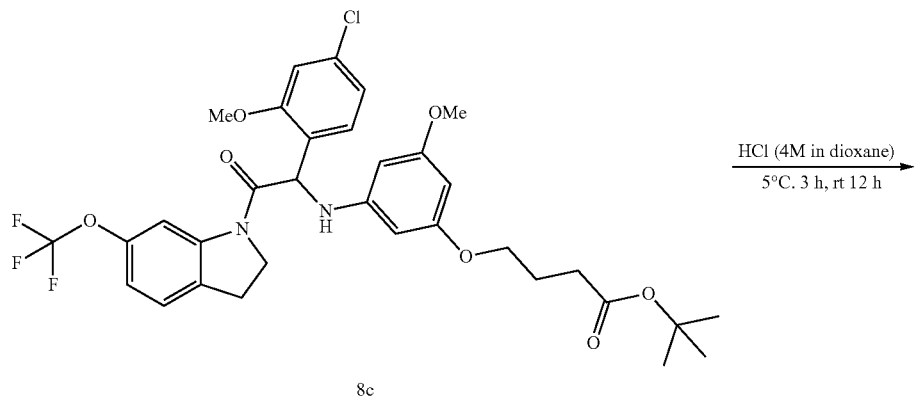

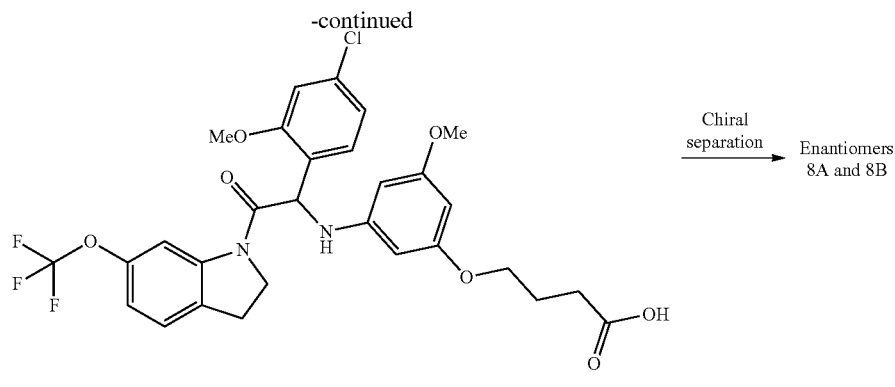

8

Synthesis of Intermediate 8a:

A mixture of 6-(trifluoromethoxy)indoline [CAS 959235-95-1] (2.5 g, 12.3 mmol), 2-(4-chloro-2-methoxyphenyl)acetic acid [CAS 170737-95-8] (2.47 g, 12.3 mmol), HATU (7 g, 18.5 mmol) and diisopropylethylamine (6.1 mL, 36.9 mmol) in DMF (40-mL) was stirred at room temperature for 4 h. Water and EtOAc were added. The organic layer was separated, washed with water, dried over $MgSO_4$, filtered and the solvent was evaporated under reduced pressure. The residue was purified by chromatography on silica gel (15-40 µm, 80 g, heptane/EtOAc 85/15). The pure fractions were combined and the solvent was concentrated under reduced pressure to give, after crystallization from $CH_3CN$/heptane, 2-(4-chloro-2-methoxyphenyl)-1-(6-(trifluoromethoxy)indolin-1-yl)ethanone 8a (4.3 g).

Synthesis of intermediate 8b:

At −78° C., under a $N_2$ flow, LiHMDS 1M in THF (19.7 mL, 19.7 mmol) was added dropwise to a mixture of 2-(4-chloro-2-methoxyphenyl)-1-(6-(trifluoromethoxy)-indolin-1-yl)ethanone 8a (3.8 g, 9.8 mmol) in THF (50 mL). TMSCI (1.5 mL, 11.8 mmol) was added dropwise. The mixture was stirred for 15 min at −78° C. and a solution of N-bromosuccinimide (1.9 g, 10.8 mmol) in THF (35 mL) was added dropwise. After stirring for 2 h at −78° C., the reaction was quenched with a saturated solution of $NH_4Cl$. The mixture was extracted with EtOAc. The organic layer was separated, dried over $MgSO_4$, filtered and the solvent was evaporated under reduced pressure to give 2-bromo-2-(4-chloro-2-methoxyphenyl)-1-(6-(trifluoromethoxy)indolin-1-yl)ethanone 8b (4.5 g). The compound was used as such in the next step.

Synthesis of Intermediate 8c:

A mixture of 2-bromo-2-(4-chloro-2-methoxyphenyl)-1-(6-(trifluoromethoxy)indolin-1-yl)ethanone 8b (4.5 g, 9.68 mmol), tert-butyl 4-(3-amino-5-methoxyphenoxy)-butanoate 1a (2.7 g, 9.68 mmol) and diisopropylethylamine (2 mL, 11.6 mmol) in $CH_3CN$ (100 mL) was stirred at 70° C. for 4 h. The mixture was concentrated under reduced pressure, diluted with EtOAc and washed with 1N HCl and water. The organic phase was separated, dried over $MgSO_4$, filtered and the solvent was evaporated under reduced pressure. The residue was purified by flash chromatography on silica gel (15-40 µm, 120 g, heptane/EtOAc 80/20). The pure fractions were combined and evaporated to dryness to give, after crystallization from $CH_3CN$, tert-butyl 4-(3-((1-(4-chloro-2-methoxyphenyl)-2-oxo-2-(6-(trifluoro-methoxy)indolin-1-yl)ethyl)amino)-5-methoxyphenoxy)butanoate 8c (2.3 g).

Synthesis of Compound 8 and Chiral Separation into Enantiomers 8A and 8B:

A solution of tert-butyl 4-(3-((1-(4-chloro-2-methoxyphenyl)-2-oxo-2-(6-(trifluoro-methoxy)indolin-1-yl)ethyl)amino)-5-methoxyphenoxy)butanoate 8c (2.3 g, 3.46 mmol) in 4M HCl in dioxane (30 mL) was stirred at 5° C. for 3 h and at room temperature for 12 h. The precipitate was filtered off, washed with diisopropyl ether and dried to afford 4-(3-((1-(4-chloro-2-methoxyphenyl)-2-oxo-2-(6-(trifluoromethoxy)indolin-1-yl)ethyl)amino)-5-methoxyphenoxy)butanoic acid (Compound 8) as an HCl salt (1.79 g, 0.86 equiv. HCl, 0.22 equiv. $H_2O$). The enantiomers were separated via Preparative Chiral SFC (Stationary phase: Chiralcel® OD-H 5 µm 250×30 mm, Mobile phase: 65% $CO_2$, 35% iPrOH). The product fractions were combined and evaporated under reduced pressure. The first eluted enantiomer (726 mg) was solidified from petroleum ether/diisopropyl ether to give Enantiomer 8A (612 mg). The second eluted enantiomer (712 mg) was solidified from petroleum ether/diisopropyl ether to give Enantiomer 8B (643 mg).

Compound 8:

$^1$H NMR (500 MHz, DMSO-d6) δ ppm 1.87 (quin, J=6.9 Hz, 2H) 2.34 (br t, J=7.3 Hz, 2H) 3.08-3.26 (m, 2H) 3.61 (s, 3H) 3.83 (q, J=6.5 Hz, 2H) 3.90 (s, 3H) 3.98-4.09 (m, 1H) 4.31-4.42 (m, 1H) 5.60 (s, 1H) 5.76 (s, 1H) 5.87 (br d, J=9.5 Hz, 2H) 6.98-7.05 (m, 2H) 7.14 (d, J=1.9 Hz, 1H) 7.31 (d, J=8.2 Hz, 1H) 7.34 (d, J=8.2 Hz, 1H) 8.02 (s, 1H)

LC/MS (method LC-A): Rt 3.04 min, MH$^+$ 609

Melting point: 139° C.

Enantiomer 8A:

$^1$H NMR (500 MHz, DMSO-d6) δ ppm 1.87 (quin, J=6.9 Hz, 2H) 2.33 (t, J=7.4 Hz, 2H) 3.09-3.25 (m, 2H) 3.61 (s, 3H) 3.78-3.87 (m, 2H) 3.90 (s, 3H) 3.98-4.07 (m, 1H) 4.32-4.42 (m, 1H) 5.59 (d, J=8.5 Hz, 1H) 5.76 (s, 1H) 5.86 (s, 1H) 5.88 (s, 1H) 6.45 (d, J=8.8 Hz, 1H) 6.97-7.06 (m, 2H) 7.14 (d, J=1.3 Hz, 1H) 7.31 (d, J=8.5 Hz, 1H) 7.34 (d, J=8.2 Hz, 1H) 8.02 (s, 1H) 12.14 (br s, 1H)

LC/MS (method LC-A): $R_t$ 3.03 min, MH$^+$ 609

$[α]_D^{20}$: (c 0.28, DMF)

Chiral SFC (method SFC-F): $R_t$ 2.32 min, MH$^+$ 609, chiral purity 100%.

Enantiomer 8B:

$^1$H NMR (500 MHz, DMSO-d6) δ ppm 1.87 (quin, J=6.8 Hz, 2H) 2.34 (t, J=7.3 Hz, 2H) 3.09-3.25 (m, 2H) 3.61 (s, 3H) 3.79-3.88 (m, 2H) 3.90 (s, 3H) 4.02 (td, J=10.2, 6.9 Hz, 1H) 4.33-4.41 (m, 1H) 5.60 (s, 1H) 5.76 (s, 1H) 5.86 (s, 1H) 5.88 (s, 1H) 6.45 (br s, 1H) 6.99-7.05 (m, 2H) 7.14 (d, J=1.6 Hz, 1H) 7.31 (d, J=8.5 Hz, 1H) 7.34 (d, J=8.2 Hz, 1H) 8.02 (s, 1H) 12.12 (br s, 1H)

LC/MS (method LC-A): $R_t$ 3.03 min, MH$^+$ 609

$[α]_D^{20}$: +34.5° (c 0.29, DMF)

Chiral SFC (method SFC-F): $R_t$ 3.51 min, MH$^+$ 609, chiral purity 100%.

Example 9: Synthesis of 4-(3-((1-(4-chloro-2-fluorophenyl)-2-oxo-2-(6-(trifluoro-methyl)indolin-1-yl)ethyl)amino)-5-methoxyphenoxy)butanoic Acid (Compound 9) and Chiral Separation into Enantiomers 9A and 9B
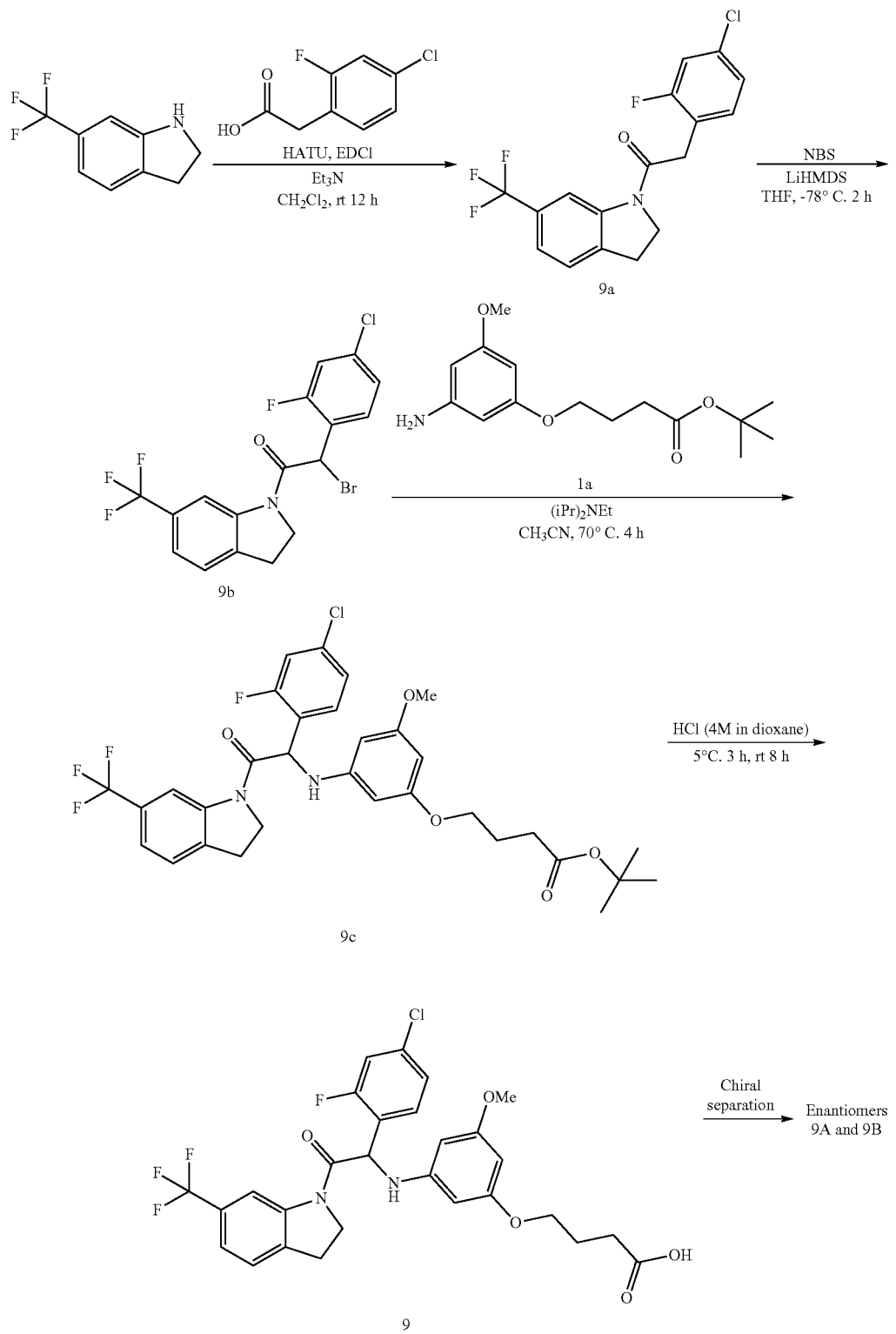

Synthesis of Intermediate 9a:

A mixture of 2-(4-chloro-2-fluorophenyl)acetic acid [CAS 194240-75-0] (2.52 g, 13.4 mmol), 6-(trifluoromethyl)indoline [CAS 181513-29-1] (2.5 g, 13.4 mmol), hydroxybenzotriazole (2.7 g, 20.04 mmol), 1-ethyl-3-(3-dimethylaminopropyl)-carbodiimide (3.84 g, 20.04 mmol) and trimethylamine (3.71 mL, 26.7 mmol) in $CH_2Cl_2$ (30 mL) was stirred at room temperature for 12 h. Water was added and the layers were separated. The organic layer was washed with water, dried over $MgSO_4$, filtered and the solvent was evaporated under reduced pressure to give, after crystallization from $CH_3CN$/diisopropyl ether, 2-(4-chloro-2-fluorophenyl)-1-(6-(trifluoromethyl)indolin-1-yl)ethanone 9a (3.9 g). The compound was used as such in the next step.

Synthesis of Intermediate 9b:

At −78° C., under a $N_2$ flow, LiHMDS 1M in THF (13.98 mL, 13.98 mmol) was added dropwise to a mixture of 2-(4-chloro-2-fluorophenyl)-1-(6-(trifluoromethyl)indolin-1-yl)ethanone 9a (2.5 g, 6.99 mmol) in THF (20 mL). The mixture was stirred for 15 min at −78° C. and a solution of N-bromosuccinimide (1.37 g, 7.69 mmol) in THF (15 mL) was added dropwise. After stirring for 2 h at −78° C., the reaction was quenched with a saturated solution of $NH_4Cl$. The mixture was extracted with EtOAc. The organic layer was separated, dried over $MgSO_4$, filtered and the solvent was evaporated under reduced pressure to give 2-bromo-2-(4-chloro-2-fluorophenyl)-1-(6-(trifluoromethyl)indolin-1-yl)ethanone 9b (2.8 g). The compound was used as such in the next step.

Synthesis of Intermediate 9c:

A mixture of 2-bromo-2-(4-chloro-2-fluorophenyl)-1-(6-(trifluoromethyl)indolin-1-yl)-ethanone 9b (2.8 g, 6.41 mmol), tert-butyl 4-(3-amino-5-methoxyphenoxy)-butanoate 1a (1.8 g, 6.41 mmol) and diisopropylethylamine (1.33 mL, 7.7 mmol) in $CH_3CN$ (90 mL) was stirred at 70° C. for 4 h. The mixture was concentrated under reduced pressure, diluted with EtOAc, and washed with 1N HCl, and water. The organic phase was separated, dried over $MgSO_4$, filtered and the solvent was evaporated under reduced pressure. The residue was purified by flash chromatography on silica gel (15-40 μm, 80 g, heptane/EtOAc 80/20). The pure fractions were combined and evaporated to dryness to give, after crystallization from $CH_3CN$/diisopropyl ether, tert-butyl 4-(3-((1-(4-chloro-2-fluorophenyl)-2-oxo-2-(6-(trifluoromethyl)indolin-1-yl)ethyl)amino)-5-methoxyphenoxy)butanoate 9c (1.75 g).

Synthesis of Compound 9 and Chiral Separation into Enantiomers 9A and 9B:

A solution of tert-butyl 4-(3-((1-(4-chloro-2-fluorophenyl)-2-oxo-2-(6-(trifluoro-methyl)indolin-1-yl)ethyl)amino)-5-methoxyphenoxy)butanoate 9c (1.75 g, 2.75 mmol) in 4M HCl in dioxane (24.3 mL) was stirred at 5° C. for 3 h and at room temperature for 8 h. The mixture was concentrated under reduced pressure. The residue was crystallized from $CH_3CN$/diisopropyl ether to afford 4-(3-((1-(4-chloro-2-fluorophenyl)-2-oxo-2-(6-(trifluoromethyl)indolin-1-yl)ethyl)amino)-5-methoxy-phenoxy)butanoic acid (Compound 9) as an HCl salt (1.4 g, 0.8 equiv. HCl, 0.78 equiv. $H_2O$). The enantiomers were separated via Preparative Chiral SFC (Stationary phase: Chiralpak® AD-H 5 μm 250×30 mm, Mobile phase: 70% $CO_2$, 30% iPrOH). The product fractions were combined and evaporated under reduced pressure. The first eluted enantiomer (618 mg) was solidified from petroleum ether/diisopropyl ether to give Enantiomer 9A (505 mg). The second eluted enantiomer (548 mg) was solidified from petroleum ether/diisopropyl ether to give Enantiomer 9B (495 mg).

Compound 9:

$^1$H NMR (500 MHz, DMSO-d6) δ ppm 1.87 (quin, J=6.9 Hz, 2H) 2.34 (t, J=7.3 Hz, 2H) 3.18-3.34 (m, 2H) 3.63 (s, 3H) 3.80-3.90 (m, 2H) 4.02-4.14 (m, 1H) 4.40-4.49 (m, 1H) 5.72 (s, 1H) 5.80 (s, 1H) 5.94 (br d, J=10.1 Hz, 2H) 7.33 (dd, J=8.5, 1.6 Hz, 1H) 7.39-7.43 (m, 1H) 7.43-7.50 (m, 3H) 8.36 (s, 1H)

LC/MS (method LC-A): Rt 2.99 min, MH+ 581

Melting point: 110° C.

Enantiomer 9A:

$^1$H NMR (500 MHz, DMSO-d6) δ ppm 1.87 (quin, J=6.7 Hz, 2H) 2.33 (br t, J=7.1 Hz, 2H) 3.22-3.28 (m, 2H) 3.62 (s, 3H) 3.80-3.90 (m, 2H) 4.03-4.13 (m, 1H) 4.39-4.48 (m, 1H) 5.72 (br d, J=8.8 Hz, 1H) 5.80 (s, 1H) 5.93 (br d, J=10.7 Hz, 2H) 6.60 (br d, J=8.8 Hz, 1H) 7.33 (br d, J=7.9 Hz, 1H) 7.39-7.43 (m, 1H) 7.43-7.51 (m, 3H) 8.36 (s, 1H) 12.19 (br s, 1H)

LC/MS (method LC-A): $R_t$ 2.98 min, MH+ 581

$[α]_D^{20}$: −30.0° (c 0.29, DMF)

Chiral SFC (method SFC-G): $R_t$ 1.97 min, MH+ 581, chiral purity 100%.

Enantiomer 9B:

$^1$H NMR (500 MHz, DMSO-d6) δ ppm 1.87 (quin, J=6.9 Hz, 2H) 2.33 (t, J=7.3 Hz, 2H) 3.21-3.28 (m, 2H) 3.63 (s, 3H) 3.80-3.91 (m, 2H) 4.02-4.12 (m, 1H) 4.40-4.49 (m, 1H) 5.72 (d, J=9.1 Hz, 1H) 5.80 (s, 1H) 5.94 (br d, J=11.0 Hz, 2H) 6.60 (br d, J=8.8 Hz, 1H) 7.33 (dd, J=8.2, 1.6 Hz, 1H) 7.38-7.43 (m, 1H) 7.43-7.50 (m, 3H) 8.36 (s, 1H) 11.04-12.93 (m, 1H)

LC/MS (method LC-A): $R_t$ 2.98 min, MH+ 581

$[α]_D^{20}$: +27.9° (c 0.28, DMF)

Chiral SFC (method SFC-G): $R_t$ 3.19 min, MH+ 581, chiral purity 99.35%.

Example 10: Synthesis of 4-(3-((1-(4-chloro-2-fluorophenyl)-2-oxo-2-(6-(trifluoro-methoxy)indolin-1-yl)ethyl)amino)-5-methoxyphenoxy)butanoic Acid (Compound 10) and Chiral Separation into Enantiomers 10A and 10B

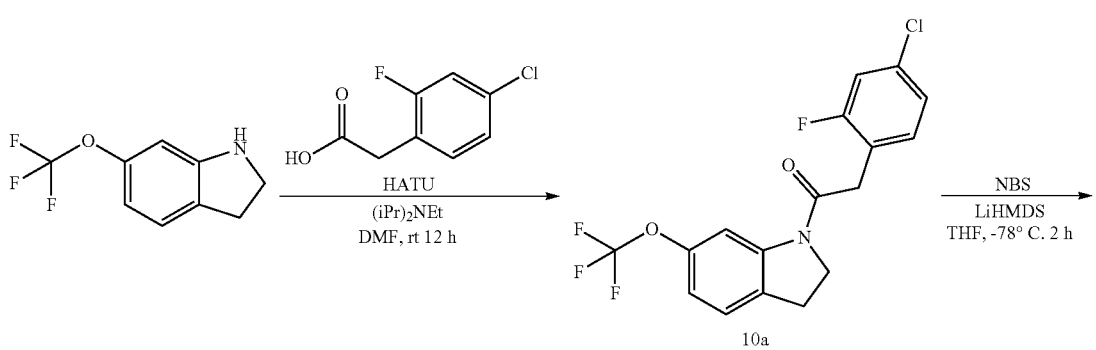

10a

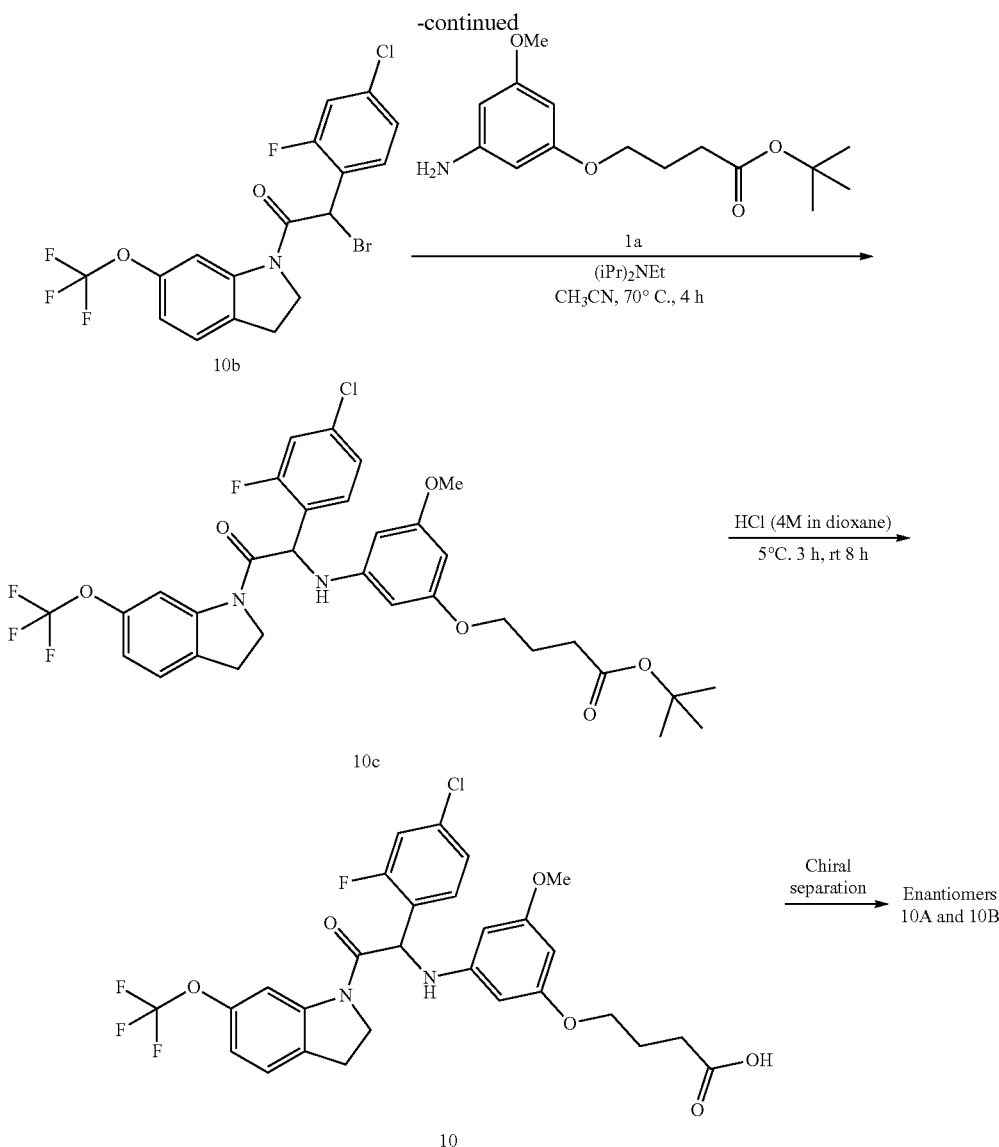

Synthesis of Intermediate 10a:

HATU (7.02 g, 18.46 mmol) was added to a mixture of 6-(trifluoromethoxy)indoline [CAS 959235-95-1] (2.5 g, 12.3 mmol), 2-(4-chloro-2-fluorophenyl)acetic acid [CAS 194240-75-0] (2.32 g, 12.3 mmol) and diisopropylethylamine (6.1 mL, 36.9 mmol) in DMF (100 mL). The resulting mixture was stirred at room temperature for 12 h. The mixture was diluted with water, the precipitate was filtered off, and washed with water. The residue was taken up with EtOAc and the organic solution was washed with a 10% aqueous solution of K$_2$CO$_3$, brine, dried over MgSO$_4$, filtered and the solvent was evaporated under reduced pressure. The residue product was crystallized from diisopropyl ether to give 2-(4-chloro-2-fluorophenyl)-1-(6-(trifluoromethoxy)indolin-1-yl)ethanone 10a (4 g).

Synthesis of Intermediate 10b:

At −78° C., under a N$_2$ flow, LiHMDS 1M in THF (21.4 mL, 21.4 mmol) was added dropwise to a mixture of 2-(4-chloro-2-fluorophenyl)-1-(6-(trifluoromethoxy)indolin-1-yl)ethanone 10a (4 g, 10.7 mmol) in THF (60 mL). The mixture was stirred for 15 min at −78° C. and a solution of N-bromosuccinimide (2.1 g, 11.8 mmol) in THF (40 mL) was added dropwise. After stirring for 2 h at −78° C., the reaction was quenched with a saturated solution of NH$_4$Cl. The mixture was extracted with EtOAc. The organic layer was separated, dried over MgSO$_4$, filtered and the solvent was evaporated under reduced pressure to give 2-bromo-2-(4-chloro-2-fluorophenyl)-1-(6-(trifluoromethoxy)indolin-1-yl)ethanone 10b (4.8 g). The compound was used as such in the next step.

Synthesis of Intermediate 10c:

A mixture of 2-bromo-2-(4-chloro-2-fluorophenyl)-1-(6-(trifluoromethoxy)indolin-1-yl)ethanone 10b (3 g, 6.63 mmol), tert-butyl 4-(3-amino-5-methoxyphenoxy)-butanoate 1a (1.86 g, 6.63 mmol) and diisopropylethylamine (1.37 mL, 7.95 mmol) in CH$_3$CN (60 mL) was stirred at 70° C. for 4 h. The mixture was concentrated under reduced pressure, diluted with EtOAc, and washed with 1N HCl 1N and water. The organic phase was separated, dried over MgSO$_4$, filtered and the solvent was evaporated under reduced pressure. The residue was purified by flash chromatography on silica gel (15-40 µm, 120 g, heptane/EtOAc 80/20). The pure fractions were combined and evaporated to dryness to give tert-butyl 4-(3-((1-(4-chloro-2-fluorophenyl)-2-oxo-2-(6-(trifluoromethoxy)indolin-1-yl)ethyl)amino)-5-methoxyphenoxy)butanoate 10c (835 mg).

Synthesis of Compound 10 and Chiral Separation into Enantiomers 10A and 10B:

A solution of tert-butyl 4-(3-((1-(4-chloro-2-fluorophenyl)-2-oxo-2-(6-(trifluoro-methoxy)indolin-1-yl)ethyl)amino)-5-methoxyphenoxy)butanoate 10c (835 mg, 1.28 mmol) in 4M HCl in dioxane (11.3 mL) was stirred at 5° C. for 3 h and at room temperature for 8 h. The solution was concentrated under reduced pressure. The residue was solidified from diisopropyl ether to afford 4-(3-((1-(4-chloro-2-fluorophenyl)-2-oxo-2-(6-(trifluoromethoxy)indolin-1-yl)ethyl)amino)-5-methoxy-phenoxy)butanoic acid (Compound 10) (620 mg). The enantiomers were separated via Preparative Chiral SFC (Stationary phase: Chiralpak® IC 5 μm 250×30 mm, Mobile phase: 70% $CO_2$, 30% iPrOH (+0.3% iPrNH$_2$). The product fractions were combined and evaporated under reduced pressure. The first eluted enantiomer (249 mg) was taken up with EtOAc and washed with 1N HCl. The organic layer was separated, dried over MgSO$_4$, filtered and concentrated under reduced pressure. The residue was solidified from petroleum ether/diisopropyl ether to give Enantiomer 10A (183 mg). The second eluted enantiomer (274 mg) was taken up with EtOAc and washed with 1N HCl. The organic layer was separated, dried over MgSO$_4$, filtered and concentrated under reduced pressure. The residue was solidified from petroleum ether/diisopropyl ether to give Enantiomer 10B (186 mg).

Compound 10:

$^1$H NMR (500 MHz, DMSO-d6) δ ppm 1.87 (quin, J=6.8 Hz, 2H) 2.33 (br t, J=7.3 Hz, 2H) 3.09-3.24 (m, 2H) 3.62 (s, 3H) 3.81-3.89 (m, 2H) 4.05-4.13 (m, 1H) 4.38-4.47 (m, 1H) 5.70 (br d, J=9.1 Hz, 1H) 5.79 (s, 1H) 5.93 (br d, J=9.8 Hz, 2H) 6.62 (br d, J=8.8 Hz, 1H) 7.03 (br d, J=8.2 Hz, 1H) 7.31-7.37 (m, 2H) 7.41-7.50 (m, 2H) 8.02 (s, 1H) 12.15 (br s, 1H)

LC/MS (method LC-A): Rt 3.07 min, MH$^+$ 597

Enantiomer 10A:

$^1$H NMR (500 MHz, DMSO-d6) δ ppm 1.87 (quin, J=6.9 Hz, 2H) 2.34 (t, J=7.3 Hz, 2H) 3.12-3.22 (m, 2H) 3.62 (s, 3H) 3.79-3.90 (m, 2H) 4.04-4.13 (m, 1H) 4.38-4.48 (m, 1H) 5.70 (d, J=8.8 Hz, 1H) 5.79 (s, 1H) 5.93 (br d, J=9.8 Hz, 2H) 6.62 (d, J=8.8 Hz, 1H) 7.03 (br d, J=9.5 Hz, 1H) 7.30-7.38 (m, 2H) 7.41-7.51 (m, 2H) 8.02 (s, 1H) 12.10 (br s, 1H)

LC/MS (method LC-A): R$_t$ 3.04 min, MH$^+$ 597

$[α]_D^{20}$: +23.1° (c 0.26, DMF)

Chiral SFC (method SFC-H): R$_t$ 3.22 min, MH$^+$ 597, chiral purity 100%.

Enantiomer 10B:

$^1$H NMR (500 MHz, DMSO-d6) δ ppm 1.87 (br t, J=6.8 Hz, 2H) 2.34 (br t, J=7.3 Hz, 2H) 3.12-3.25 (m, 2H) 3.63 (s, 3H) 3.80-3.90 (m, 2H) 4.05-4.14 (m, 1H) 4.38-4.49 (m, 1H) 5.71 (br d, J=9.1 Hz, 1H) 5.80 (br s, 1H) 5.94 (br d, J=9.5 Hz, 2H) 6.62 (br d, J=8.8 Hz, 1H) 7.03 (br d, J=7.9 Hz, 1H) 7.30-7.38 (m, 2H) 7.41-7.52 (m, 2H) 8.02 (br s, 1H) 12.12 (br s, 1H)

LC/MS (method LC-A): R$_t$ 3.04 min, MH$^+$ 597

$[α]_D^{20}$: −23.0° (c 0.3, DMF)

Chiral SFC (method SFC-H): R$_t$ 4.05 min, MH$^+$ 597, chiral purity 100%.

Example 11: Synthesis of 4-(3-((1-(4-chloro-2-fluorophenyl)-2-(5-methoxy-6-(trifluoromethyl)indolin-1-yl)-2-oxoethyl)amino)-5-methoxyphenoxy)butanoic Acid (Compound 11) and Chiral Separation into Enantiomers 11A and 11B

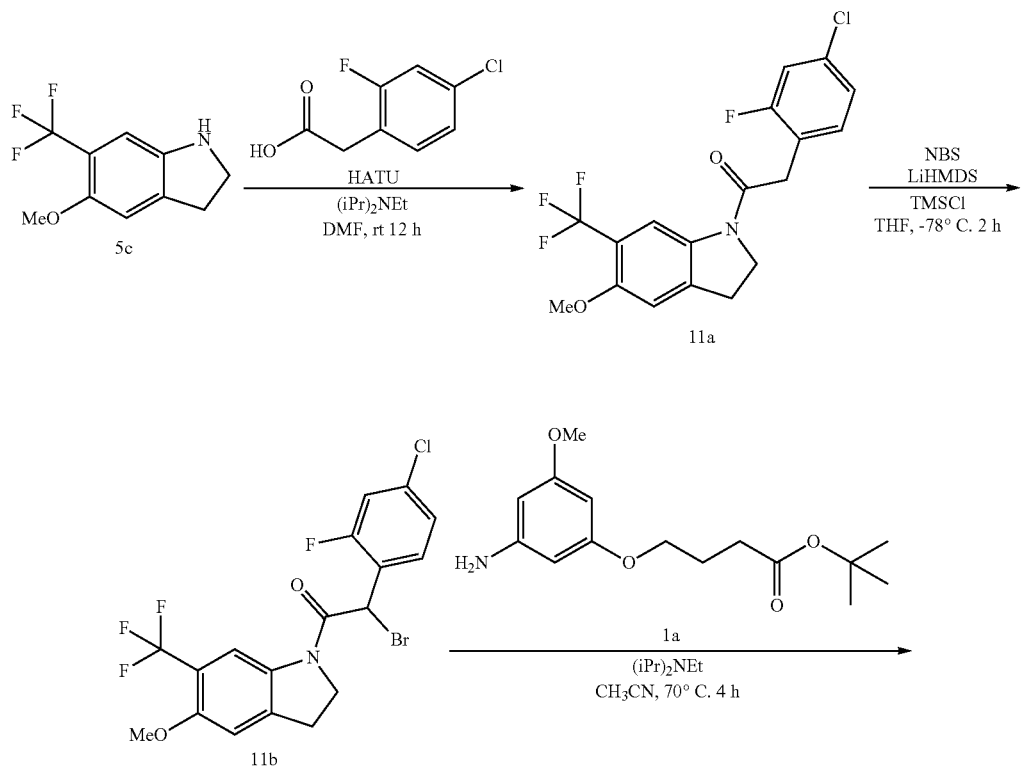

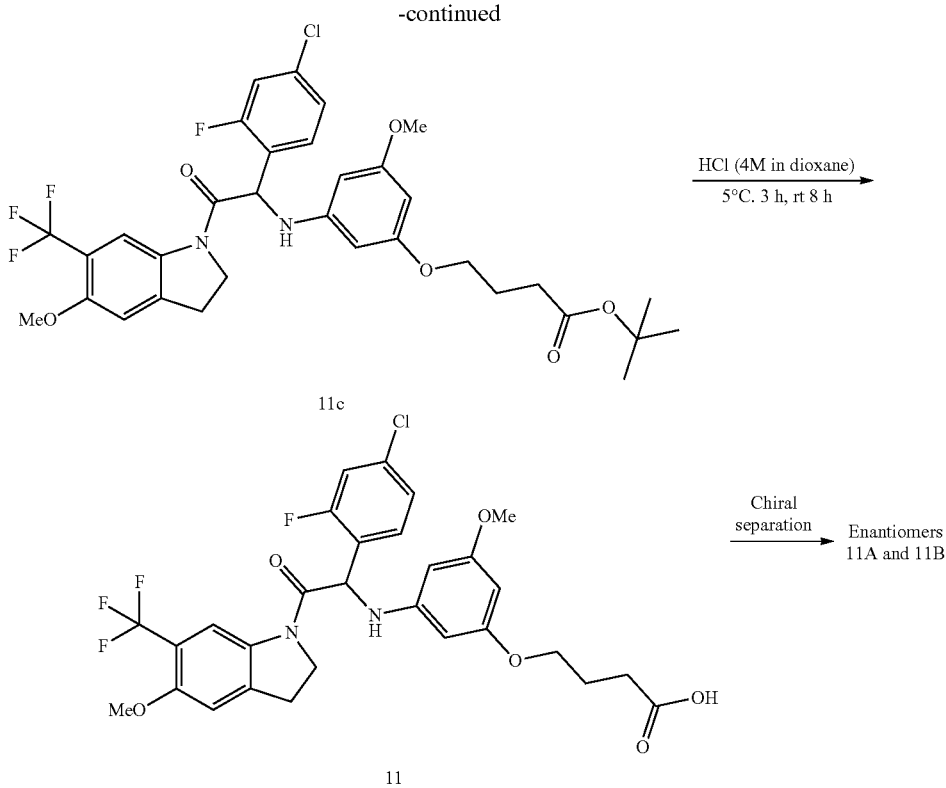

Synthesis of Intermediate 11a:

HATU (5.25 g, 13.81 mmol) was added to a mixture of 5-methoxy-6-(trifluoro-methyl)indoline 5c (2 g, 9.21 mmol), 2-(4-chloro-2-fluorophenyl)acetic acid [CAS 194240-75-0] (1.74 g, 9.21 mmol) and diisopropylethylamine (4.57 mL, 27.6 mmol) in DMF (50 mL). The resulting mixture was stirred at room temperature for 12 h. The mixture was diluted with ice/water. The precipitate was filtered off and washed with water. The residue was taken up with $CH_2Ol_2$ and the organic solution was washed with a 10% aqueous solution of $K_2CO_3$, brine, dried over $MgSO_4$, filtered and the solvent was evaporated under reduced pressure. The residue was crystallized from diisopropyl ether to give 2-(4-chloro-2-fluorophenyl)-1-(5-methoxy-6-(trifluoromethyl)indolin-1-yl)ethanone 11a (3.4 g).

Synthesis of Intermediate 11 b:

At −78° C., under a $N_2$ flow, LiHMDS 1M in THF (17.5 mL, 17.5 mmol) was added dropwise to a mixture of 2-(4-chloro-2-fluorophenyl)-1-(5-methoxy-6-(trifluoromethyl)indolin-1-yl)ethanone 11a (3.4 g, 8.77 mmol) in THF (45 mL). TMSCI (1.34 mL, 10.5 mmol) was added dropwise. The mixture was stirred for 15 min at −78° C. and a solution of N-bromoscuccinimide (1.87 g, 10.52 mmol) in THF (30 mL) was added dropwise. After stirring for 2 h at −78° C., the reaction was quenched with a saturated solution of $NH_4Cl$. The mixture was extracted with EtOAc. The organic layer was separated, dried over $MgSO_4$, filtered and the solvent was evaporated under reduced pressure to give 2-bromo-2-(4-chloro-2-fluorophenyl)-1-(5-methoxy-6-(trifluoromethyl)indolin-1-yl)ethanone 11 b (4 g). The compound was used as such in the next step.

Synthesis of Intermediate 11c:

A mixture of 2-bromo-2-(4-chloro-2-fluorophenyl)-1-(5-methoxy-6-(trifluoromethyl)-indolin-1-yl)ethanone 11b (4 g, 8.57 mmol), tert-butyl 4-(3-amino-5-methoxy-phenoxy) butanoate 1a (2.4 g, 8.57 mmol) and diisopropylethylamine (1.77 mL, 10.3 mmol) in $CH_3CN$ (100 mL) was stirred at 70° C. for 4 h. The mixture was concentrated under reduced pressure, diluted with EtOAc and washed with 1N HCl and water. The organic phase was separated, dried over $MgSO_4$, filtered and the solvent was evaporated under reduced pressure. The compound was purified by flash chromatography on silica gel (15-40 µm, 80 g, heptane/EtOAc 80/20). The compound was further purified via achiral SFC (stationary phase: 2-ethylpyridine 5 µm 150×30 mm, mobile phase: 85% $CO_2$, 15% MeOH). The pure fractions were combined and evaporated to dryness to give tert-butyl 4-(3-((1-(4-chloro-2-fluorophenyl)-2-(5-methoxy-6-(trifluoromethyl) indolin-1-yl)-2-oxoethyl)amino)-5-methoxyphenoxy)butanoate 11c (2.6 g).

Synthesis of Compound 11 and Chiral Separation into Enantiomers 11A and 11B:

A solution of tert-butyl 4-(3-((1-(4-chloro-2-fluorophenyl)-2-(5-methoxy-6-(trifluoro-methyl)indolin-1-yl)-2-oxoethyl)amino)-5-methoxyphenoxy)butanoate 11c (2.2 g, 3.3 mmol) in 4M HCl in dioxane (29.2 mL) was stirred at 5° C. for 3 h and at room temperature for 8 h. The solution was concentrated under reduced pressure. The residue was crystallized from $CH_3CN$/diisopropyl ether to afford 4-(3-((1-(4-chloro-2-fluorophenyl)-2-(5-methoxy-6-(trifluoromethyl)indolin-1-yl)-2-oxoethyl)amino)-5-methoxyphenoxy) butanoic acid (Compound 11) as an HCl salt (800 mg, 0.85 equiv. HCl, 0.36 equiv. $H_2O$). This fraction was combined with another batch (total amount: 1.8 g) for chiral separation. The enantiomers were separated via Preparative Chiral SFC (Stationary phase: Chiralcel® OD-H 5 µm 250×30 mm, Mobile phase: 55% $CO_2$, 45% iPrOH). The product fractions were combined and evaporated under reduced pressure. The first eluted enantiomer (788 mg) was solidified from petroleum ether/diisopropyl ether to give Enantiomer 11A (693 mg). The second eluted enantiomer (771 mg) was solidified from petroleum ether/diisopropyl ether to give Enantiomer 11B (695 mg).

Compound 11:
$^1$H NMR (500 MHz, DMSO-d6) δ ppm 1.87 (quin, J=6.8 Hz, 2H) 2.34 (br t, J=7.4 Hz, 2H) 3.18-3.31 (m, 2H) 3.63 (s, 3H) 3.85 (s, 5H) 3.98-4.09 (m, 1H) 4.37-4.48 (m, 1H) 5.69 (s, 1H) 5.79 (s, 1H) 5.93 (br d, J=11.0 Hz, 2H) 7.26 (s, 1H) 7.32 (br d, J=8.5 Hz, 1H) 7.44-7.52 (m, 2H) 8.32 (s, 1H)

LC/MS (method LC-A): Rt 2.90 min, MH$^+$ 611
Melting point: 121° C.

Enantiomer 11A:
$^1$H NMR (500 MHz, DMSO-d6) δ ppm 1.88 (quin, J=6.8 Hz, 2H) 2.34 (t, J=7.3 Hz, 2H) 3.18-3.29 (m, 2H) 3.63 (s, 3H) 3.86 (s, 5H) 3.99-4.07 (m, 1H) 4.38-4.47 (m, 1H) 5.69 (br s, 1H) 5.79 (s, 1H) 5.93 (br d, J=10.7 Hz, 2H) 6.55 (br s, 1H) 7.25 (s, 1H) 7.32 (dd, J=8.5, 1.3 Hz, 1H) 7.43-7.51 (m, 2H) 8.33 (s, 1H) 12.13 (br s, 1H)

LC/MS (method LC-A): $R_t$ 2.90 min, MH$^+$ 611
$[α]_D^{20}$: −23.9° (c 0.26, DMF) Chiral SFC (method SFC-C): $R_t$ 1.70 min, MH$^+$ 611, chiral purity 100%.

Enantiomer 11B:
$^1$H NMR (500 MHz, DMSO-d6) δ ppm 1.88 (quin, J=6.8 Hz, 2H) 2.34 (br t, J=7.3 Hz, 2H) 3.18-3.31 (m, 2H) 3.63 (s, 3H) 3.85 (s, 5H) 3.99-4.07 (m, 1H) 4.37-4.47 (m, 1H) 5.69 (br s, 1H) 5.79 (s, 1H) 5.93 (br d, J=11.0 Hz, 2H) 6.56 (br s, 1H) 7.25 (s, 1H) 7.32 (br d, J=8.2 Hz, 1H) 7.43-7.50 (m, 2H) 8.33 (s, 1H) 12.13 (br s, 1H)

LC/MS (method LC-A): $R_t$ 2.89 min, MH$^+$ 611
$[α]_D^{20}$: +24.0° (c 0.25, DMF)
Chiral SFC (method SFC-C): $R_t$ 2.96 min, MH$^+$ 611, chiral purity 100%.

Example 12: Synthesis of 4-(3-((1-(4-chlorophenyl)-2-(5-methoxy-6-(trifluoro-methoxy)indolin-1-yl)-2-oxoethyl)amino)-5-methoxyphenoxy)butanoic Acid (Compound 12) and Chiral Separation into Enantiomers 12A and 12B

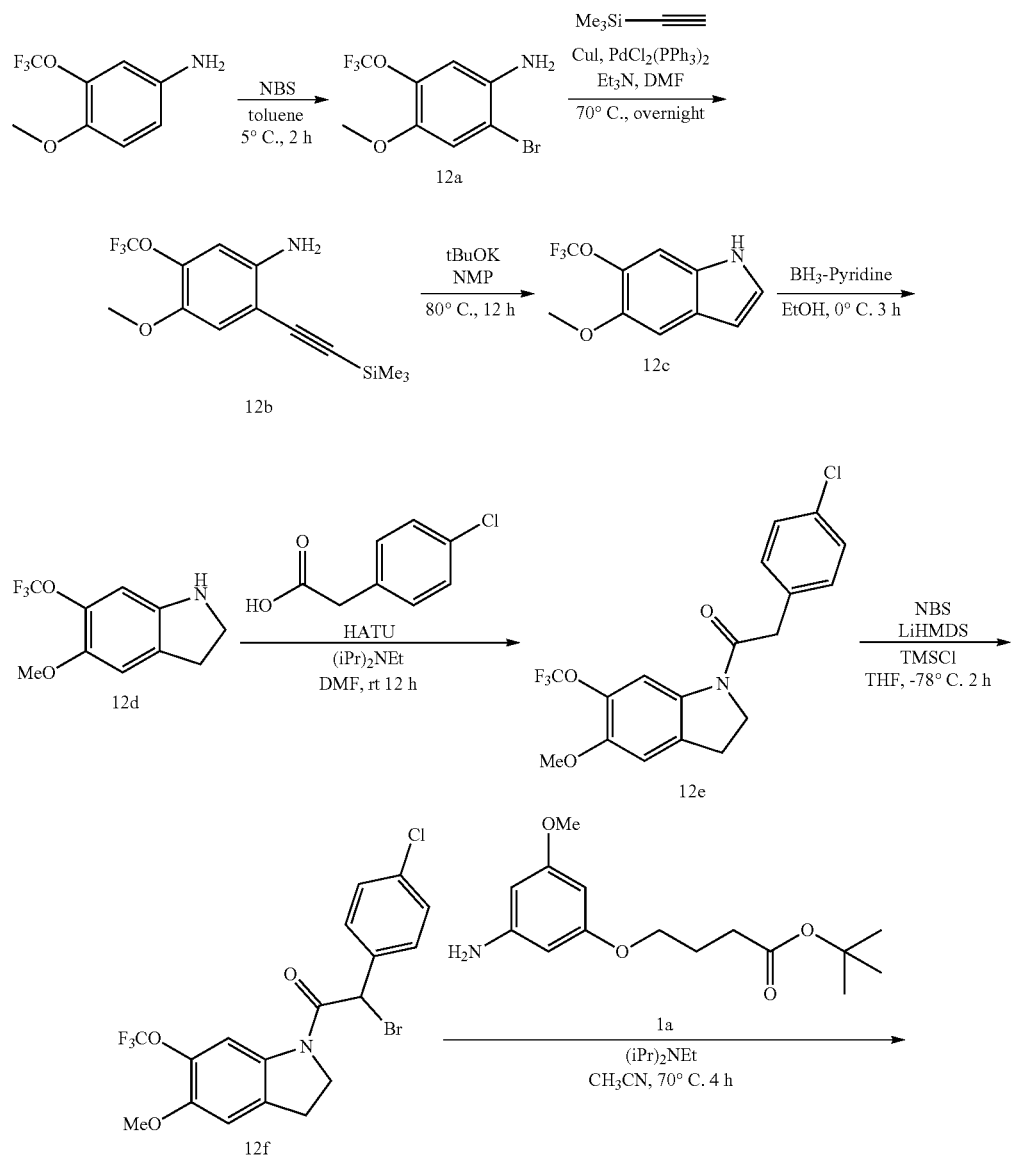

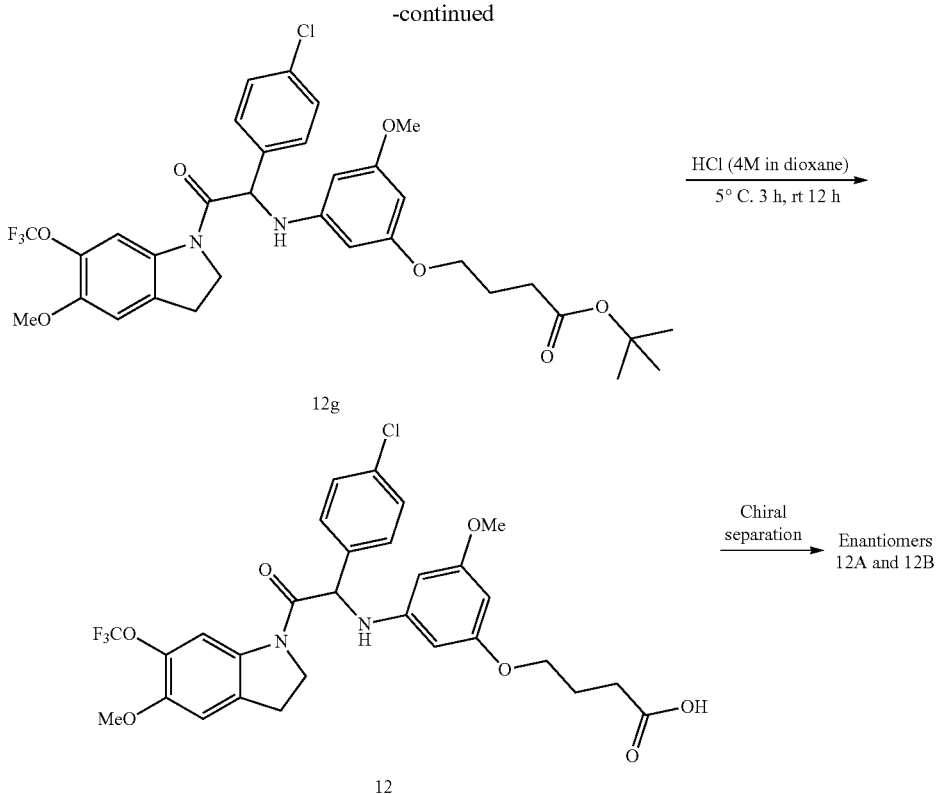

12g

12

Synthesis of Intermediate 12a:

A solution of 4-methoxy-3-(trifluoromethoxy)aniline [CAS 647855-21-8] (3.1 g, 15.0 mmol) in toluene (50 mL) was treated with N-bromosuccinimide (2.8 g, 15.7 mmol) at 5° C. and the resulting mixture was stirred at 5-10° C. for 2 h. The mixture was quenched with water and extracted with EtOAc. The combined extracts were dried over MgSO$_4$, filtered and evaporated under reduced pressure. Purification was done by flash chromatography on silica gel (15-40 μm, 24 g, heptane/EtOAc gradient 95/5 to 90/10) The pure fractions were combined and evaporated to dryness to give 2-bromo-4-methoxy-5-(trifluoromethoxy)aniline 12a (2.5 g).

Synthesis of Intermediate 12b:

A solution of 2-bromo-4-methoxy-5-(trifluoromethoxy)aniline 12a (2.72 g, 9.51 mmol) in DMF (30 mL) was degassed with N$_2$ for 15 min. Dichlorobis-(triphenylphosphine)palladium (667 mg, 0.95 mmol), copper(I) iodide (362 mg, 1.90 mmol), triethylamine (3.96 mL, 28.5 mmol) and trimethylsilylacetylene (3.95 mL, 28.53 mmol) were added. The reaction mixture was heated at 70° C. for 12 h under N$_2$ flow. After cooling to room temperature, the reaction mixture was diluted with H$_2$O and extracted with EtOAc. The organic phases were combined, dried over MgSO$_4$, filtered and concentrated under reduced pressure. The residue was purified by flash chromatography on silica gel (15-40 μm, 80 g, heptane/EtOAc 85/15). The pure fractions were combined and evaporated to dryness to give 4-methoxy-5-(trifluoromethoxy)-2-((trimethylsilyl)ethynyl)aniline 12b (1.4 g).

Synthesis of Intermediate 12c:

To a solution of 4-methoxy-5-(trifluoromethoxy)-2-((trimethylsilyl)ethynyl)aniline 12b (1.2 g, 3.96 mmol) in NMP (11 mL) under N$_2$ flow was added tBuOK (1.33 g, 11.9 mmol) in one portion. The reaction mixture was heated at 80° C. for 4 h; after cooling to room temperature, the mixture was poured into ice/water and acidified with 3N HCl until pH 4-5. The reaction mixture was extracted with EtOAc. The organic phases were combined, washed with H$_2$O, dried over MgSO$_4$, filtered and concentrated under reduced pressure. The residue was purified by flash chromatography on silica gel (15-40 μm, 40 g, heptane/EtOAc 85/15). The pure fractions were combined and evaporated to dryness to give 5-methoxy-6-(trifluoromethoxy)-1H-indole 12c (490 mg).

Synthesis of Intermediate 12d:

At 0° C., BH$_3$—Pyridine (10.5 mL, 103.8 mmol) was added dropwise to a solution of 5-methoxy-6-(trifluoromethoxy)-1H-indole 12c (8 g, 34.6 mmol) in EtOH (45 mL). 6N HCl (6 mL) was slowly added while maintaining the temperature below 10° C. The mixture was stirred at 0° C. for 3 h. Water (210 mL) was added and the mixture was basified until pH 8-9 with a concentrated solution of NaOH in water (during the addition, the reaction temperature was kept below 20° C.). The mixture was extracted with EtOAc. The organic layer was washed with water, dried over MgSO$_4$, filtered and the solvent was evaporated under reduced pressure. Toluene was added and the solution was concentrated under reduced pressure to give 7.5 g of 5-methoxy-6-(trifluoromethoxy)indoline 12d.

Synthesis of Intermediate 12e:

A mixture of 5-methoxy-6-(trifluoromethoxy)indoline 12d (1 g, 4.29 mmol), 2-(4-chlorophenyl)acetic acid [CAS 1878-66-6] (805 mg, 4.72 mmol), HATU (2.44 g, 6.43 mmol) and diisopropylethylamine (2.13 mL, 12.87 mmol) in DMF (20 mL) was stirred at room temperature for 12 h. Ice/water was added and the precipitate was filtered off. The residue was taken up with CH$_2$Cl$_2$. The organic solution was separated, dried over MgSO₄, filtered and the solvent was evaporated under reduced pressure to give 2-(4-chlorophenyl)-1-(5-methoxy-6-(trifluoromethoxy)indolin-1-yl)ethanone 12e (1.68 g).

Synthesis of Intermediate 12f:

At −78° C., under a N₂ flow, LiHMDS 1M in THF (8.3 mL, 8.3 mmol) was added dropwise to a mixture of 2-(4-chlorophenyl)-1-(5-methoxy-6-(trifluoromethoxy)-indolin-1-yl)ethanone 12e (1.6 g, 4.15 mmol) in THF (25 mL). TMSCI (0.63 mL, 4.98 mmol) was added dropwise. The mixture was stirred for 15 min at −78° C. and a solution of N-bromosuccinimide (0.89 g, 4.98 mmol) in THF (15 mL) was added dropwise. After stirring for 2 h at −78° C., the reaction was quenched with a saturated solution of NH₄Cl. The mixture was extracted with EtOAc. The organic layer was separated, dried over MgSO₄, filtered and the solvent was evaporated under reduced pressure to give 2-bromo-2-(4-chlorophenyl)-1-(5-methoxy-6-(trifluoromethoxy)indolin-1-yl)ethanone 12f (2.3 g, purity (by LC): 50%). The compound was used as such in the next step.

Synthesis of Intermediate 12g:

A mixture of 2-bromo-2-(4-chlorophenyl)-1-(5-methoxy-6-(trifluoromethoxy)indolin-1-yl)ethanone 12f (2.3 g, 2.48 mmol, purity (by LC): 50%), tert-butyl 4-(3-amino-5-methoxyphenoxy)butanoate 1a (0.696 g, 2.48 mmol) and diisopropylethylamine (0.512 mL, 2.97 mmol) in CH₃CN (25 mL) was stirred at 70° C. for 4 h. The mixture was concentrated under reduced pressure, diluted with EtOAc, and washed with 1N HCl, and water. The organic phase was separated, dried over MgSO₄, filtered and the solvent was evaporated under reduced pressure. The residue was purified by flash chromatography on silica gel (15-40 μm, 80 g, heptane/EtOAc 80/20). The fractions containing product were combined and evaporated under reduced pressure and the residue was purified again by flash chromatography on silica gel (15-40 μm, 40 g, CH₂Cl₂). The pure fractions were combined and evaporated to dryness to give tert-butyl 4-(3-((1-(4-chlorophenyl)-2-(5-methoxy-6-(trifluoromethoxy)indolin-1-yl)-2-oxoethyl)amino)-5-methoxyphenoxy)butanoate 12g (920 mg).

Synthesis of Compound 12 and Chiral Separation into Enantiomers 12A and 12B:

A solution of tert-butyl 4-(3-((1-(4-chlorophenyl)-2-(5-methoxy-6-(trifluoromethoxy)-indolin-1-yl)-2-oxoethyl)amino)-5-methoxyphenoxy)butanoate 12g (920 mg, 1.38 mmol) in 4M HCl in dioxane (15 mL) was stirred at 5° C. for 3 h and at room temperature for 12 h. The precipitate was filtered off, washed with diisopropyl ether and dried to afford 4-(3-((1-(4-chlorophenyl)-2-(5-methoxy-6-(trifluoromethoxy)indolin-1-yl)-2-oxoethyl)amino)-5-methoxyphenoxy)butanoic acid (Compound 12, 802 mg, 0.2 equiv. H₂O). The enantiomers were separated via Preparative Chiral SFC (Stationary phase: Chiralpak® AD-H 5 μm 250×20 mm, Mobile phase: 50% CO₂, 50% iPrOH). The product fractions were combined and evaporated under reduced pressure. The first eluted enantiomer (260 mg) was solidified from heptane/diisopropyl ether to give Enantiomer 12A (165 mg). The second eluted enantiomer (241 mg) was solidified from heptane/diisopropyl ether to give Enantiomer 12B (184 mg).

Compound 12:

¹H NMR (500 MHz, DMSO-d6) δ ppm 1.86 (quin, J=6.9 Hz, 2H) 2.33 (t, J=7.3 Hz, 2H) 3.08-3.28 (m, 2H) 3.61 (s, 3H) 3.81 (s, 3H) 3.84 (br t, J=6.5 Hz, 2H) 3.97-4.06 (m, 1H) 4.48 (td, J=10.4, 6.3 Hz, 1H) 5.53 (s, 1H) 5.75 (s, 1H) 5.94 (br d, J=10.1 Hz, 2H) 7.20 (s, 1H) 7.43 (d, J=8.5 Hz, 2H) 7.54 (d, J=8.5 Hz, 2H) 8.06 (s, 1H)

LC/MS (method LC-A): Rt 2.89 min, MH⁺ 609

Enantiomer 12A:

¹H NMR (500 MHz, DMSO-d6) δ ppm 1.86 (quin, J=6.8 Hz, 2H) 2.33 (t, J=7.3 Hz, 2H) 3.09-3.26 (m, 2H) 3.61 (s, 3H) 3.81 (s, 3H) 3.84 (br t, J=6.5 Hz, 2H) 4.02 (td, J=10.3, 7.1 Hz, 1H) 4.48 (td, J=10.4, 6.3 Hz, 1H) 5.53 (d, J=8.5 Hz, 1H) 5.75 (s, 1H) 5.93 (s, 1H) 5.95 (s, 1H) 6.43 (d, J=8.8 Hz, 1H) 7.20 (s, 1H) 7.43 (d, J=8.2 Hz, 2H) 7.55 (d, J=8.5 Hz, 2H) 8.06 (s, 1H) 12.12 (br s, 1H)

LC/MS (method LC-A): $R_t$ 2.92 min, MH⁺ 609

$[\alpha]_D^{20}$: −44.2° (c 0.197, DMF)

Chiral SFC (method SFC-I): $R_t$ 0.99 min, MH⁺ 609, chiral purity 100%.

Enantiomer 12B:

¹H NMR (500 MHz, DMSO-d6) δ ppm 1.86 (quin, J=6.9 Hz, 2H) 2.33 (t, J=7.3 Hz, 2H) 3.09-3.27 (m, 2H) 3.61 (s, 3H) 3.81 (s, 3H) 3.84 (br t, J=6.5 Hz, 2H) 3.98-4.06 (m, 1H) 4.48 (td, J=10.5, 6.1 Hz, 1H) 5.53 (d, J=8.8 Hz, 1H) 5.75 (s, 1H) 5.93 (s, 1H) 5.95 (s, 1H) 6.43 (d, J=8.8 Hz, 1H) 7.20 (s, 1H) 7.43 (d, J=8.5 Hz, 2H) 7.54 (d, J=8.5 Hz, 2H) 8.06 (s, 1H) 12.16 (br s, 1H)

LC/MS (method LC-A): $R_t$ 2.91 min, MH⁺ 609

$[\alpha]_D^{20}$: +40.7° (c 0.189, DMF)

Chiral SFC (method SFC-I): $R_t$ 1.45 min, MH⁺ 609, chiral purity 98.53%.

TABLE compounds prepared as described above

| Compound | Structure | Optical rotation |
|---|---|---|
| 1 | 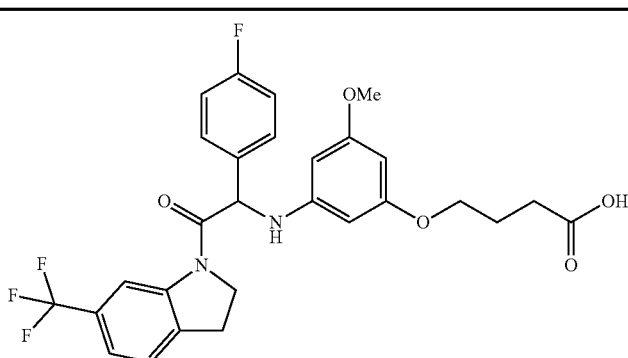 | racemic |

TABLE-continued compounds prepared as described above

| Compound | Structure | Optical rotation |
|---|---|---|
| 1A | (structure: (−)-enantiomer with 4-fluorophenyl, OMe-substituted phenoxybutanoic acid, 6-trifluoromethyl indoline amide) | $[\alpha]_D^{20} = -49.0°$ |
| 1B | (structure: (+)-enantiomer with 4-fluorophenyl, OMe-substituted phenoxybutanoic acid, 6-trifluoromethyl indoline amide) | $[\alpha]_D^{20} = +49.5°$ |
| 2 | (structure: racemic with 4-fluorophenyl, OMe-substituted phenoxybutanoic acid, 6-trifluoromethoxy indoline amide) | racemic |
| 2A | (structure: (−)-enantiomer with 4-fluorophenyl, OMe-substituted phenoxybutanoic acid, 6-trifluoromethoxy indoline amide) | $[\alpha]_D^{20} = -46.3°$ |

TABLE-continued compounds prepared as described above

| Compound | Structure | Optical rotation |
|---|---|---|
| 2B | 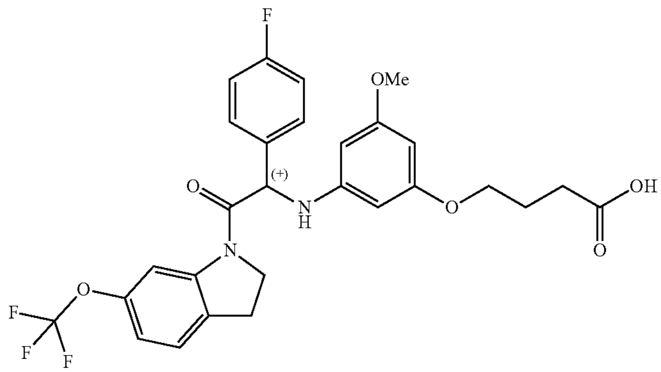 [SMILES: COc1cc(NC(C(=O)N2CCc3ccc(OC(F)(F)F)cc32)c2ccc(F)cc2)cc(OCCCC(=O)O)c1] | $[\alpha]_D^{20} = +47.0°$ |
| 3 | 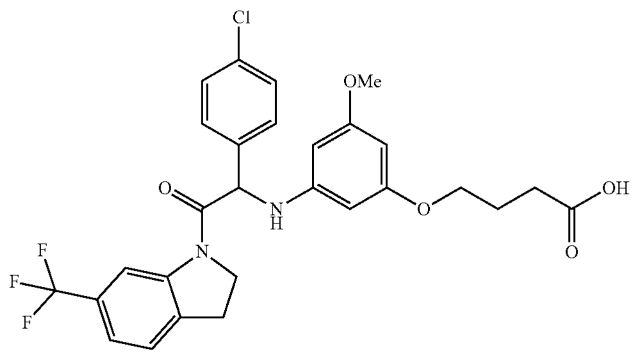 [SMILES: COc1cc(NC(C(=O)N2CCc3ccc(C(F)(F)F)cc32)c2ccc(Cl)cc2)cc(OCCCC(=O)O)c1] | racemic |
| 3A | 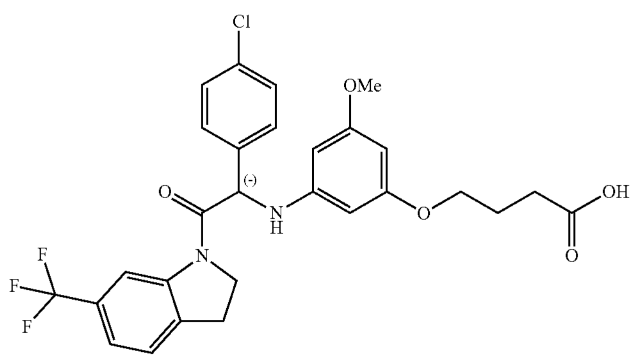 | $[\alpha]_D^{20} = -42.4°$ |
| 3B | 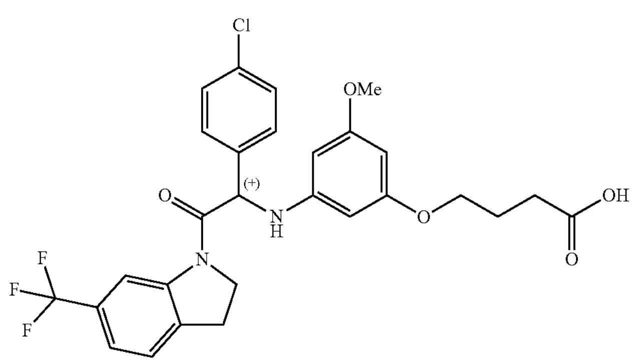 [SMILES: COc1cc(NC(C(=O)N2CCc3ccc(C(F)(F)F)cc32)c2ccc(Cl)cc2)cc(OCCCC(=O)O)c1] | $[\alpha]_D^{20} = +50.7°$ |

TABLE-continued compounds prepared as described above

| Compound | Structure | Optical rotation |
| --- | --- | --- |
| 4 | 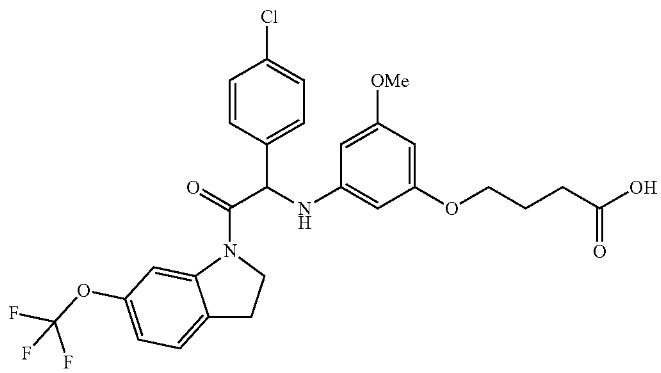 [SMILES: COc1cc(NC(C(=O)N2CCc3ccc(OC(F)(F)F)cc32)c2ccc(Cl)cc2)cc(OCCCC(=O)O)c1] | racemic |
| 4A | 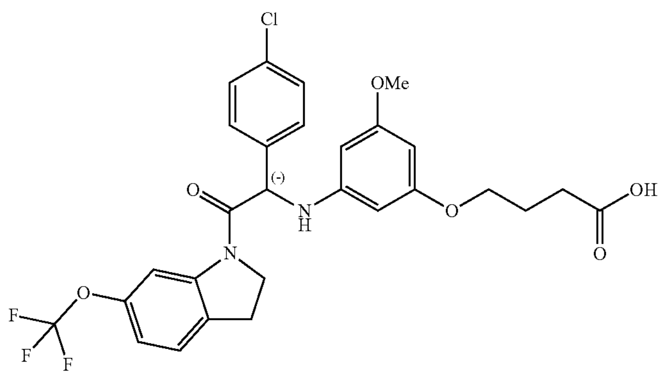 | $[\alpha]_D^{20} = -48.5°$ |
| 4B | 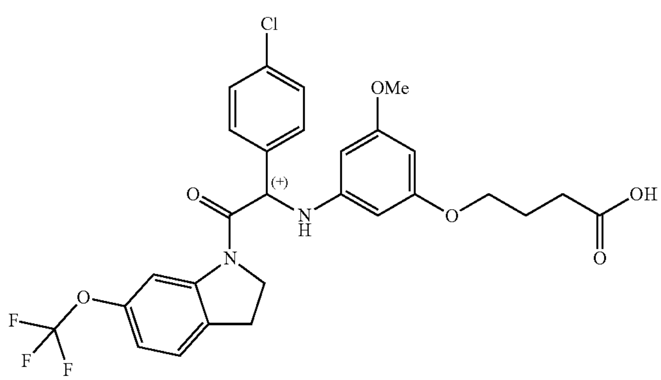 | $[\alpha]_D^{20} = +42.9°$ |
| 5 | 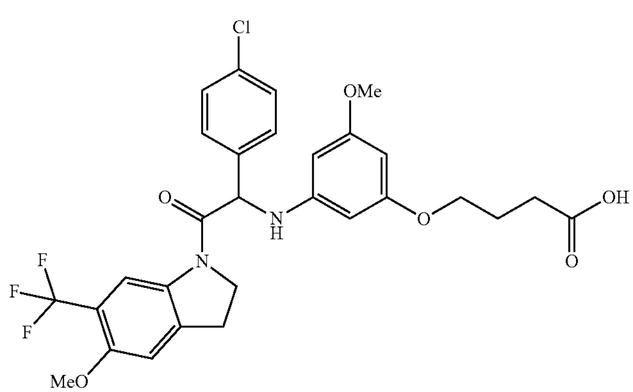 [SMILES: COc1cc(NC(C(=O)N2CCc3cc(OC)c(C(F)(F)F)cc32)c2ccc(Cl)cc2)cc(OCCCC(=O)O)c1] | racemic |

TABLE-continued compounds prepared as described above

| Compound | Structure | Optical rotation |
|---|---|---|
| 5A | 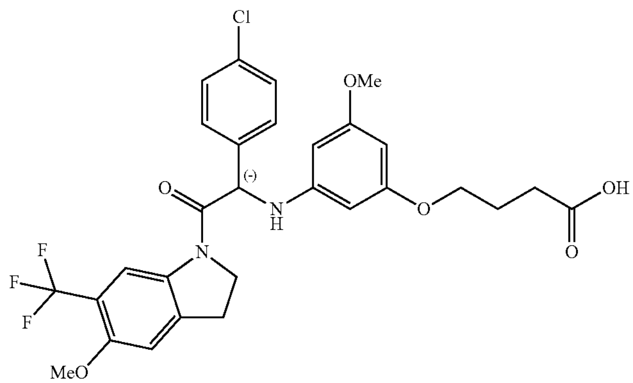 [SMILES: COc1cc(NC(C(=O)N2CCc3cc(OC)c(C(F)(F)F)cc32)c2ccc(Cl)cc2)cc(OCCCC(=O)O)c1] | $[\alpha]_D^{20} = -43.2°$ |
| 5B | 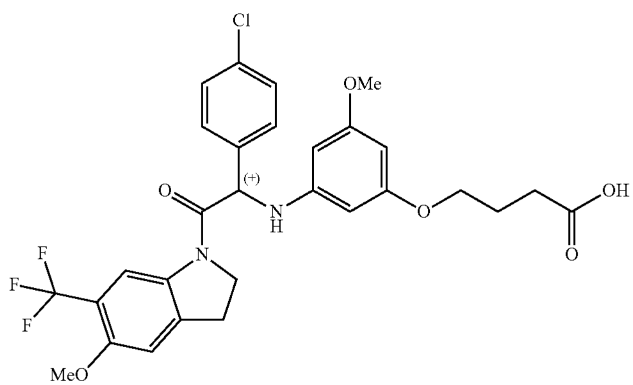 [SMILES: COc1cc(NC(C(=O)N2CCc3cc(OC)c(C(F)(F)F)cc32)c2ccc(Cl)cc2)cc(OCCCC(=O)O)c1] | $[\alpha]_D^{20} = +41.4°$ |
| 6 | 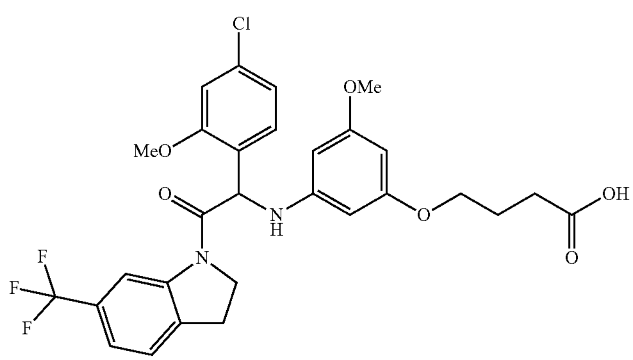 [SMILES: COc1cc(NC(C(=O)N2CCc3ccc(C(F)(F)F)cc32)c2ccc(Cl)cc2OC)cc(OCCCC(=O)O)c1] | racemic |
| 6A | 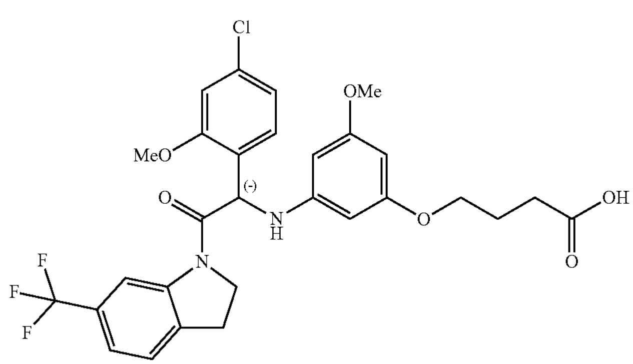 [SMILES: COc1cc(NC(C(=O)N2CCc3ccc(C(F)(F)F)cc32)c2ccc(Cl)cc2OC)cc(OCCCC(=O)O)c1] | $[\alpha]_D^{20} = -28.6°$ |

TABLE-continued compounds prepared as described above

| Compound | Structure | Optical rotation |
|---|---|---|
| 6B | [structure] | $[\alpha]_D^{20} = +32.1°$ |
| 7 | [structure] | racemic |
| 7A | [structure] | $[\alpha]_D^{20} = -23.9°$ |
| 7B | [structure] | $[\alpha]_D^{20} = +28.5°$ |

TABLE-continued compounds prepared as described above

| Compound | Structure | Optical rotation |
|---|---|---|
| 8 | 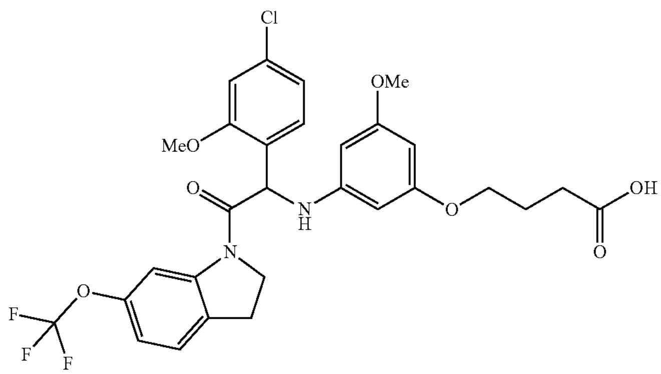 [SMILES: COc1cc(NC(C(=O)N2CCc3ccc(OC(F)(F)F)cc32)c2ccc(Cl)cc2OC)cc(OCCCC(=O)O)c1] | racemic |
| 8A | 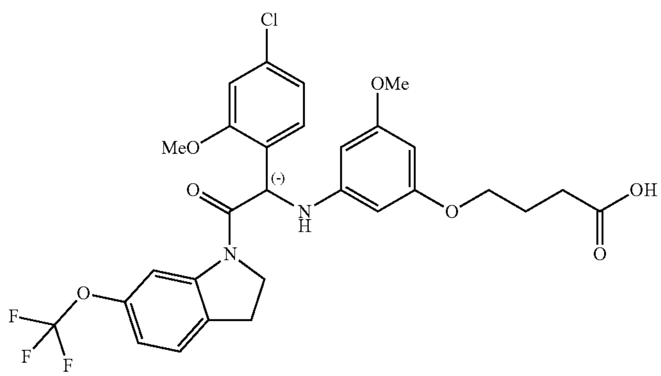 [SMILES: COc1cc(NC(C(=O)N2CCc3ccc(OC(F)(F)F)cc32)c2ccc(Cl)cc2OC)cc(OCCCC(=O)O)c1] | $[\alpha]_D^{20} = -39.3°$ |
| 8B | 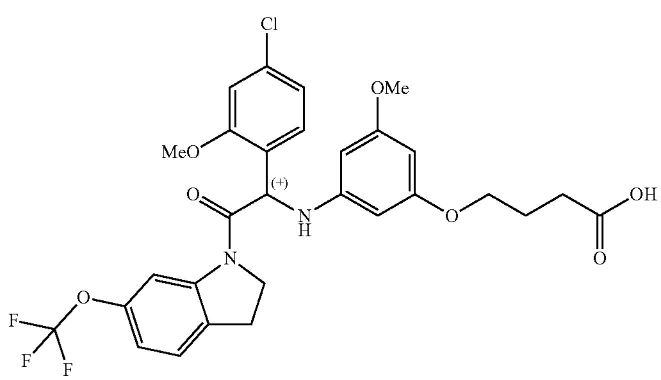 [SMILES: COc1cc(NC(C(=O)N2CCc3ccc(OC(F)(F)F)cc32)c2ccc(Cl)cc2OC)cc(OCCCC(=O)O)c1] | $[\alpha]_D^{20} = +34.5°$ |
| 9 | 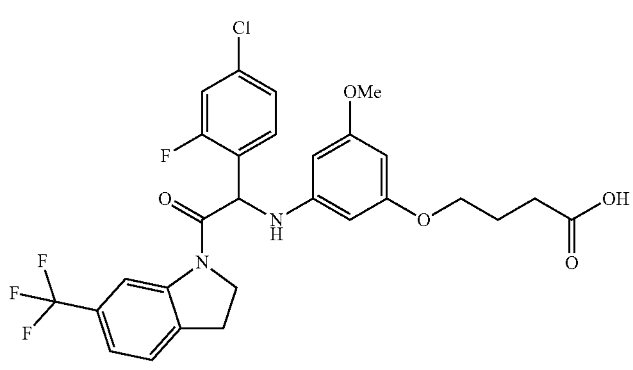 [SMILES: COc1cc(NC(C(=O)N2CCc3ccc(C(F)(F)F)cc32)c2ccc(Cl)cc2F)cc(OCCCC(=O)O)c1] | racemic |

TABLE-continued compounds prepared as described above

| Compound | Structure | Optical rotation |
|---|---|---|
| 9A | 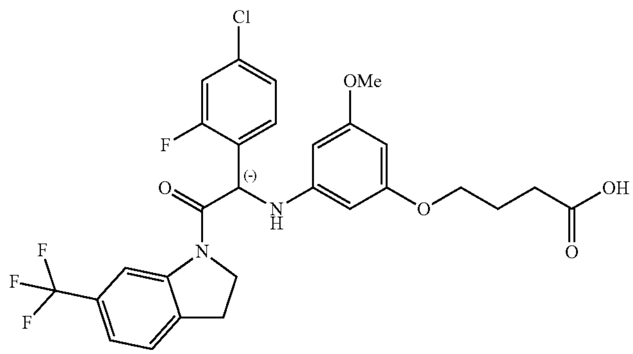 [SMILES: COc1cc(NC(C(=O)N2CCc3ccc(C(F)(F)F)cc32)c2ccc(Cl)cc2F)cc(OCCCC(=O)O)c1] | $[\alpha]_D^{20} = -30.0°$ |
| 9B | 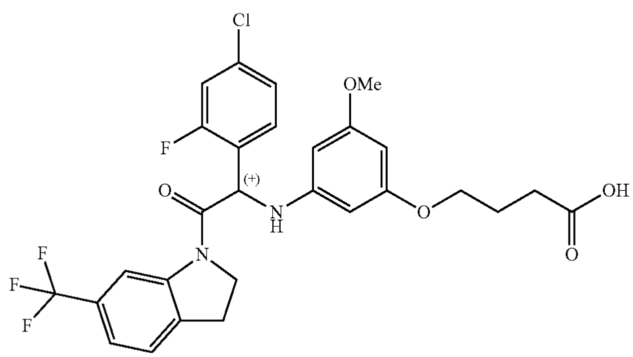 [SMILES: COc1cc(NC(C(=O)N2CCc3ccc(C(F)(F)F)cc32)c2ccc(Cl)cc2F)cc(OCCCC(=O)O)c1] | $[\alpha]_D^{20} = +27.9°$ |
| 10 | 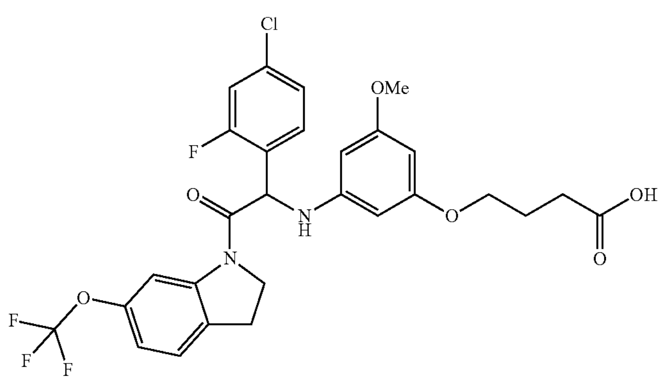 [SMILES: COc1cc(NC(C(=O)N2CCc3ccc(OC(F)(F)F)cc32)c2ccc(Cl)cc2F)cc(OCCCC(=O)O)c1] | racemic |
| 10A | 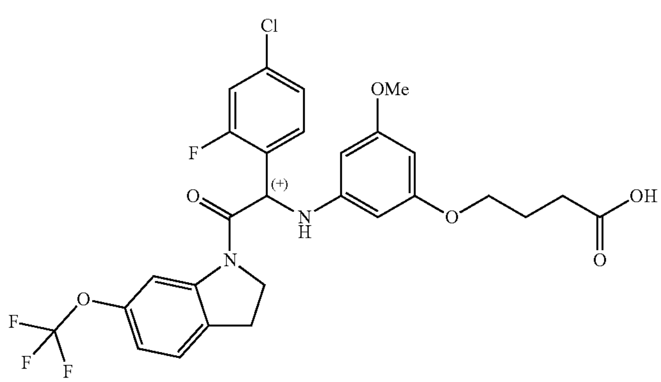 | $[\alpha]_D^{20} = +23.1°$ |

TABLE-continued compounds prepared as described above

| Compound | Structure | Optical rotation |
|---|---|---|
| 10B | 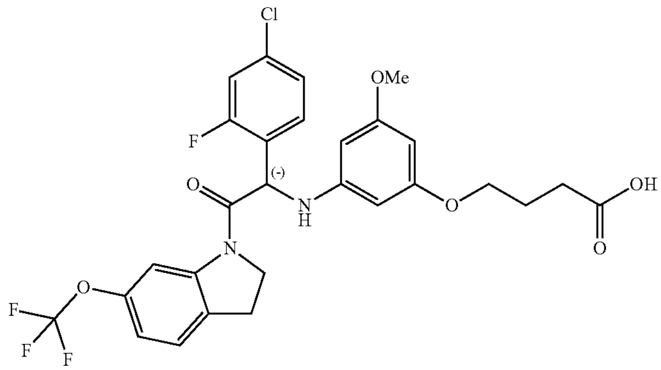 [SMILES: COc1cc(NC(C(=O)N2CCc3ccc(OC(F)(F)F)cc32)c2ccc(Cl)cc2F)cc(OCCCC(=O)O)c1] | $[\alpha]_D^{20} = -23.0°$ |
| 11 | 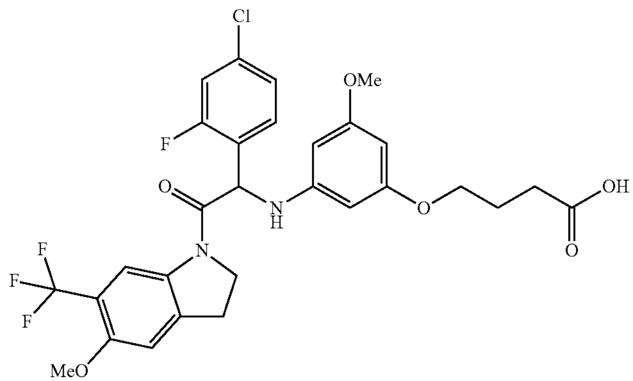 [SMILES: COc1cc(NC(C(=O)N2CCc3cc(OC)c(C(F)(F)F)cc32)c2ccc(Cl)cc2F)cc(OCCCC(=O)O)c1] | racemic |
| 11A | 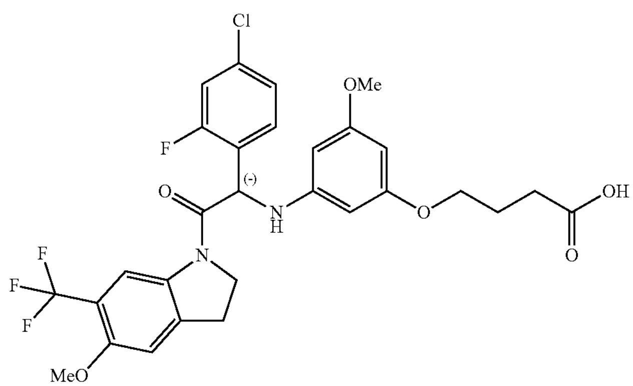 [SMILES: COc1cc(NC(C(=O)N2CCc3cc(OC)c(C(F)(F)F)cc32)c2ccc(Cl)cc2F)cc(OCCCC(=O)O)c1] | $[\alpha]_D^{20} = -23.9°$ |
| 11B | 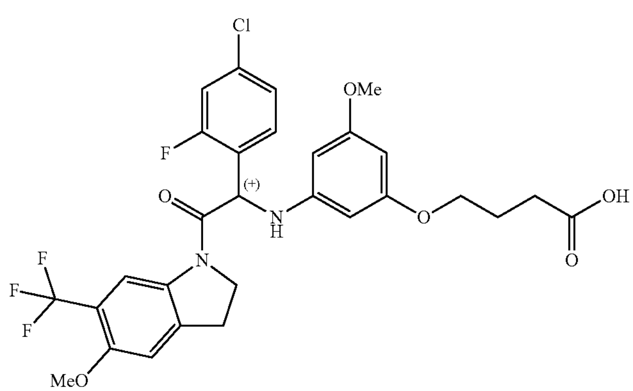 [SMILES: COc1cc(NC(C(=O)N2CCc3cc(OC)c(C(F)(F)F)cc32)c2ccc(Cl)cc2F)cc(OCCCC(=O)O)c1] | $[\alpha]_D^{20} = +24.0°$ |

TABLE-continued compounds prepared as described above

| Compound | Structure | Optical rotation |
|---|---|---|
| 12 | 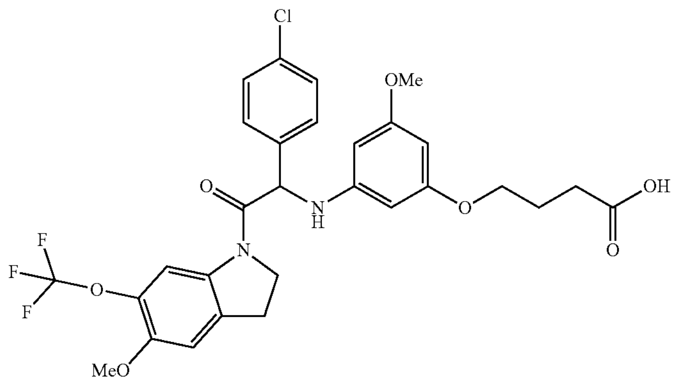 [SMILES: COc1cc(NC(C(=O)N2CCc3cc(OC)c(OC(F)(F)F)cc32)c2ccc(Cl)cc2)cc(OCCCC(=O)O)c1] | racemic |
| 12A | 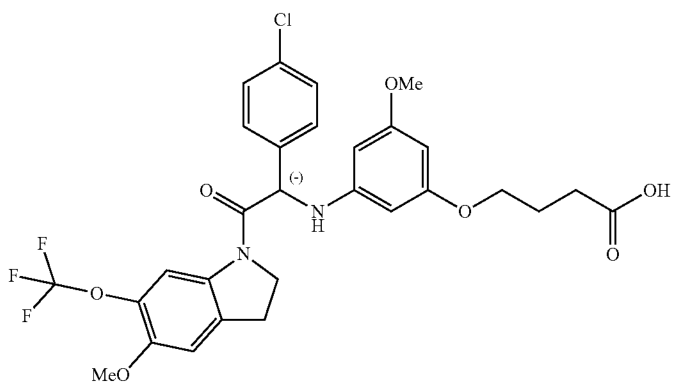 [SMILES: COc1cc(NC(C(=O)N2CCc3cc(OC)c(OC(F)(F)F)cc32)c2ccc(Cl)cc2)cc(OCCCC(=O)O)c1] | $[\alpha]_D^{20} = -44.2°$ |
| 12B | 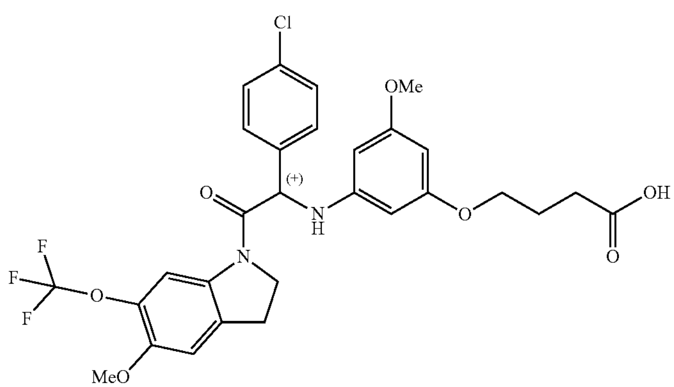 [SMILES: COc1cc(NC(C(=O)N2CCc3cc(OC)c(OC(F)(F)F)cc32)c2ccc(Cl)cc2)cc(OCCCC(=O)O)c1] | $[\alpha]_D^{20} = +40.7°$ |

Antiviral Activity of the Compounds of the Invention

DENV-2 Antiviral Assay

The antiviral activity of all the compounds of the invention was tested against the DENV-2 16681 strain which was labeled with enhanced green fluorescent protein (eGPF). The culture medium consists of minimal essential medium supplemented with 2% of heat-inactivated fetal calf serum, 0.04% gentamycin (50 mg/mL) and 2 mM of L-glutamine. Vero cells, obtained from ECACC, were suspended in culture medium and 25 μL was added to 384-well plates (2500 cells/well), which already contain the antiviral compounds. Typically, these plates contain a 5-fold serial dilution of 9 dilution steps of the test compound at 200 times the final concentration in 100% DMSO (200 nL). In addition, each compound concentration is tested in quadruplicate (final concentration range: 25 μM-0.000064 μM or 2.5 μM-0.0000064 μM for the most active compounds). Finally, each plate contains wells which are assigned as virus controls (containing cells and virus in the absence of compound), cell controls (containing cells in the absence of virus and compound) and medium controls (containing medium in the absence of cells, virus and compounds). To the wells assigned as medium control, 25 μL of culture medium was added instead of Vero cells. Once the cells were added to the plates, the plates were incubated for 30 minutes at room temperature to allow the cells to distribute evenly within the wells. Next, the plates were incubated in a fully humidified incubator (37° C., 5% $CO_2$) until the next day. Then, DENV-2 strain 16681, labeled with eGFP, was added at a multiplicity of infection (MOI) of 0.5. Therefore, 15 μL of virus suspension was added to all the wells containing test compound and to the wells assigned as virus control. In parallel, 15 μL of culture medium was added to the medium and cell controls. Next, the plates were incubated for 3 days in a fully humidified incubator (37° C., 5% $CO_2$). At the day of the read out, the eGFP fluorescence was measured using an automated fluorescence microscope at 488 nm (blue laser). Using an in-house LIMS system, inhibition dose response curves for each compound were calculated and the half maximal effective concentration ($EC_{50}$) was determined. Therefore, the percent inhibition (I) for every test concentration is calculated using the following formula: $I=100*(S_T-S_{CC})/(S_{VC}-S_{CC})$; $S_T$, $S_{CC}$ and $S_{VC}$ are the amount of eGFP signal in the test compound, cell control and virus control wells, respectively. The $EC_{50}$, represents the concentration of a compound at which the virus replication is inhibited with 50%, as measured by a 50% reduction of the eGFP fluorescent intensity compared to the virus control. The $EC_{50}$ is calculated using linear interpolation (Table 1).

In parallel, the toxicity of the compounds was assessed on the same plates. Once the read-out for the eGFP signal was done, 40 μL of ATPlite, a cell viability stain, was added to all wells of the 384-well plates. ATP is present in all metabolically active cells and the concentration declines very rapidly when the cells undergo necrosis or apoptosis. The ATPLite assay system is based on the production of light caused by the reaction of ATP with added luciferase and D-luciferin. The plates were incubated for 10 minutes at room temperature. Next, the plates were measured on a ViewLux. The half maximal cytotoxic concentration ($CC_{50}$) was also determined, defined as the concentration required to reduce the luminescent signal by 50% compared to that of the cell control wells. Finally, the selectivity index (SI) was determined for the compounds, which was calculated as followed: $SI=CC_{50}/EC_{50}$.

TABLE 1

$EC_{50}$, $CC_{50}$, and SI for the compounds of the invention in the DENV-2 antiviral assay

| compound# | $EC_{50}$ (μM) | N | $CC_{50}$ (μM) | N | SI | N |
|---|---|---|---|---|---|---|
| 1 | 0.0021 | 4 | >25 | 4 | >12022 | 4 |
| 1A | 0.18 | 3 | >25 | 3 | >76 | 3 |
| 1B | 0.00084 | 3 | 20 | 3 | 26500 | 3 |
| 2 | 0.00055 | 3 | 12 | 4 | 22200 | 3 |
| 2A | 0.056 | 3 | 14 | 3 | 248 | 3 |
| 2B | 0.00024 | 3 | 20 | 3 | 214720 | 3 |
| 3 | 0.00048 | 3 | 13 | 5 | 20300 | 3 |
| 3A | 0.0039 | 6 | 11 | 7 | 3200 | 6 |
| 3B | 0.00014 | 8 | 13 | 8 | 111100 | 8 |
| 4 | 0.00015 | 4 | 10 | 4 | >46100 | 4 |
| 4A | 0.031 | 7 | 10 | 8 | 345 | 7 |

TABLE 1-continued $EC_{50}$, $CC_{50}$, and SI for the compounds of the invention in the DENV-2 antiviral assay

| compound# | $EC_{50}$ (μM) | N | $CC_{50}$ (μM) | N | SI | N |
|---|---|---|---|---|---|---|
| 4B | 0.00012 | 23 | 13 | 23 | 92400 | 23 |
| 5 | 0.00062 | 3 | 13 | 3 | 26000 | 3 |
| 5A | 0.019 | 3 | 12 | 3 | 625 | 3 |
| 5B | 0.00018 | 3 | 13 | 3 | 87500 | 3 |
| 6 | 0.00031 | 6 | 12 | 7 | 32100 | 6 |
| 6A | 0.023 | 3 | 12 | 3 | 527 | 3 |
| 6B | 0.00013 | 5 | 13 | 5 | >209126 | 5 |
| 7 | 0.00047 | 3 | 12 | 3 | 24500 | 3 |
| 7A | 0.024 | 3 | 12 | 3 | 508 | 3 |
| 7B | 0.00017 | 3 | 13 | 3 | 101083 | 3 |
| 8 | 0.00013 | 3 | 12 | 3 | 112292 | 3 |
| 8A | 0.28 | 4 | 12 | 4 | 43 | 4 |
| 8B | 0.000066 | 6 | 14 | 7 | >62700 | 6 |
| 9 | 0.00096 | 3 | 11 | 3 | 12700 | 3 |
| 9A | 0.031 | 3 | 12 | 3 | 392 | 3 |
| 9B | 0.00040 | 3 | 13 | 3 | 28400 | 3 |
| 10 | 0.00024 | 3 | 10 | 3 | 44300 | 3 |
| 10A | 0.00019 | 3 | 13 | 3 | 79200 | 3 |
| 10B | 0.0055 | 3 | 8.8 | 3 | 1620 | 3 |
| 11 | 0.00066 | 3 | 11 | 3 | 20600 | 3 |
| 11A | 0.015 | 3 | 12 | 3 | 837 | 3 |
| 11B | 0.00015 | 3 | 12 | 3 | 124345 | 3 |
| 12 | 0.00073 | 4 | 12 | 4 | 17700 | 4 |
| 12A | 0.38 | 3 | 12 | 3 | 32 | 3 |
| 12B | 0.00035 | 3 | 12 | 3 | 34900 | 3 |

N = the number of independent experiments in which the compounds were tested.

Tetravalent Reverse Transcriptase Quantitative-PCR (RT-qPCR) Assay

The antiviral activity of the compounds of the invention was tested against DENV-1 strain TC974#666 (NCPV), DENV-2 strain 16681, DENV-3 strain H87 (NCPV) and DENV-4 strain H241 (NCPV) in a RT-qPCR assay. Therefore, Vero cells were infected with either DENV-1, or -2, or -3, or -4 in the presence or absence of test compounds. At day 3 post-infection, the cells were lysed and cell lysates were used to prepare cDNA of both a viral target (the 3'UTR of DENV; Table 2) and a cellular reference gene (β-actin, Table 2). Subsequently, a duplex real time PCR was performed on a Lightcycler480 instrument. The generated Cp value is inversely proportional to the amount of RNA expression of these targets. Inhibition of DENV replication by a test compound results in a shift of Cp's for the 3'UTR gene. On the other hand, if a test compound is toxic to the cells, a similar effect on β-actin expression will be observed. The comparative ΔΔCp method is used to calculate $EC_{50}$, which is based on the relative gene expression of the target gene (3'UTR) normalized with the cellular housekeeping gene (β-actin). In addition, $CC_{50}$ values are determined based on the $C_p$ values acquired for the housekeeping gene β-actin.

TABLE 2

Primers and probes used for the real-time, quantitative RT-PCR.

| Primer/ probe | Target | Sequence[a,b] |
|---|---|---|
| F3utr258 | DENV 3'-UTR | 5'-CGGTTAGAGGAGACCCCTC-3' |
| R3utr425 | DENV 3'-UTR | 5'-GAGACAGCAGGATCTCTGGTC-3' |
| P3utr343 | DENV 3'-UTR | FAM-5'-AAGGACTAG-ZEN-AAGGTTAGAGGAGACCCCCC-3'IABkFQ |

TABLE 2-continued

Primers and probes used for the real-time, quantitative RT-PCR.

| Primer/probe | Target | Sequence[a,b] |
|---|---|---|
| Factin743 | β-actin | 5'-GGCCAGGTCATCACCATT-3' |
| Ractin876 | β-actin | 5'-ATGTCCACGTCACACTTCATG-3' |
| Pactin773 | β-actin | *HEX*-5'-TTCCGCTGC-*ZEN*-CCTGAGGCTCTC-3'*IABkFQ* |

[a] Reporter dyes (FAM, HEX) and quenchers (ZEN and IABkFQ) elements are indicated in bold and italics.
[b] The nucleotide sequence of the primers and probes were selected from the conserved region in the 3'UTR region of the dengue virus genome, based on the alignment of 300 nucleotide sequences of the four dengue serotypes deposited in Genbank (Gong et al., 2013, Methods Mol Biol, Chapter 16).

The culture medium consisted of minimal essential medium supplemented with 2% of heat-inactivated fetal calf serum, 0.04% gentamycin (50 mg/mL) and 2 mM of L-glutamine. Vero cells, obtained from ECACC, were suspended in culture medium and 75 µL/well was added in 96-well plates (10000 cells/well), which already contain the antiviral compounds. Typically, these plates contain a 5-fold serial dilution of 9 dilution steps of the test compound at 200 times the final concentration in 100% DMSO (500 nL; final concentration range: 25 µM-0.000064 µM or 2.5p M-0.0000064 µM for the most active compounds). In addition, each plate contains wells which are assigned as virus controls (containing cells and virus in the absence of compound) and cell controls (containing cells in the absence of virus and compound). Once the cells were added in the plates, the plates were incubated in a fully humidified incubator (37° C., 5% $CO_2$) until the next day. Dengue viruses serotype-1, -2, -3 and -4 were diluted in order to obtain a Cp of ~22-24 in the assay. Therefore, 25 µL of virus suspension was added to all the wells containing test compound and to the wells assigned as virus control. In parallel, 25 µL of culture medium was added to the cell controls. Next, the plates were incubated for 3 days in a fully humidified incubator (37° C., 5% $CO_2$). After 3 days, the supernatant was removed from the wells and the cells were washed twice with ice-cold PBS (~100 µL). The cell pellets within the 96-well plates were stored at −80° C. for at least 1 day. Next, RNA was extracted using the Cells-to-CT$^{Tm}$ lysis kit, according to the manufacturer's guideline (Life Technologies). The cell lysates can be stored at −80° C. or immediately used in the reverse transcription step.

In preparation of the reverse transcription step, mix A (table 3A) was prepared and 7.57 µL/well was dispensed in a 96-well plate. After addition of 5 µL of the cell lysates, a five minute denaturation step at 75° C. was performed (table 3B). Afterwards, 7.43 µL of mix B was added (table 3C) and the reverse transcription step was initiated (table 3D) to generate cDNA.

Finally, a RT-qPCR mix was prepared, mix C (table 4A), and 22.02 µL/well was dispensed in 96-well LightCycler qPCR plates to which 3 µL of cDNA was added and the qPCR was performed according to the conditions in table 4B on a LightCycler 480.

Using the LightCycler software and an in-house LIMS system, dose response curves for each compound were calculated and the half maximal effective concentration ($EC_{50}$) and the half maximal cytotoxic concentration ($CC_{50}$) were determined (Tables 5-8).

TABLE 3 cDNA synthesis using Mix A, denaturation, Mix B and reverse transcription.

A
Mix A

| | | | | | |
|---|---|---|---|---|---|
| Plates | 8 | | | Reaction Vol. (µl) | 20 |
| Samples | 828 | | | Volume for (µl) | |
| | | Concentration | | | |
| Mix Item | Unit | Stock | Final | 1 sample | x samples |
| Milli-Q $H_2O$ | | | | 7.27 | 6019.56 |
| R3utr425 | µM | 20 | 0.27 | 0.15 | 124.20 |
| Ractin876 | µM | 20 | 0.27 | 0.15 | 124.20 |
| | | Volume mix/well (µl) | | 7.57 | |
| | | Cell lysates | | 5.00 | |

B
Denaturation step:

| Step | Temp | Time |
|---|---|---|
| Denaturation | 75° C. | 5' |
| Hold | 4° C. | hold |

C
Mix B

| Samples | 864 | | | | |
|---|---|---|---|---|---|
| | | Concentration | | Volume for (µl) | |
| Mix Item | Unit | Stock | Final | 1 sample | x samples |
| Expand HIFI buffer 2 | X | 10.00 | 1.00 | 2.00 | 1728.0 |
| $MgCl_2$ | mM | 25.00 | 3.50 | 2.80 | 2419.2 |
| dNTPs | mM | 10.00 | 1.00 | 2.00 | 1728.0 |
| Rnase inhibitor | U/µl | 40.00 | 1.00 | 0.50 | 432.0 |
| Expand RT | U/µl | 50.00 | 0.33 | 0.13 | 112.3 |
| | | Total Volume Mi (µl) | | 7.43 | |

D
Protocol cDNA synthesis

| Step | Temp | Time |
|---|---|---|
| Rev transc | 42° C. | 30' |
| Denaturation | 99° C. | 5' |
| Hold | 4° C. | hold |

TABLE 4 qPCR mix and protocol.

A
Mix C

| Samples | | 833 | | Reaction Vol. (μl) | 25 |
|---|---|---|---|---|---|
| | | Concentration | | Volume for (μl) | |
| Mix Item | Unit | Stock | Final | 1 sample | x samples |
| H₂O PCR grade Roche | | | | 7.74 | 6447.42 |
| Roche 2xMM mix | X | 2 | 1 | 12.50 | 10412.50 |
| F3utr258 | μM | 20 | 0.3 | 0.38 | 316.54 |
| R3utr425 | μM | 20 | 0.3 | 0.38 | 316.54 |
| P3utr343 | μM | 20 | 0.1 | 0.13 | 108.29 |
| Factin743 | μM | 20 | 0.3 | 0.38 | 316.54 |
| Ractin876 | μM | 20 | 0.3 | 0.38 | 316.54 |
| Pactin773 | μM | 20 | 0.1 | 0.13 | 108.29 |
| | | Volume Mix/Tube (μl) | | 22.02 | |
| | | cDNA | | 3.00 | |

B
Protocol qPCR3

| Step | Temp | Time | Ramp rate | |
|---|---|---|---|---|
| preincub/denat | 95° C. | 10 min | 4.4 | |
| Denaturation | 95° C. | 10 sec | 4.4 | 40 cycles |
| annealing | 58° C. | 1 min | 2.2 | |
| Elongation | 72° C. | 1 sec | 4.4 | |
| Cooling | 40° C. | 10 sec | 1.5 | |

TABLE 5

$EC_{50}$, $CC_{50}$, and SI for the compounds against serotype 1 in the RT-qPCR assays

| | Protocol A RT-qPCR serotype 1 T0974#666 | | | | | |
|---|---|---|---|---|---|---|
| compound# | $EC_{50}$ (μM) | N | $CC_{50}$ (μM) | N | SI | N |
| 1B | 0.00028 | 4 | 14 | 4 | 34200 | 4 |
| 2B | 0.00030 | 4 | >2.5 | 4 | >19400 | 4 |
| 3B | 0.00018 | 3 | >2.5 | 3 | >30300 | 3 |
| 4B | 0.000048 | 7 | >2.5 | 7 | >85800 | 7 |
| 5B | 0.00074 | 4 | >2.5 | 4 | >6700 | 4 |
| 6B | 0.00047 | 3 | >2.5 | 3 | >8420 | 3 |
| 7B | 0.00061 | 3 | >2.5 | 3 | >6020 | 3 |
| 8B | 0.00015 | 4 | >2.5 | 4 | >30700 | 4 |
| 9B | 0.00022 | 4 | >2.5 | 4 | >24000 | 4 |
| 10A | 0.00016 | 4 | >2.5 | 4 | >33300 | 4 |
| 11B | 0.00067 | 4 | >2.5 | 4 | >6970 | 4 |
| 12B | 0.00068 | 3 | >2.5 | 3 | >6820 | 3 |

N = the number of independent experiments in which the compounds were tested.

TABLE 6

$EC_{50}$, $CC_{50}$, and SI for the compounds against serotype 2 in the RT-qPCR assays

| | Protocol A RT-qPCR serotype 2 16681 | | | | | |
|---|---|---|---|---|---|---|
| compound# | $EC_{50}$ (μM) | N | $CC_{50}$ (μM) | N | SI | N |
| 1B | 0.00048 | 4 | 18 | 3 | 38000 | 3 |
| 2B | 0.00028 | 3 | 14 | 3 | 76100 | 3 |
| 3B | 0.00012 | 3 | 10 | 3 | 81700 | 3 |
| 4B | 0.000060 | 7 | >2.5 | 5 | >65500 | 5 |
| 5B | 0.00017 | 3 | >2.5 | 3 | >16000 | 3 |
| 6B | 0.00015 | 3 | >2.5 | 3 | >23800 | 3 |
| 7B | 0.00028 | 4 | >2.5 | 4 | >34500 | 4 |
| 8B | 0.000062 | 3 | >2.5 | 3 | >43700 | 3 |
| 9B | 0.00030 | 3 | >2.5 | 3 | >18200 | 3 |
| 10A | 0.00020 | 3 | >2.5 | 3 | >24400 | 3 |
| 11B | 0.00017 | 3 | >2.5 | 3 | >18300 | 3 |
| 12B | 0.00022 | 3 | >2.5 | 3 | >12900 | 3 |

N = the number of independent experiments in which the compounds were tested.

TABLE 7

$EC_{50}$, $CC_{50}$, and SI for the compounds against serotype 3 in the RT-qPCR assays

| | Protocol A RT-qPCR serotype 3 H87 | | | | | |
|---|---|---|---|---|---|---|
| compound# | $EC_{50}$ (μM) | N | $CC_{50}$ (μM) | N | SI | N |
| 1B | 0.0034 | 3 | >2.5 | 3 | >909 | 3 |
| 2B | 0.0046 | 3 | >2.5 | 3 | >1200 | 3 |
| 3B | 0.0011 | 3 | >2.5 | 3 | >5170 | 3 |
| 4B | 0.00066 | 7 | >2.5 | 6 | >5610 | 6 |
| 5B | 0.0046 | 3 | >2.5 | 3 | >1050 | 3 |
| 6B | 0.0017 | 3 | >2.5 | 3 | >2170 | 3 |
| 7B | 0.0058 | 3 | >2.5 | 3 | >1080 | 3 |
| 8B | 0.0010 | 3 | >2.5 | 3 | >2740 | 3 |
| 9B | 0.0041 | 3 | >2.5 | 3 | >1360 | 3 |
| 10A | 0.0021 | 3 | >2.5 | 3 | >1290 | 3 |
| 11B | 0.0054 | 3 | >2.5 | 3 | >604 | 3 |
| 12B | 0.0041 | 3 | >2.5 | 3 | >1240 | 3 |

N = the number of independent experiments in which the compounds were tested.

TABLE 8

$EC_{50}$, $CC_{50}$, and SI for the compounds against serotype 4 in the RT-qPCR assays

| | Protocol A RT-qPCR serotype 4 H241 | | | | | |
|---|---|---|---|---|---|---|
| compound# | $EC_{50}$ (μM) | N | $CC_{50}$ (μM) | N | SI | N |
| 1B | 0.051 | 4 | 8.3 | 3 | 173 | 3 |
| 2B | 0.030 | 4 | 9.5 | 4 | 587 | 4 |
| 3B | 0.014 | 3 | 1.2 | 3 | 85 | 3 |
| 4B | 0.011 | 10 | 9.1 | 9 | 682 | 9 |
| 5B | 0.024 | 3 | 9.6 | 3 | 530 | 3 |
| 6B | 0.016 | 3 | >2.5 | 3 | >232 | 3 |
| 7B | 0.025 | 3 | 9.4 | 3 | 531 | 3 |
| 8B | 0.012 | 3 | 5.8 | 3 | 334 | 3 |
| 9B | 0.031 | 3 | 15 | 3 | 570 | 3 |
| 10A | 0.010 | 3 | 15 | 2 | 2640 | 2 |
| 11B | 0.022 | 3 | 11 | 3 | 697 | 3 |
| 12B | 0.028 | 3 | 10 | 3 | 348 | 3 |

N = the number of independent experiments in which the compounds were tested.

Prior Art Examples

Compounds (56) and (170) disclosed in WO-2013/045516 have been tested in an analogous DENV-2 antiviral assay as the compounds of the present invention and their reported activity is listed below.

compound (56)
of WO-2013/045515

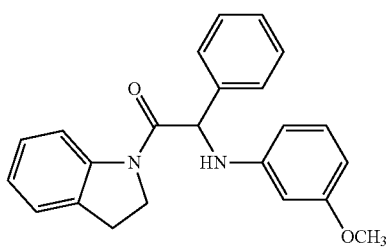

compound (170)
of WO-2013/045516

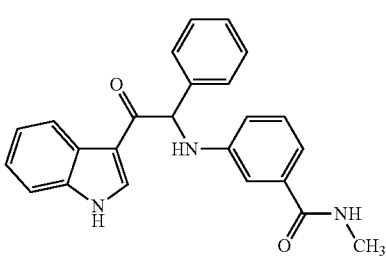

TABLE 9

| EC$_{50}$, CC$_{50}$, and SI for compounds (56) and (170) disclosed in the DENV-2 antiviral assay ||||
| --- | --- | --- | --- |
| compound# | EC$_{50}$ (μM) | CC$_{50}$ (μM) | SI |
| (56) of WO-2013/045516 | 0.45 | >139 | >312 |
| (170) of WO-2013/045516 | 0.44 | 26 | 58 |

ABBREVIATIONS USED IN EXPERIMENTAL PART

| | |
| --- | --- |
| (M + H)$^+$ | protonated molecular ion |
| aq. | aqueous |
| Boc | tert-butyloxycarbonyl |
| Boc$_2$O | di-tert-butyl dicarbonate |
| br | broad |
| CH$_3$CN | acetonitrile |
| CHCl$_3$ | chloroform |
| CH$_2$Cl$_2$ | dichloromethane |
| CO$_2$ | carbon dioxide |
| d | doublet |
| DCM | dichloromethane |
| DIEA | diisopropylethylamine |
| DIPE | diisopropyl ether |
| DMA | dimethylacetamide |
| DMAP | 4-dimethylaminopyridine |
| DME | 1,2-dimethoxyethane |
| DMF | dimethylformamide |
| DMSO | dimethyl sulfoxide |
| eq. | equivalent |
| Et$_2$O | diethyl ether |
| Et$_3$N | triethylamine |
| EtOAc | ethyl acetate |
| EtOH | ethanol |
| H$_2$O | water |
| H$_2$SO$_4$ | sulfuric acid |
| HCl | hydrochloric acid |
| HPLC | high performance liquid chromatography |
| iPrNH$_2$ | isopropylamine |
| IprOH | 2-propanol |
| K$_2$CO$_3$ | potassium carbonate |
| K$_3$PO$_4$ | potassium orthophosphate |
| LiAlH$_4$ | lithium aluminium hydride |
| m/z | mass-to-charge ratio |
| Me | methyl |
| MeOH | methanol |
| MgSO$_4$ | magnesium sulfate |
| min | minute(s) |
| N$_2$ | nitrogen |
| Na$_2$CO$_3$ | sodium carbonate |
| Na$_2$SO$_4$ | sodium sulfate |
| NaBH$_4$ | sodium borohydride |
| NaHCO$_3$ | sodium bicarbonate |
| NaNO$_2$ | sodium nitrite |
| NaOH | sodium hydroxide |
| q | quartet |
| rt or RT | room temperature |
| s | singlet |
| t | triplet |
| tBuOH | tert-butanol |
| TEA | triethylamine |
| TFA | trifluoroacetic acid |
| THF | tetrahydrofuran |
| TMSCl | trimethylsilyl chloride |

The invention claimed is:
1. A compound selected from the group consisting of:
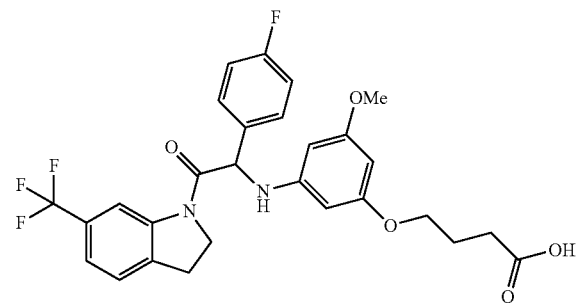
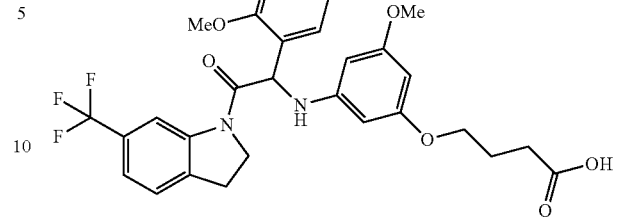
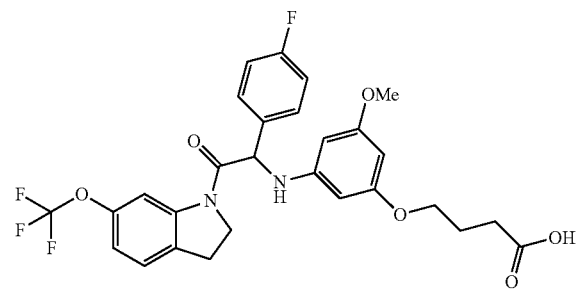
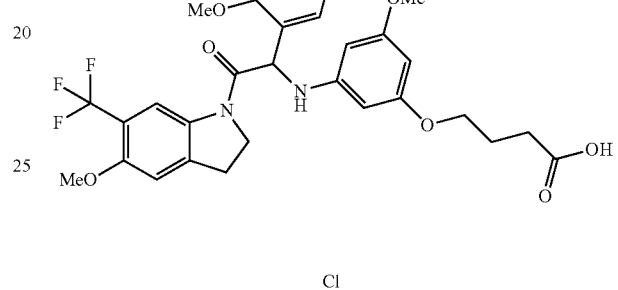
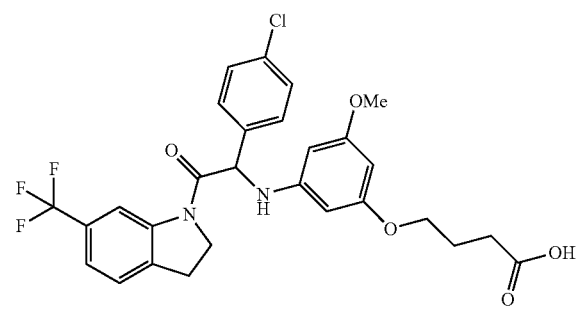
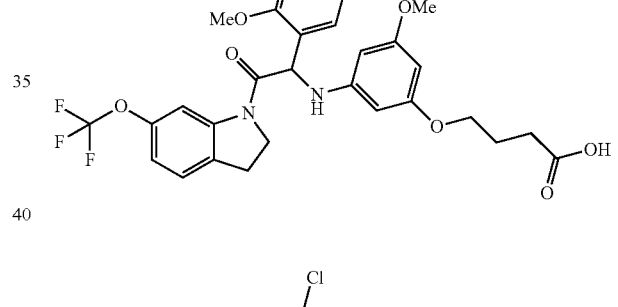
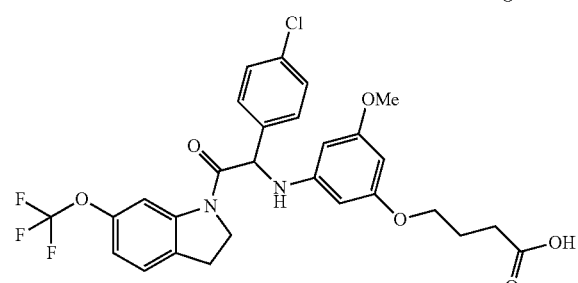
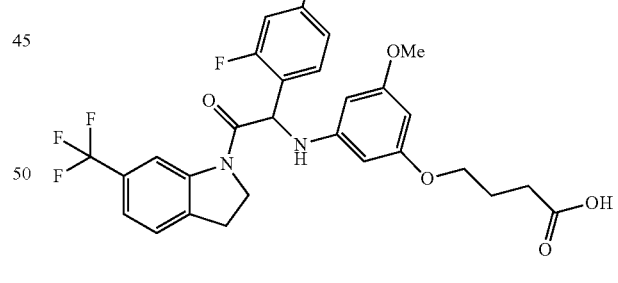
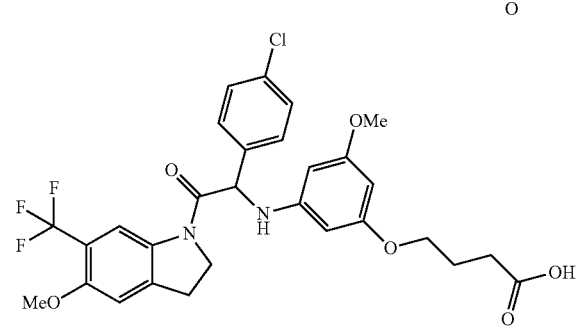
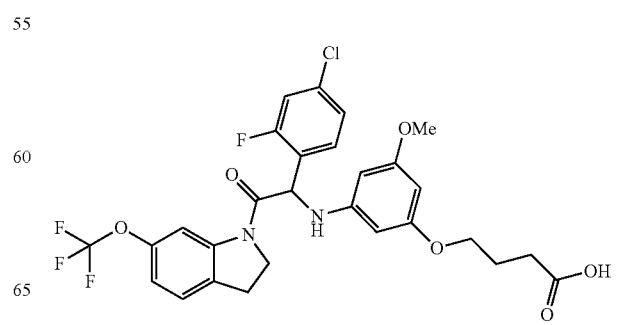

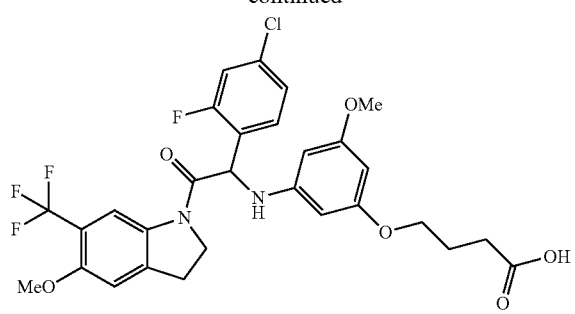
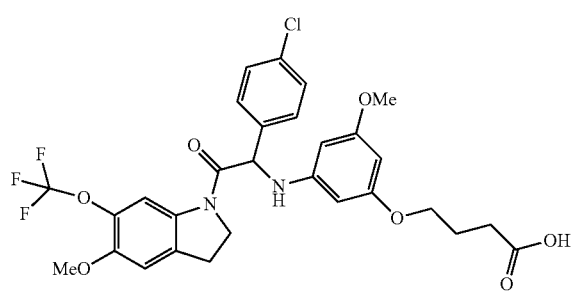
and stereoisomeric forms, pharmaceutically acceptable salts, solvates or polymorphs thereof.
2. A pharmaceutical composition comprising the compound of claim 1 together with one or more pharmaceutically acceptable excipients, diluents or carriers.
3. The compound as claimed in claim 1 wherein the compound is
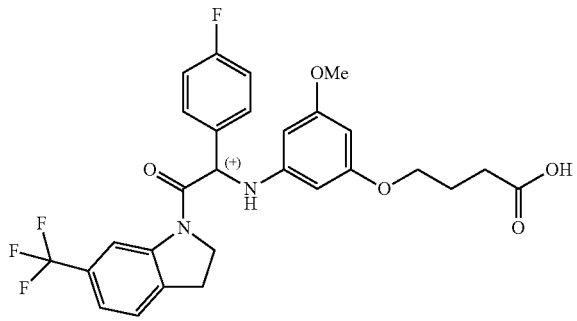
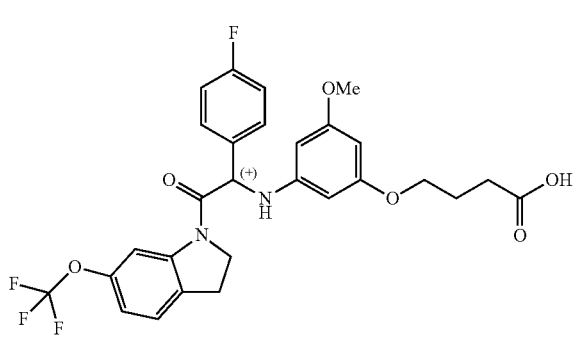
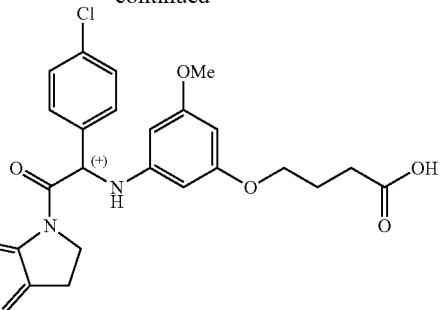
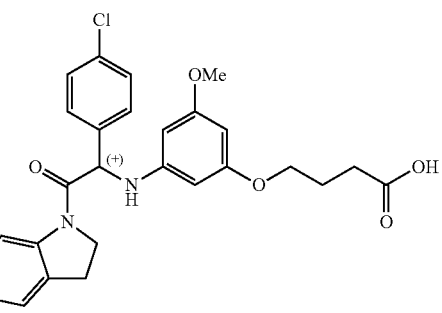
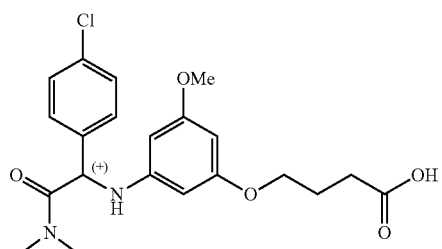
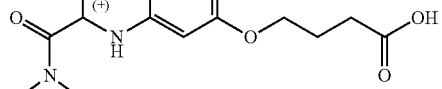

91

-continued

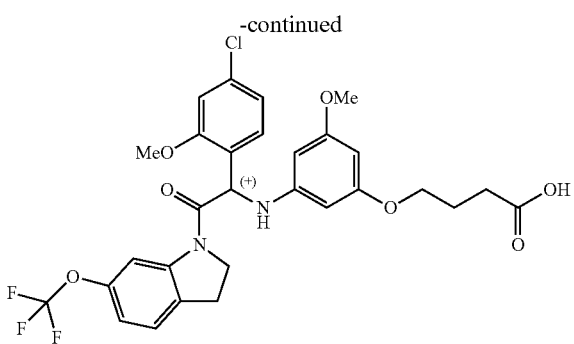

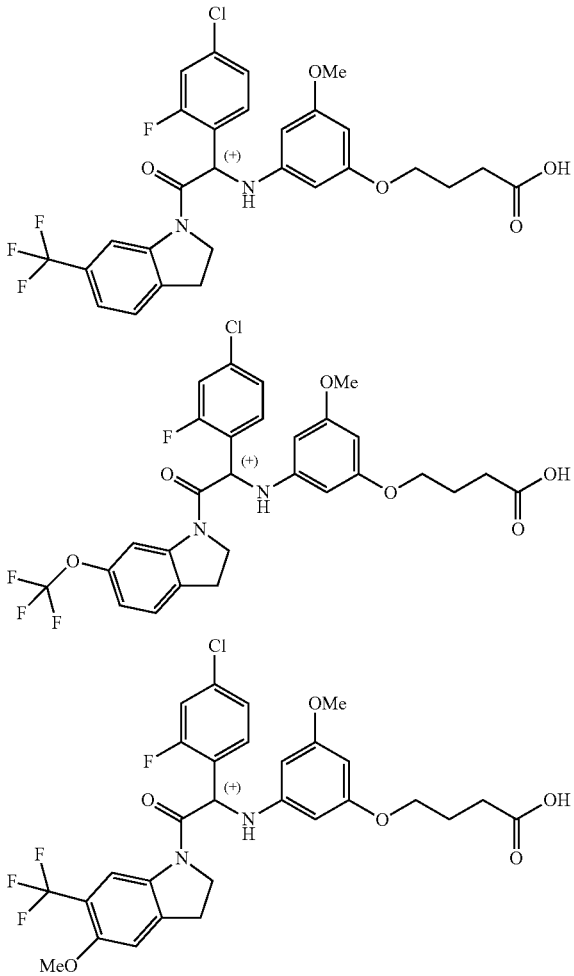

92

-continued

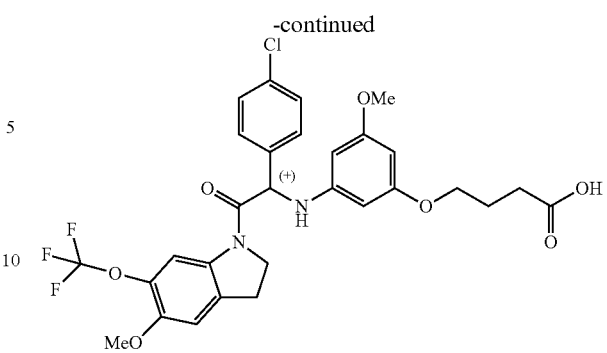

or a pharmaceutically acceptable salt, solvate or polymorph thereof.

4. A pharmaceutical composition comprising a compound of claim 3 together with one or more pharmaceutically acceptable excipients, diluents or carriers.

5. A compound of claim 1 having the formula 4:

4

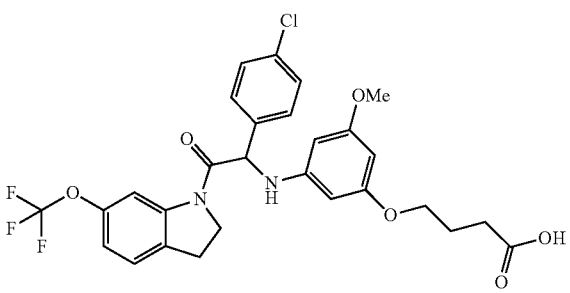

or a stereoisomeric form, a pharmaceutically acceptable salt, solvate or polymorph thereof.

6. A compound or a stereoisomer, a pharmaceutically acceptable salt, solvate, or polymorph thereof according to claim 1, wherein said compound is in a crystalline form.

7. A compound or a stereoisomer, a pharmaceutically acceptable salt, or solvate thereof according to claim 1, wherein said compound is in an amorphous form.

8. A compound or a stereoisomer, a pharmaceutically acceptable salt, solvate, or polymorph thereof according to claim 1, wherein said compound is in an un-solvated form.

\* \* \* \* \*